United States Patent
Voss et al.

(10) Patent No.: US 12,016,820 B2
(45) Date of Patent: Jun. 25, 2024

(54) ENHANCED GUIDED ACTIVE COMPRESSION DECOMPRESSION CARDIOPULMONARY RESUSCITATION SYSTEMS AND METHODS

(71) Applicant: ZOLL Medical Corporation, Chelmsford, MA (US)

(72) Inventors: Greg Voss, Lakeville, MN (US); Anja Metzger, Stillwater, MN (US); Keith G. Lurie, Minneapolis, MN (US); Demetris Yannopoulos, Edina, MN (US)

(73) Assignee: ZOLL Medical Corporation, Chelmsford, MA (US)

( * ) Notice: Subject to any disclaimer, the term of this patent is extended or adjusted under 35 U.S.C. 154(b) by 143 days.

(21) Appl. No.: 17/403,053

(22) Filed: Aug. 16, 2021

(65) Prior Publication Data
US 2022/0071840 A1 Mar. 10, 2022

Related U.S. Application Data

(63) Continuation of application No. 15/638,452, filed on Jun. 30, 2017, now Pat. No. 11,123,261, which is a
(Continued)

(51) Int. Cl.
*A61H 31/00* (2006.01)

(52) U.S. Cl.
CPC ......... *A61H 31/004* (2013.01); *A61H 31/005* (2013.01); *A61H 31/006* (2013.01);
(Continued)

(58) Field of Classification Search
CPC .. A61H 31/004; A61H 31/005; A61H 31/006; A61H 2201/5043; A61H 2201/5061; A61H 2201/5064; A61H 2201/5084; A61H 2230/207; A61H 2230/42; A61H 2230/50; A61H 2031/002; A61H 2201/10; A61H 2201/5007; A61H 31/007; A61H 2201/0107; A61H 2230/04;
(Continued)

(56) References Cited

U.S. PATENT DOCUMENTS

| 1,848,232 A | 3/1932 | Swope et al. |
| 2,325,049 A | 7/1943 | Frye et al. |

(Continued)

FOREIGN PATENT DOCUMENTS

| AU | 1487792 B | 10/1992 |
| AU | 60539 B | 11/1994 |

(Continued)

OTHER PUBLICATIONS

US 5,584,866 A, 12/1996, Kroll et al. (withdrawn)
(Continued)

*Primary Examiner* — Quang D Thanh
(74) *Attorney, Agent, or Firm* — The Webb Law Firm

(57) ABSTRACT

Systems and methods for applying enhanced guided active compression decompression cardiopulmonary resuscitation are provided. Exemplary systems include a load cell, a handle, an adhesive pad. The handle and the adhesive pad are configured for magnetic coupling.

20 Claims, 20 Drawing Sheets

Related U.S. Application Data continuation of application No. 13/554,986, filed on Jul. 20, 2012, now Pat. No. 9,724,266, which is a continuation-in-part of application No. 13/554,458, filed on Jul. 20, 2012, now abandoned, and a continuation-in-part of application No. 13/175,670, filed on Jul. 1, 2011, now abandoned, and a continuation-in-part of application No. 13/026,459, filed on Feb. 14, 2011, now Pat. No. 8,702,633.

(60) Provisional application No. 61/577,565, filed on Dec. 19, 2011, provisional application No. 61/509,994, filed on Jul. 20, 2011, provisional application No. 61/485,944, filed on May 13, 2011, provisional application No. 61/361,208, filed on Jul. 2, 2010, provisional application No. 61/304,148, filed on Feb. 12, 2010.

(52) U.S. Cl.
CPC ............ *A61H 2201/5043* (2013.01); *A61H 2201/5061* (2013.01); *A61H 2201/5064* (2013.01); *A61H 2201/5084* (2013.01); *A61H 2230/207* (2013.01); *A61H 2230/42* (2013.01); *A61H 2230/50* (2013.01)

(58) Field of Classification Search
CPC ............ A61N 1/046; A61N 1/39044; A61M 16/0009
See application file for complete search history.

(56) References Cited

U.S. PATENT DOCUMENTS

| | | |
|---|---|---|
| 2,774,346 A | 12/1956 | Halliburton |
| 2,854,982 A | 10/1958 | Pagano |
| 2,904,898 A | 9/1959 | Marsden |
| 3,009,266 A | 11/1961 | Brook |
| 3,049,811 A | 8/1962 | Ruben |
| 3,068,590 A | 12/1962 | Padellford |
| 3,077,884 A | 2/1963 | Batrow et al. |
| 3,191,596 A | 6/1965 | Bird et al. |
| 3,199,225 A | 8/1965 | Robertson et al. |
| 3,209,469 A | 10/1965 | James |
| 3,216,413 A | 11/1965 | Mota |
| 3,274,705 A | 9/1966 | Breakspear |
| 3,276,147 A | 10/1966 | Padellford |
| 3,307,541 A | 3/1967 | Hewson |
| 3,357,426 A | 12/1967 | Cohen |
| 3,420,232 A | 1/1969 | Bickford |
| 3,459,216 A | 8/1969 | Bloom et al. |
| 3,467,092 A | 9/1969 | Bird et al. |
| 3,509,899 A | 5/1970 | Hewson |
| 3,515,163 A | 6/1970 | Freeman |
| 3,523,529 A | 8/1970 | Kissen |
| 3,552,390 A | 1/1971 | Muller |
| 3,562,924 A | 2/1971 | Baerman et al. |
| 3,562,925 A | 2/1971 | Baermann et al. |
| 3,568,333 A | 3/1971 | Clark |
| 3,662,751 A | 5/1972 | Barkalow et al. |
| 3,669,108 A | 6/1972 | Sundblom et al. |
| 3,734,100 A | 5/1973 | Walker et al. |
| 3,739,776 A | 6/1973 | Bird et al. |
| 3,794,043 A | 2/1974 | McGinnis |
| 3,815,606 A | 6/1974 | Mazal |
| 3,834,383 A | 9/1974 | Weigl et al. |
| 3,872,609 A | 3/1975 | Smrcka |
| 3,874,093 A | 4/1975 | Garbe |
| 3,875,626 A | 4/1975 | Tysk et al. |
| 3,933,171 A | 1/1976 | Hay |
| 3,949,388 A | 4/1976 | Fuller |
| 3,973,564 A | 8/1976 | Carden |
| 3,981,398 A | 9/1976 | Boshoff |
| 3,993,059 A | 11/1976 | Sjostrand |
| 4,037,595 A | 7/1977 | Elam |
| 4,041,943 A | 8/1977 | Miller |
| 4,054,134 A | 10/1977 | Kritzer |
| 4,077,400 A | 3/1978 | Harrigan |
| 4,077,404 A | 3/1978 | Elam |
| 4,095,590 A | 6/1978 | Harrigan |
| 4,166,458 A | 9/1979 | Harrigan |
| 4,193,406 A | 3/1980 | Jinotti |
| 4,198,963 A | 4/1980 | Barkalow et al. |
| 4,226,233 A | 10/1980 | Kritzer |
| 4,237,872 A | 12/1980 | Harrigan |
| 4,240,419 A | 12/1980 | Furlong et al. |
| 4,259,951 A | 4/1981 | Chernack et al. |
| 4,262,667 A | 4/1981 | Grant |
| 4,297,999 A | 11/1981 | Kitrell |
| 4,298,023 A | 11/1981 | McGinnis |
| 4,316,458 A | 2/1982 | Hammerton-Fraser |
| 4,320,754 A | 3/1982 | Watson et al. |
| 4,326,507 A | 4/1982 | Barkalow |
| 4,331,426 A | 5/1982 | Sweeney |
| 4,349,015 A | 9/1982 | Alferness |
| 4,360,345 A | 11/1982 | Hon |
| 4,397,306 A | 8/1983 | Weisfeldt et al. |
| 4,424,806 A | 1/1984 | Newman et al. |
| 4,446,864 A | 5/1984 | Watson et al. |
| 4,448,192 A | 5/1984 | Stawitcke et al. |
| 4,449,526 A | 5/1984 | Elam |
| 4,481,938 A | 11/1984 | Lindley |
| 4,501,582 A | 2/1985 | Schulz |
| 4,513,737 A | 4/1985 | Mabuchi |
| 4,519,388 A | 5/1985 | Schwanbom et al. |
| 4,520,811 A | 6/1985 | White et al. |
| 4,533,137 A | 8/1985 | Sonne |
| 4,543,951 A | 10/1985 | Phuc |
| 4,588,383 A | 5/1986 | Parker et al. |
| 4,598,706 A | 7/1986 | Darowski et al. |
| 4,601,465 A | 7/1986 | Roy |
| 4,602,653 A | 7/1986 | Ruiz-Vela et al. |
| 4,637,386 A | 1/1987 | Baum |
| 4,774,941 A | 10/1988 | Cook |
| 4,797,104 A | 1/1989 | Laerdal et al. |
| 4,807,638 A | 2/1989 | Sramek |
| 4,809,683 A | 3/1989 | Hanson |
| 4,827,935 A | 5/1989 | Geddes et al. |
| 4,828,501 A | 5/1989 | Ingenito et al. |
| 4,863,385 A | 9/1989 | Pierce |
| 4,881,527 A | 11/1989 | Lerman |
| 4,898,166 A | 2/1990 | Rose et al. |
| 4,898,167 A | 2/1990 | Pierce et al. |
| 4,928,674 A | 5/1990 | Halperin et al. |
| 4,932,879 A | 6/1990 | Ingenito et al. |
| 4,971,042 A | 11/1990 | Lerman |
| 4,971,051 A | 11/1990 | Toffolon |
| 4,984,987 A | 1/1991 | Brault et al. |
| 5,014,698 A | 5/1991 | Cohen |
| 5,016,627 A | 5/1991 | Dahrendorf et al. |
| 5,029,580 A | 7/1991 | Radford et al. |
| 5,042,500 A | 8/1991 | Norlien et al. |
| 5,050,593 A | 9/1991 | Poon |
| 5,056,505 A | 10/1991 | Warwick et al. |
| 5,083,559 A | 1/1992 | Brault et al. |
| 5,109,840 A | 5/1992 | Daleiden |
| 5,119,825 A | 6/1992 | Huhn |
| 5,150,291 A | 9/1992 | Cummings et al. |
| 5,163,424 A | 11/1992 | Kohnke |
| 5,183,038 A | 2/1993 | Hoffman et al. |
| 5,184,620 A | 2/1993 | Cudahy et al. |
| 5,188,098 A | 2/1993 | Hoffman et al. |
| 5,193,529 A | 3/1993 | Labaere |
| 5,193,544 A | 3/1993 | Jaffe |
| 5,195,896 A | 3/1993 | Sweeney et al. |
| 5,217,006 A | 6/1993 | McCulloch |
| 5,231,086 A | 7/1993 | Sollevi |
| 5,235,970 A | 8/1993 | Augustine |
| 5,238,409 A | 8/1993 | Brault et al. |
| 5,239,988 A | 8/1993 | Swanson et al. |
| 5,263,476 A | 11/1993 | Henson |
| 5,265,595 A | 11/1993 | Rudolph |
| 5,282,463 A | 2/1994 | Hammersley |

(56) References Cited

U.S. PATENT DOCUMENTS

| | | | |
|---|---|---|---|
| 5,295,481 A * | 3/1994 | Geeham | A61N 1/38 601/43 |
| 5,301,667 A | 4/1994 | McGrail et al. | |
| 5,305,743 A | 4/1994 | Brain | |
| 5,306,293 A | 4/1994 | Zacouto | |
| 5,312,259 A | 5/1994 | Flynn | |
| 5,313,938 A | 5/1994 | Garfield et al. | |
| 5,316,907 A | 5/1994 | Lurie et al. | |
| 5,330,514 A | 7/1994 | Egelandsdal et al. | |
| 5,335,654 A | 8/1994 | Rapoport | |
| 5,353,788 A | 10/1994 | Miles | |
| 5,355,879 A | 10/1994 | Brain | |
| 5,359,998 A | 11/1994 | Lloyd | |
| 5,366,231 A | 11/1994 | Hung | |
| 5,377,671 A | 1/1995 | Biondi et al. | |
| 5,383,786 A | 1/1995 | Kohnke | |
| 5,388,575 A | 2/1995 | Taube | |
| 5,392,774 A | 2/1995 | Sato | |
| 5,395,399 A | 3/1995 | Rosenwald | |
| 5,397,237 A | 3/1995 | Dhont et al. | |
| 5,398,714 A | 3/1995 | Price | |
| 5,413,110 A | 5/1995 | Cummings et al. | |
| 5,423,685 A | 6/1995 | Adamson et al. | |
| 5,423,772 A | 6/1995 | Lurie et al. | |
| 5,437,272 A | 8/1995 | Fuhrman | |
| 5,452,715 A | 9/1995 | Boussignac | |
| 5,454,779 A | 10/1995 | Lurie et al. | |
| 5,468,151 A | 11/1995 | Egelandsdal et al. | |
| 5,474,533 A | 12/1995 | Ward et al. | |
| 5,477,860 A | 12/1995 | Essen-Moller | |
| 5,490,820 A | 2/1996 | Schock et al. | |
| 5,492,115 A | 2/1996 | Abramov et al. | |
| 5,492,116 A | 2/1996 | Scarberry et al. | |
| 5,496,257 A | 3/1996 | Kelly | |
| 5,517,986 A | 5/1996 | Starr et al. | |
| 5,544,648 A | 8/1996 | Fischer, Jr. | |
| 5,549,106 A | 8/1996 | Gruenke et al. | |
| 5,549,581 A | 8/1996 | Lurie et al. | |
| 5,551,420 A | 9/1996 | Lurie et al. | |
| 5,557,049 A | 9/1996 | Ratner | |
| 5,580,255 A | 12/1996 | Flynn | |
| 5,582,182 A | 12/1996 | Hillsman | |
| 5,588,422 A | 12/1996 | Urie et al. | |
| 5,593,306 A | 1/1997 | Kohnke | |
| 5,614,490 A | 3/1997 | Przybelski | |
| 5,617,844 A | 4/1997 | King | |
| 5,618,665 A | 4/1997 | Lurie et al. | |
| 5,619,665 A | 4/1997 | Emma | |
| 5,628,305 A | 5/1997 | Melker | |
| 5,632,298 A | 5/1997 | Artinian | |
| 5,643,231 A | 7/1997 | Lurie et al. | |
| 5,645,522 A | 7/1997 | Lurie et al. | |
| 5,657,751 A | 8/1997 | Karr, Jr. | |
| 5,678,535 A | 10/1997 | DiMarco | |
| 5,685,298 A | 11/1997 | Idris | |
| 5,692,498 A | 12/1997 | Lurie et al. | |
| 5,697,364 A | 12/1997 | Chua et al. | |
| 5,701,883 A | 12/1997 | Hete et al. | |
| 5,701,889 A | 12/1997 | Danon | |
| 5,704,346 A | 1/1998 | Inoue | |
| 5,720,282 A | 2/1998 | Wright | |
| 5,722,963 A | 3/1998 | Lurie et al. | |
| 5,730,122 A | 3/1998 | Lurie | |
| 5,735,876 A | 4/1998 | Kroll et al. | |
| 5,738,637 A | 4/1998 | Kelly et al. | |
| 5,743,864 A | 4/1998 | Baldwin, II | |
| 5,782,883 A | 7/1998 | Kroll et al. | |
| 5,794,615 A | 8/1998 | Estes | |
| 5,806,512 A | 9/1998 | Abramov et al. | |
| 5,814,086 A | 9/1998 | Hirschberg et al. | |
| 5,817,997 A | 10/1998 | Wernig | |
| 5,823,185 A | 10/1998 | Chang | |
| 5,823,787 A | 10/1998 | Gonzalez et al. | |
| 5,827,893 A | 10/1998 | Lurie et al. | |
| 5,832,920 A | 11/1998 | Field | |
| 5,853,292 A | 12/1998 | Eggert et al. | |
| 5,881,725 A | 3/1999 | Hoffman et al. | |
| 5,885,084 A | 3/1999 | Pastrick et al. | |
| 5,891,062 A | 4/1999 | Schock et al. | |
| 5,896,857 A | 4/1999 | Hely et al. | |
| 5,916,165 A | 6/1999 | Duchon et al. | |
| 5,919,210 A | 7/1999 | Lurie et al. | |
| 5,927,273 A | 7/1999 | Federowicz et al. | |
| 5,937,853 A | 8/1999 | Strom | |
| 5,941,710 A | 8/1999 | Lampotang et al. | |
| 5,975,081 A | 11/1999 | Hood et al. | |
| 5,977,091 A | 11/1999 | Nieman et al. | |
| 5,984,909 A | 11/1999 | Lurie et al. | |
| 5,988,166 A | 11/1999 | Hayek | |
| 6,001,085 A | 12/1999 | Lurie et al. | |
| 6,010,470 A | 1/2000 | Albery et al. | |
| 6,029,667 A | 2/2000 | Lurie | |
| 6,042,532 A | 3/2000 | Freed et al. | |
| 6,062,219 A | 5/2000 | Lurie et al. | |
| 6,078,834 A | 6/2000 | Lurie et al. | |
| 6,086,582 A | 7/2000 | Altman et al. | |
| 6,123,074 A | 9/2000 | Hete et al. | |
| 6,131,571 A | 10/2000 | Lampotang et al. | |
| 6,155,257 A | 12/2000 | Lurie et al. | |
| 6,155,647 A | 12/2000 | Albecker, III | |
| 6,165,105 A | 12/2000 | Boutellier et al. | |
| 6,167,879 B1 | 1/2001 | Sievers et al. | |
| 6,174,295 B1 | 1/2001 | Cantrell et al. | |
| 6,176,237 B1 | 1/2001 | Wunderlich et al. | |
| 6,193,519 B1 | 2/2001 | Eggert et al. | |
| 6,209,540 B1 | 4/2001 | Sugiura et al. | |
| 6,224,562 B1 | 5/2001 | Lurie et al. | |
| 6,234,916 B1 | 5/2001 | Carusillo et al. | |
| 6,234,985 B1 | 5/2001 | Lurie et al. | |
| 6,277,107 B1 | 8/2001 | Lurie et al. | |
| 6,296,490 B1 | 10/2001 | Bowden | |
| 6,312,399 B1 | 11/2001 | Lurie et al. | |
| 6,334,441 B1 | 1/2002 | Zowtiak et al. | |
| 6,356,785 B1 | 3/2002 | Snyder et al. | |
| 6,374,827 B1 | 4/2002 | Bowden et al. | |
| 6,390,996 B1 | 5/2002 | Halperin et al. | |
| 6,425,393 B1 | 7/2002 | Lurie et al. | |
| 6,439,228 B1 | 8/2002 | Hete et al. | |
| 6,459,933 B1 | 10/2002 | Lurie et al. | |
| 6,463,327 B1 | 10/2002 | Lurie et al. | |
| 6,486,206 B1 | 11/2002 | Lurie | |
| 6,526,970 B2 | 3/2003 | DeVries et al. | |
| 6,526,973 B1 | 3/2003 | Lurie et al. | |
| 6,536,432 B2 | 3/2003 | Truschel | |
| 6,544,172 B2 | 4/2003 | Toeppen-Sprigg | |
| 6,555,057 B1 | 4/2003 | Barbut et al. | |
| 6,578,574 B1 | 6/2003 | Kohnke | |
| 6,584,973 B1 | 7/2003 | Biondi et al. | |
| 6,587,726 B2 | 7/2003 | Lurie et al. | |
| 6,595,213 B2 | 7/2003 | Bennarsten | |
| 6,604,523 B2 | 8/2003 | Lurie et al. | |
| 6,622,274 B1 | 9/2003 | Lee et al. | |
| 6,622,724 B1 | 9/2003 | Truitt et al. | |
| 6,631,716 B1 | 10/2003 | Robinson et al. | |
| 6,656,166 B2 | 12/2003 | Lurie et al. | |
| 6,662,032 B1 | 12/2003 | Gavish et al. | |
| 6,676,613 B2 | 1/2004 | Cantrell et al. | |
| 6,729,334 B1 | 5/2004 | Baran | |
| 6,758,217 B1 | 7/2004 | Younes | |
| 6,776,156 B2 | 8/2004 | Lurie et al. | |
| 6,780,017 B2 | 8/2004 | Pastrick et al. | |
| 6,792,947 B1 | 9/2004 | Bowden | |
| 6,863,656 B2 | 3/2005 | Lurie | |
| 6,877,511 B2 | 4/2005 | DeVries et al. | |
| 6,935,336 B2 | 8/2005 | Lurie et al. | |
| 6,938,618 B2 | 9/2005 | Lurie et al. | |
| 6,986,349 B2 | 1/2006 | Lurie | |
| 6,988,499 B2 | 1/2006 | Holt et al. | |
| 7,011,622 B2 | 3/2006 | Kuyava et al. | |
| 7,032,596 B2 | 4/2006 | Thompson et al. | |
| 7,044,128 B2 | 5/2006 | Lurie et al. | |
| 7,066,173 B2 | 6/2006 | Banner et al. | |
| 7,082,945 B2 | 8/2006 | Lurie | |
| 7,096,866 B2 | 8/2006 | Be'eri et al. | |

(56) References Cited

U.S. PATENT DOCUMENTS

| | | |
|---|---|---|
| 7,174,891 B2 | 2/2007 | Lurie et al. |
| 7,185,649 B2 | 3/2007 | Lurie |
| 7,188,622 B2 | 3/2007 | Martin et al. |
| 7,195,012 B2 | 3/2007 | Lurie |
| 7,195,013 B2 | 3/2007 | Lurie |
| 7,204,251 B2 | 4/2007 | Lurie |
| 7,210,480 B2 | 5/2007 | Lurie et al. |
| 7,220,235 B2 | 5/2007 | Geheb et al. |
| 7,226,427 B2 | 6/2007 | Steen |
| 7,275,542 B2 | 10/2007 | Lurie et al. |
| 7,311,668 B2 | 12/2007 | Lurie |
| 7,469,700 B2 | 12/2008 | Baran |
| 7,487,773 B2 | 2/2009 | Li |
| 7,500,481 B2 | 3/2009 | Delache et al. |
| 7,594,508 B2 | 9/2009 | Doyle |
| 7,650,181 B2 | 1/2010 | Freeman et al. |
| 7,682,312 B2 | 3/2010 | Lurie |
| 7,766,011 B2 | 8/2010 | Lurie |
| 7,793,659 B2 | 9/2010 | Breen |
| 7,836,881 B2 | 11/2010 | Lurie et al. |
| 7,899,526 B2 | 3/2011 | Benditt et al. |
| 8,011,367 B2 | 9/2011 | Lurie et al. |
| 8,108,204 B2 | 1/2012 | Gabrilovich et al. |
| 8,151,790 B2 | 4/2012 | Lurie et al. |
| 8,210,176 B2 | 7/2012 | Metzger et al. |
| 8,388,682 B2 | 3/2013 | Hendricksen et al. |
| 8,408,204 B2 | 4/2013 | Lurie |
| 8,702,633 B2 | 4/2014 | Voss et al. |
| 8,755,902 B2 | 6/2014 | Lurie et al. |
| 8,939,922 B2 | 1/2015 | Strand et al. |
| 9,724,266 B2 * | 8/2017 | Voss .................... A61H 31/004 |
| 11,123,261 B2 * | 9/2021 | Voss .................... A61H 31/004 |
| 2001/0003984 A1 | 6/2001 | Bennarsten et al. |
| 2001/0029339 A1 | 10/2001 | Orr et al. |
| 2001/0047140 A1 | 11/2001 | Freeman |
| 2002/0007832 A1 | 1/2002 | Doherty |
| 2002/0069878 A1 | 6/2002 | Lurie et al. |
| 2002/0104544 A1 | 8/2002 | Ogushi et al. |
| 2002/0170562 A1 | 11/2002 | Lurie et al. |
| 2002/0179090 A1 | 12/2002 | Boussignac |
| 2003/0000526 A1 | 1/2003 | Gobel |
| 2003/0037782 A1 | 2/2003 | Yeung |
| 2003/0037784 A1 | 2/2003 | Lurie |
| 2003/0062040 A1 | 4/2003 | Lurie et al. |
| 2003/0062041 A1 | 4/2003 | Keith et al. |
| 2003/0192547 A1 | 10/2003 | Lurie et al. |
| 2004/0016428 A9 | 1/2004 | Lurie |
| 2004/0058305 A1 | 3/2004 | Lurie et al. |
| 2004/0200473 A1 | 10/2004 | Lurie et al. |
| 2004/0200474 A1 | 10/2004 | Lurie |
| 2004/0210281 A1 | 10/2004 | Dzeng et al. |
| 2004/0211415 A1 | 10/2004 | Lurie |
| 2004/0211416 A1 | 10/2004 | Lurie |
| 2004/0211417 A1 | 10/2004 | Lurie |
| 2004/0231664 A1 | 11/2004 | Lurie et al. |
| 2005/0016534 A1 | 1/2005 | Ost |
| 2005/0075531 A1 | 4/2005 | Loeb et al. |
| 2005/0126567 A1 | 6/2005 | Lurie |
| 2005/0165334 A1 | 7/2005 | Lurie |
| 2005/0199237 A1 | 9/2005 | Lurie |
| 2005/0217677 A1 | 10/2005 | Lurie et al. |
| 2005/0267381 A1 | 12/2005 | Benditt et al. |
| 2006/0089574 A1 | 4/2006 | Paradis |
| 2006/0094991 A1 | 5/2006 | Walker |
| 2006/0270952 A1 | 11/2006 | Freeman et al. |
| 2007/0017523 A1 | 1/2007 | Be-Eri et al. |
| 2007/0021683 A1 | 1/2007 | Benditt et al. |
| 2007/0060785 A1 | 3/2007 | Freeman et al. |
| 2007/0199566 A1 | 8/2007 | Be'eri |
| 2007/0221222 A1 | 9/2007 | Lurie |
| 2007/0277826 A1 | 12/2007 | Lurie |
| 2008/0039748 A1 | 2/2008 | Palmer et al. |
| 2008/0047555 A1 | 2/2008 | Lurie et al. |
| 2008/0092891 A1 | 4/2008 | Cewers |
| 2008/0097258 A1 | 4/2008 | Walker |
| 2008/0097385 A1 | 4/2008 | Vinten-Johansen et al. |
| 2008/0108905 A1 | 5/2008 | Lurie |
| 2008/0171311 A1 | 7/2008 | Centen et al. |
| 2008/0255482 A1 | 10/2008 | Lurie |
| 2008/0257344 A1 | 10/2008 | Lurie et al. |
| 2009/0020128 A1 | 1/2009 | Metzger et al. |
| 2009/0024175 A1 | 1/2009 | Freeman |
| 2009/0062701 A1 | 3/2009 | Yannopoulos et al. |
| 2009/0076573 A1 | 3/2009 | Burnett et al. |
| 2009/0164000 A1 | 6/2009 | Shirley |
| 2009/0234182 A1 * | 9/2009 | Buchholz .............. A61H 19/00 705/40 |
| 2009/0277447 A1 | 11/2009 | Voss et al. |
| 2009/0299156 A1 | 12/2009 | Simpson et al. |
| 2010/0000535 A1 | 1/2010 | Wickham et al. |
| 2010/0179442 A1 | 7/2010 | Lurie |
| 2010/0319691 A1 | 12/2010 | Lurie et al. |
| 2011/0056491 A1 | 3/2011 | Rumph et al. |
| 2011/0098612 A1 | 4/2011 | Lurie |
| 2011/0160782 A1 | 6/2011 | Lurie et al. |
| 2011/0201979 A1 | 8/2011 | Voss et al. |
| 2011/0297147 A1 | 12/2011 | Lick et al. |
| 2011/0319796 A1 * | 12/2011 | Campdera ......... A61H 23/0263 601/46 |
| 2012/0203147 A1 | 8/2012 | Lurie et al. |
| 2012/0330199 A1 | 12/2012 | Lurie et al. |
| 2012/0330200 A1 | 12/2012 | Voss et al. |
| 2013/0118498 A1 | 5/2013 | Robitaille et al. |
| 2013/0172768 A1 | 7/2013 | Lehman |
| 2013/0231593 A1 | 9/2013 | Yannopoulos et al. |
| 2013/0269701 A1 | 10/2013 | Lurie |
| 2014/0005566 A1 | 1/2014 | Homuth et al. |
| 2014/0048061 A1 | 2/2014 | Yannopoulos et al. |

FOREIGN PATENT DOCUMENTS

| | | |
|---|---|---|
| AU | 687942 B | 5/1995 |
| CA | 668771 A | 8/1963 |
| CA | 2077608 A1 | 3/1993 |
| CA | 2214887 A1 | 3/1995 |
| CN | 1183731 A | 6/1998 |
| DE | 2453490 A1 | 5/1975 |
| DE | 4308493 A1 | 9/1994 |
| EP | 0029352 A1 | 5/1981 |
| EP | 0139363 A1 | 5/1985 |
| EP | 0245142 A1 | 11/1987 |
| EP | 0367285 A2 | 5/1990 |
| EP | 0411714 A1 | 2/1991 |
| EP | 0509773 A1 | 10/1992 |
| EP | 0560440 A1 | 9/1993 |
| EP | 0623033 A1 | 11/1994 |
| GB | 1344862 | 1/1974 |
| GB | 1465127 | 2/1977 |
| GB | 2117250 A | 10/1983 |
| GB | 2139099 A | 11/1984 |
| JP | 2005675 A | 1/2005 |
| JP | 2006524543 A | 11/2006 |
| JP | 2007504859 A | 3/2007 |
| WO | 9005518 A1 | 5/1990 |
| WO | 9302439 A1 | 2/1993 |
| WO | 9321982 A1 | 11/1993 |
| WO | 9426229 A1 | 11/1994 |
| WO | 9513108 A1 | 5/1995 |
| WO | 9528193 A1 | 10/1995 |
| WO | 9628215 A1 | 9/1996 |
| WO | 9820938 A1 | 5/1998 |
| WO | 9947197 A1 | 9/1999 |
| WO | 9963926 A2 | 12/1999 |
| WO | 0020061 A1 | 4/2000 |
| WO | 0102049 A2 | 1/2001 |
| WO | 0170092 A2 | 9/2001 |
| WO | 0170332 A2 | 9/2001 |
| WO | 02092169 A1 | 11/2002 |
| WO | WO 02/091905 A2 * | 11/2002 |
| WO | 2004096109 A3 | 11/2004 |
| WO | 2006088373 A1 | 8/2006 |
| WO | 2008147229 A1 | 12/2008 |
| WO | 2010044034 A1 | 4/2010 |

(56) References Cited

FOREIGN PATENT DOCUMENTS

| | | |
|---|---|---|
| WO | 2013064888 A1 | 5/2013 |
| WO | 2013096495 A1 | 6/2013 |
| WO | 2014026193 A1 | 2/2014 |

OTHER PUBLICATIONS

Advanced Circulatory Systems, Inc. (2005). Introducing ResQPOD® (#49-0324-000, 01) [Brochure). Roseville, MN: Advanced Circulatory Systems, Inc., 2 pages.
Advanced Circulatory Systems, Inc. (2006). ResQPOD® Circulatory Enhancer: Strengthening the Chain of Survival (#49-0336-000, 02). [Brochure). Roseville.MN: Advanced Circulatory Systems, Inc., 2 pages.
Advanced Circulatory Systems, Inc. (2006). ResQPOD® Circulatory Enhancer: Strengthening the Chain of Survival (#49-0336-000, 01) [Brochure). Roseville, MN: Advanced Circulatory Systems, Inc. 2 pages.
Advanced Circulatory Systems, Inc. (2009). ResQPOD® Perfusion on Demand: ResQPOD Impedance Threshold Device (#49-0324-001, 02) [Brochure). Roseville, MN: Advanced Circulatory Systems, Inc., 2 pages.
Advanced Circulatory Systems, Inc. (2010), ResQPOD Impedance Threshold Device: Strengthening the Chain of Survival (#49-0336000,05) [Brochure], Roseville, MN:Advanced Circulatory Systems, Inc. 2 pages.
Advanced Circulatory Systems, Inc. (2010), ResQPOD Impedance Threshold Device: Strengthening the Chain of Survival (#49-0336000,04) [Brochure], Roseville, MN:Advanced Circulatory Systems, Inc. 2 pages.
Advanced Circulatory Systems, Inc. (2010), ResQPOD Impedance Threshold Device 10.0:Strengthening the Chain of Survival (#49-0336000,03) [Brochure], Roseville, MN: Advanced Circulatory Systems, Inc. 2 pages.
Advanced Circulatory Systems, Inc. (2010). ResQPOD® Perfusion on Demand: ResQPOD Impedance Threshold Device (#49-0324-001, 03) [Brochure). Roseville, MN: Advanced Circulatory Systems, Inc., 2 pages.
Advanced Circulatory Systems, Inc. (2011), ResQPOD ITD: Strengthening the Chain of Survival (#49-0336000,06) [Brochure], Roseville, MN: Advanced Circulatory Systems, Inc. 2 pages.
Advanced Circulatory Systems, Inc. (2011),Early Intervention is Life-Saving in Cardiac Arrest (#49-0864-000,01) [Brochure], Roseville, MN: Advanced Circulatory Systems, Inc. 2 pages.
Advanced Circulatory Systems, Inc. (2011),Early Intervention is Life-Saving in Cardiac Arrest (#49-0864-000,02) [Brochure], Roseville, MN: Advanced Circulatory Systems, Inc. 2 pages.
Advanced Circulatory Systems, Inc. (2011). ResQPOD® Perfusion on Demand: ResQPOD Impedance Threshold Device (#49-0324-001, 04) [Brochure). Roseville, MN: Advanced Circulatory Systems, Inc. 2 pages.
Advanced Circulatory Systems, Inc. (2011). ResQPOD® Perfusion on Demand: ResQPOD Impedance Threshold Device (#49-0324-001, 05) [Brochure). Roseville, MN: Advanced Circulatory Systems, Inc., 2 pages.
Advanced Circulatory Systems, Inc. (2012), Benefits of the ResQPOD Based Upon the ROC PRIMED Study (#49-0864-000,03) [Brochure], Roseville, MN: Advanced Circulatory Systems, Inc. 2 pages.
Advanced Circulatory Systems, Inc. (2012), Benefits of the ResQPOD Based Upon the ROC PRIMED Study (#49-0864-000,04) [Brochure], Roseville, MN: Advanced Circulatory Systems, Inc. 2 pages.
Advanced Circulatory Systems, Inc. (2013), Emerging Data: The Resuscitation Outcomes Consortium (ROC) PRIMED Study on the Efficacy of the ITD (#49-0864-000,05) [Brochure], Roseville, MN: Advanced Circulatory Systems, Inc. 2 pages.
Advanced Circulatory Systems, Inc. (2013), ResQPOD More than a Heartbeat (#49-0336-000,08) [Brochure], Roseville, MN: Advanced Circulatory Systems, Inc. 2 pages.
Advanced Circulatory Systems, Inc. (2014), Emerging Data: The Resuscitation Outcomes Consortium (ROC) PRIMED Study on the Efficacy of the ITD (#49-0864-000,06) [Brochure], Roseville, MN: Advanced Circulatory Systems, Inc. 2 pages.
Ambu InternationalNS Directions for use of Ambu® CardioPump™. •. Sep. 1992, 8 pages.
Aufderheide et al.,"Hyperventilation-induced hypotension during cardiopulmonary resuscitation", Circulation; 2004; pp. 1960-1965; vol. 109:16.
Aufderheide et al.; "Standard cardiopulmonary resuscitation versus active compression-decompression cardiopulmonary resuscitation with augmentation of negative intrathoracic pressure for out-of-hospital cardiac arrest: A randomized trial"; Lancet; 2011; pp. 301-311; vol. 377.
Babbs, "CPR Techniques that Combine Chest and Abdominal Compression and Decompression: Hemodynamic Insights from a Spreadsheet Model", Circulation, 1999, pp. 2146-2152.
Christenson; "Abdominal Compressions During CPR: Hemodynamic Effects of Altering Timing and Force", The Journal of Emergency Medicine, 1992; pp. 257-266; vol. 10.
Cohen et al., "Active Compression-Decompression: A New Method of Cardiopulmonary Resuscitation", JAMA; 1992; pp. 2916-2923; vol. 267:21.
Cohen et al.; "Active Compression-Decompression Resuscitation: a Novel Method of Cardiopulmonary Resuscitation", Department of Medicine and the Cardiovascular Research Institute, UC San Francisco, American Heart Journal; 1992; pp. 1145-1150; vol. 124:5.
Dupuis, Ventilators—Theory and Clinical Application, 1986; Mosby Company; pp. 447-448; vol. 481:496.
Edelson et al.; "Effects of compression depth and pre-shock pauses predict defibrillation failure during cardiac arrest"; Resuscitation; 2006; pp. 137-145; vol. 71.
Geddes et al., "Electrically Produced Artificial Ventilation," Medical Instrumentation, 1988; pp. 263-271; vol. 22:5.
Geddes et al., "Inspiration Produced by Bilateral Electromagnetic, Cervical Phrenic Nerve Stimulation in Man," IEEE Transactions on Biomedical Engineering; 1991; pp. 1047-1048; vol. 38:9.
Geddes et al., "Optimum Stimulus Frequency for Contracting the Inspiratory Muscles with chest Surface Electrodes to Produce Artificial respiration," Annals of Biomedical Engineering; 1990; pp. 103-108; vol. 18.
Geddes, "Electroventilation—A Missed Opportunity?", Biomedical Instrumentation & Technology, Jul./Aug. 1998, pp. 401-414.
Glenn et al., "Diaphragm Pacing by Electrical Stimulation of the Phrenic Nerve," Neurosurgery; 1985; pp. 974-984; vol. 17:6.
Glenn et al., "Twenty Years of Experience in Phrenic Nerve Stimulation to Pace the Diaphragm," Pace 9; Nov./Dec. 1986, pp. 780-784.
Guidelines for Cardiopulmonary Resuscitation and Emergency Cardiac Care, JAMA, 1992; pp. 2172-2177; vol. 268.
International Search Report and Written Opinion of PCT/US2011/024770 dated Apr. 6, 2011, 6 pages.
Kotze et al., "Diaphragm Pacing in the Treatment of Ventilatory Failure," San. Deel; 1995; pp. 223-224; vol. 68.
Laghi et al., "Comparison of Magnetic and Electrical Phrenic Nerve Stimulation in assessment of Diaphragmantic Contractility," American Physiological Society, 1996; pp. 1731-1742.
Lindner et al., "Effects of Active Compression-Decompression Resuscitation on Myocardialand Cerebral Blood Flow in Pigs," Department of Anesthesiology and Critical Care Medicine, University of Ulm, Germany, Circulation; 1993; pp. 1254-1263; vol. 88:3.
Lurie et al.; "Regulated to Death: The Matter of Informed Consent for Human Experimentation in Emergency Resuscitation Research"; Cardiac Arrhythmia Center at the University of Minnesota; PACE 18; Jul. 1995; pp. 1443-1447.
Lurie et al., Comparison of a 10-Breaths-Per-Minute Versus a 2-Breaths -Per-Minute Strategy During Cardiopulmonary Resuscitation in a Porcine Model of Cardiac Arrest,: Respiratory Care, 2008, vol. 53, No. 7, pp. 862-870.

(56) References Cited

OTHER PUBLICATIONS

Michigan Instruments, Inc. Thumper 1007CC Continuous Compression Cardiopulmonary Resuscitation System, obtained online 715/2006 at http://www.michiganinstruments.com/resus-thumper.htm, 2 pages.

Sato et al.; "Adverse effects of interrupting precordial compression during cardiopulmonary resuscitation"; Critical Care Medicine; 1997; pp. 733-736; vol. 25:5.

Schultz et al.; "Sodium nitroprusside enhanced cardiopulmonary resuscitation (SNPeCPR) improves vital organ perfusion pressures and carotid blood flow in a porcine model of cardiac arrest"; Resuscitation; 2012; pp. 374-377; vol. 83.

Segal et al.; "Ischemic Postconditioning at the Initiation of Cardiopulmonary Resuscitation Facilitates Cardiac and Cerebral Recovery After Prolonged Untreated Ventricular Fibrillation"; Resuscitation; 2012; 7 pages.

Shapiro et al., "Neurosurgical Anesthesia and Intracranial Hypertension" Chapter 54, Anesthesia; 3rd Edition; Ed. Ron Miller 1990.

Steen et al.; "The critical importance of minimal delay between chest compressions and subsequent defibrillation: a haemodynamic explanation"; Resuscitation; 2003; pp. 249-258; vol. 58.

Yannopoulos et al., "Intrathoracic Pressure Regulator During Continuous-Chest-Compression Advanced Cardiac Resuscitation Improves Vital Organ Perfusion Pressures in a Porcine Model of Cardiac Arrest", Circulation, 2005, pp. 803-811.

Yannopoulos et al.; "Controlled pauses at the initiation of sodium nitroprusside-enhanced cardiopulmonary resuscitation facilitate neurological and cardiac recovery after 15 minutes of untreated ventricular fibrillation"; Critical Care Medicine; 2012; 8 pages; vol. 40:5.

Yannopoulos et al.; "Intrathoracic Pressure Regulation Improves 24-Hour Survival in a Porcine Model of Hypovolemic Shock"; Anesthesia & Analgesia; ITPR and Survival in Hypovolemica Shock; Jan. 2007; pp. 157-162; vol. 24:1.

Yannopoulos et al.; "Intrathoracic pressure regulation improves vital organ perfusion pressures in normovolemic and hypovolemic pigs"; Resuscitation; 2006; pp. 445-453; vol. 70.

Yannopoulos et al.; "Sodium nitroprusside enhanced cardiopulmonary resuscitation improves survival with good neurological function in a porcine model of prolonged cardiac arrest"; Critical Care Medicine; 2011; 6 pages; vol. 39:6.

Yu et al.; "Adverse outcomes of interrupted precordial compression during automated defibrillation"; Circulation; 2002; pp. 368-372; vol. 106. IS X.

Zhao et al., Inhibition of a Myocardial Injury by Ischemic Postconditioning During RePerfusion: Comparison with Ischemic Preconditioning, Am. J. Physiol Heart Circ; 2003; pp. H579-H588; vol. 285.

Mushin et al., "Automatic Ventilation of the Lungs—The Lewis-Leigh Inflating Valve," Blackwell Scientific, Oxford, GB, 1980; p. 838.

Zoll Autopulse Non-Invasive Cardiac Support Pump, obtained online on Jul. 15, 2016 at http://www.zoll.com/product.aspx?id=84,1 page; 2009.

* cited by examiner

ENHANCED GUIDED ACTIVE COMPRESSION DECOMPRESSION CARDIOPULMONARY RESUSCITATION SYSTEMS AND METHODS

CROSS-REFERENCE TO RELATED APPLICATIONS

This application is a continuation of U.S. patent application Ser. No. 15/638,452, filed Jun. 30, 2017, which is a continuation of U.S. patent application Ser. No. 13/554,986, filed Jul. 20, 2012, which is a continuation-in-part of U.S. patent application Ser. No. 13/026,459, filed Feb. 14, 2011, which is a non-provisional of and claims the benefit of priority to U.S. Provisional Patent Application No. 61/304,148, filed Feb. 12, 2010. U.S. patent application Ser. No. 13/554,986 is also a continuation-in-part of U.S. patent application Ser. No. 13/175,670, filed Jul. 1, 2011, which is a non-provisional of and claims the benefit of priority to U.S. Provisional Patent Application Nos. 61/361,208, filed Jul. 2, 2010 and 61/485,944, filed May 13, 2011. U.S. patent application Ser. No. 13/554,986 is also a continuation-in-part of U.S. patent application Ser. No. 13/554,458, filed Jul. 20, 2012, which claims the benefit of priority to U.S. Provisional Application No. 61/509,994 filed Jul. 20, 2011. U.S. patent application Ser. No. 13/554,986 also claims the benefit of U.S. Provisional Application Nos. 61/509,994, filed Jul. 20, 2011 and 61/577,565 filed Dec. 19, 2011. The entire disclosure of each of the above referenced filings is incorporated herein by reference for all purposes.

BACKGROUND OF THE INVENTION

Embodiments of the present invention relate generally to systems and methods for active compression decompression (ACD) cardiopulmonary resuscitation (CPR), and in particular to guided approaches which assist an operator in administering appropriate technique in an effective manner.

Sudden cardiac arrest is a major cause of death worldwide and can arise from a variety of circumstances, including heart disease and trauma such as electrical shock and suffocation. To improve a patient's chance of survival (and diminish the likelihood of brain and heart damage resulting from oxygen deprivation), it is important that measures be taken as soon as possible to at least partially restore the patient's respiration and blood circulation. Many years ago, techniques for external chest compression, generally referred to as cardiopulmonary resuscitation (CPR), were developed and have enjoyed great success in reducing mortality resulting from sudden cardiac arrest. Certain aspects of such techniques, however, have remained largely unchanged over recent years.

External chest compression relies on actively applying pressure to the patient's chest in order to increase intrathoracic pressure. Such pressure increase will induce blood movement from the region of the heart and lungs through the peripheral arteries, thus partially restoring the patient's circulation. Phase 1 of traditional CPR is referred to as the "active compression phase" where the chest is compressed by the direct application of external pressure. Phase 2, referred to as the "relaxation phase," occurs when pressure is withdrawn and the natural elasticity of the patient's chest wall causes expansion. While such expansion is generally sufficient to refill the cardiac chambers with some blood, it is insufficient to ventilate the patient, i.e., fill the lungs with sufficient air to oxygenate the blood. Thus, conventional CPR further requires periodic ventilation of the patient, e.g., mouth-to-mouth ventilation, in order to provide the air necessary for blood oxygenation.

Manual CPR procedures generally require performers to lean over the patient and to apply pressure using the palms of their hands to the patient's sternum as the patient lies supine on a flat surface. If no one else is available, the performer must periodically shift position to ventilate the patient through a mouth-to-mouth procedure. Such manual procedures are thus very tiring to the performer and furthermore have been found to result in only marginal circulation.

Manual CPR procedures can also result in injury to the patient. For example, pressure applied by the palm of the hand can fracture the patient's sternum and/or ribs and cause other traumatic injury, especially if the performer's hand position is inadvertently shifted laterally to an improper location on the patient's chest. The performance and safety of CPR procedures can be enhanced through the use of various mechanical and automatic machines for applying external chest compression and optionally ventilating the patient by providing supplemental oxygen or air. The machines may be as simple as a "cardiac press" which is a manually operated lever which provides a mechanical advantage in performing chest compression. More sophisticated machines can provide chest compression and/or ventilation through a variety of other mechanisms, including the use of pressurized chambers for compressing the chest cavity. While such machines can be effective, their bulk, weight, and cost limit their availability. In particular, such machines are not widely available outside of medical facilities and their size is a deterrent to providing such equipment in emergency vehicles.

CPR is often administered in conjunction with other procedures which, taken together, are referred to as advanced cardiac life support (ACLS). Most commonly, CPR is administered while the patient undergoes both electrocardiographic monitoring (ECM) and electrical defibrillation. Although currently available CPR devices can provide real benefits to patients in need thereof, in some cases operator error or misuse may lead to ineffective treatment or patient injury. Hence, further advances would be desirable. For example, it would be desirable to provide improved systems and methods for guiding a system operator who may be involved with administering a treatment to a patient. Moreover, it would be desirable to provide systems and methods that help to ensure treatment is administered within desired or appropriate parameters. Embodiments of the present invention provide solutions that address the problems described above, and hence provide answers to at least some of these outstanding needs.

SUMMARY OF THE INVENTION

Embodiments of the present invention provide improved systems and methods for performing external chest compression, optionally in conjunction with CPR procedures. Such methods and systems provided enhanced ventilation and blood circulation in the patient undergoing treatment, preferably reducing or eliminating the need to separately ventilate the patient. Desirably, the methods and systems can be simple and easily stored so that they can be maintained in emergency vehicles, non-medical facilities, and even the home. The systems can be suitable for performing enhanced manual CPR, in particular by converting, Phase 2 chest expansion from a passive event to an active process to improve venous blood return from the heart and enhance airflow into the lungs (facilitated ventilation). Systems can provide guidance to operators or technicians, such as digital outputs showing the amount of force to be applied to a patient during a chest compression or decompression. Further, systems may include handle configurations which ensure appropriate forces are applied to the patient.

Chest compression or decompression systems according to embodiments of the present invention also provide a device contact area or adhesive pad that is 2 to 4 times larger than the compressive area. Such configurations can allow an operator to physically lift or decompress a large surface area of the patient's chest. Relatedly, such large surface contact areas can make it easier for an operator or user to generate a full or greater decompression, thus resulting in more blood flow back to the heart. What is more, embodiments of the present invention provide compression surface areas which are sufficiently large to confer enhanced coronary perfusion pressure or increased blood flow from the heart to other organs or tissue during compression.

Systems and methods disclosed herein can be used for actively compressing and expanding an area of the human body, such as the thoracic cavity or chest, the abdomen, the back, and the like. Embodiments are useful for treating a variety of ailments wherein such compression and expansion may be beneficial; for example, heart failure, cardiac arrest, low blood pressure, poor blood circulation, shock and other maladies affecting internal organs such as the heart, stomach, intestines, liver, spleen, pancreas, and the like. In some cases, embodiments may be particularly useful for lowering or otherwise altering intrathoracic pressure (ITP) and for ventilating patients who are not breathing. An exemplary embodiment provides devices and methods for actively compressing and decompressing the thoracic cavity in the performance of cardiopulmonary resuscitation (CPR) and advanced cardiac life support (ACLS) procedures.

In one aspect, embodiments of the present invention encompass systems and methods for applying guided active compression decompression cardiopulmonary resuscitation to an individual by an operator. Exemplary systems include a compression element that is pressed and lifted by the operator, a flexible surface element coupled with the compression element and removably attachable to a chest area of the individual, an operator interface that provides guidance to the operator as to how to perform chest compressions, and a processor operably coupled with the operator interface. Systems may also include a memory that is configured to store instructions executable by the processor to provide a set of operator instructions to perform a first conditioning protocol for increasing circulation in the individual by compressing the chest in a repeated manner for a certain number of chest compressions or for a first time duration, a second conditioning protocol for pausing or reducing circulation in the individual following the first conditioning protocol by stopping chest compressions for a certain time duration, and a third conditioning protocol for increasing circulation in the individual following the second protocol by again compressing the chest in a repeated manner for a certain number of chest compressions or for a third time duration. In some instances, each of the first and third conditioning protocols include a series of periodic active chest compressions and decompressions. In some instances, each of the first and third conditioning protocol include a duration, and the first conditioning protocol duration is different from the third conditioning protocol duration. In some cases, each of the first and third conditioning protocol include a duration, and the first conditioning protocol duration is equal to the third conditioning protocol duration. In some instances, the first conditioning protocol includes a duration of about 40 seconds, the duration of the second conditioning protocol is about 20 seconds, and the third conditioning protocol includes a duration of about 20 seconds or about 40 seconds. In some instances, the operator interface includes a display subsystem that provides at least a portion of the guided treatment instructions. In some instances, the operator interface includes an audio output device that provides at least a portion of the guided treatment instructions. In some instances, the audio output device includes a loudspeaker. In some instances, the operator interface includes a tactile output device that provides at least a portion of the guided treatment instructions. In some instances, the tactile output device includes a vibration mechanism. In some instances, the operator interface includes a display subsystem and an audio output device that provide at least a portion of the guided treatment instructions. In some instances, systems may also include a means for delivering an electrical defibrillation or shock treatment to the individual. In some instances, the set of operator instructions is based at least in part on a physiological parameter of the patient. In some instances, the physiological parameter of the patient is a ventilation rate, a body temperature, a heart rate, a respiratory rate, a vital sign, an end tidal carbon dioxide measure, or any combination thereof. In some cases, systems may also include a pressure regulator mechanism that modulates pressure within an airway of the individual. In some instances, the memory is configured to store instructions executable by the processor to receive information indicating whether the operator is following the set of operator instructions and to provide a signal indicating whether the operator is following the set of operator instructions. In some instances, the memory is configured to store instructions executable by the processor to receive information indicating whether the individual has previously received a CPR treatment.

In another aspect, embodiments of the present invention encompass systems and methods for providing guidance to an operator for administering a chest compression treatment to an individual. Exemplary systems may include a module that stores or receives treatment information, and an operator interface that provides a set of instructions to the operator based on the treatment information. The set of instructions may include a first conditioning protocol for increasing circulation in the individual, the first conditioning protocol including compressing the chest in a repeated manner for a certain number of chest compressions or for a first time duration, a second conditioning protocol for pausing or reducing circulation in the individual following the first conditioning protocol, the second conditioning protocol including ceasing chest compressions, and a third conditioning protocol for increasing circulation in the individual following the second protocol, the third protocol including again compressing the chest in a repeated manner. In some instances, each of the first and third conditioning protocols include a series of periodic active chest compressions and decompressions. In some instances, each of the first and third conditioning protocols include a duration, and the first conditioning protocol duration is different from the third conditioning protocol duration. In some instances, each of the first and third conditioning protocol comprise a duration, and the first conditioning protocol duration is equal to the third conditioning protocol duration. In some instances, each of the first and third conditioning protocol comprise a duration, and the first conditioning protocol duration is greater than the third conditioning protocol duration.

In another aspect, embodiments of the present invention encompass systems and methods for administering a chest compression treatment to an individual. Exemplary methods include providing audio and/or visual and/or tactile instructions for performing repeated chest compressions on the individual. Some exemplary methods may include performing a first conditioning protocol for increasing circulation in the individual based on the instructions, where the first conditioning protocol includes compressing the chest in a repeated manner for a certain number of chest compressions or for a certain time duration, performing a second conditioning protocol for pausing or reducing circulation in the individual following the first conditioning protocol based on the instructions, where the second conditioning protocol includes ceasing chest compressions, and performing a third conditioning protocol for increasing circulation in the individual following the second protocol based on the instructions, where the third protocol includes again compressing the chest in a repeated manner. In some instances, the first conditioning protocol includes a series of periodic active chest compressions and decompressions. In some instances, the third conditioning protocol includes a series of periodic active chest compressions and decompressions. In some instances, each of the first and third conditioning protocols includes a series of periodic active chest compressions and decompressions. In some instances, methods further include delivering an electrical defibrillation treatment to the individual. In some instances, methods further include modulating a pressure within an airway of the individual.

In yet another aspect, embodiments of the present invention encompass systems for applying guided active compression decompression cardiopulmonary resuscitation to an individual by an operator. Exemplary systems may include a compression element that is pressed and lifted by the operator, a flexible surface element coupled with the compression element and removably attachable to a chest area of the individual, an operator interface that provides guidance to the operator as to how to perform chest compressions, and a processor operably coupled with the operator interface. Systems may also include a memory that is configured to store instructions executable by the processor to provide a set of operator instructions to perform a first conditioning protocol for increasing circulation in the individual by compressing the chest in a repeated manner for a first time duration, a second conditioning protocol for pausing or reducing circulation in the individual following the first conditioning protocol by stopping chest compressions for a second time duration, and a third conditioning protocol for increasing circulation in the individual following the second protocol by again compressing the chest in a repeated manner for a third time duration. In some instances, the first time duration is about 40 seconds. In some instances, the second time duration is about 20 seconds. In some instances, the third time duration is about 20 seconds. In some instances, the set of operator instructions further includes instructions to perform a fourth conditioning protocol following the third conditioning protocol, the fourth conditioning protocol including stopping chest compressions for a fourth time duration. In some instances, the fourth time duration is about 20 seconds. In some instances, the set of operator instructions further includes instructions to perform a fifth conditioning protocol following the fourth conditioning protocol, the fifth conditioning protocol including compressing the chest in a repeated manner for a fifth time duration. In some instances, the fifth time duration is about 20 seconds. In some instances, the set of operator instructions further includes instructions to perform a sixth conditioning protocol following the fifth conditioning protocol, the sixth conditioning protocol including stopping chest compressions for a sixth time duration. In some instances, the sixth time duration is about 20 seconds. In some instances, the set of operator instructions further includes instructions to perform a seventh conditioning protocol following the sixth conditioning protocol, the seventh conditioning protocol including compressing the chest in a repeated manner for a seventh time duration. In some instances, the seventh time duration is within a range from about 0 seconds to about 60 seconds. In some instances, the set of operator instructions further includes instructions to administer a vasopressor agent to the individual. In some instances, the set of operator instructions further includes instructions to administer a vasodilator agent to the individual. In some instances, the set of operator instructions further includes instructions to administer an electrical shock to the individual. In some instances, the set of operator instructions further includes instructions to assess one or more physiological parameters of the individual. In some instances, the set of operator instructions further includes instructions to assess one or more physiological parameters of the individual and instructions to administer an electrical shock based on the assessed physiological parameter or parameters. In some instances, systems include an input mechanism or button for receiving an indication from the operator as to whether the individual has previously received CPR. In some instances, the set of operator instructions further include instructions to not administer a stutter CPR therapy.

In one aspect, embodiments of the present invention encompass systems and methods for ACD CPR. An exemplary system for applying guided active compression decompression cardiopulmonary resuscitation to an individual in need thereof can include, for example, a handle, a load cell in operative association with the handle, and an adhesive pad. The handle and the adhesive pad can be configured for releasable coupling. In some cases, the handle and the adhesive pad are configured for releasable magnetic coupling. In some cases, a handle of an ACD CPR system can be coupled with a drive element of an automated reciprocating system. In some cases, an ACD CPR system may include or be used in conjunction with an intrathoracic pressure regulator (ITPR) system that modulates pressure within an airway of the individual.

In another aspect, embodiments of the present invention provide systems and devices for actively compressing and expanding an area of the body. A device can include a compression element that is configured to be pressed and lifted, and a flexible surface element operably coupled with the compression element and configured to be removably attached to a body part over a contact area. In some cases, the compression element is adapted to apply a compressive force to the body part through the surface element over a compressive area when the compression element is pressed. The contact area can be sized to be at least twice as large as the compressive area. In some cases, the contact area can be sized to be in the range of two to three times as large as the compressive area. Optionally, the surface element can be a generally planar flexible contact pad the lower surface of which defines the contact area. In some instances, the lower surface of the contact pad includes an adhesive material. In some cases, the compression element includes a dome-shaped handle disposed on the top end of a centrally-located rigid connecting stem. Optionally, the bottom end of the connecting stem can be connected to the top surface of a generally planar flexible contact pad and define the compressive area. The handle can include a dome-shaped upper surface and an annular planar lower surface surrounding the top end of the connecting stem, and the upper surface and lower surface can be separated by a peripheral flange. In some cases, a device includes at least one measuring element associated with the contact pad. A measuring element can be configured to measure a physiological parameter of the patient. A device may also include a display element associated with the contact pad. In some cases, the display element is configured to provide patient feedback information. A device may also include at least one electrode associated with the surface element for applying electricity to the body part. In some cases, a device includes means associated with the surface element for applying a drug. Optionally, a device may include at least one sensor associated with the surface element. In some instances, a device may include at least one reference element associated with the surface element to aid in the proper placement of the surface element on the body part.

In another aspect, embodiments provide systems and methods for increasing and reducing intrathoracic pressure wherein a flexible contact pad is removably attached to a patient's chest over a contact area, and a handle configured to be pressed and lifted is operably connected to the contact pad so that pressing down of the handle applies a compressive force over a compressive area to compress the chest, and lifting up of the handle applies a lifting force over the contact area to expand the chest. In some cases, the contact area is sized to be at least twice as large as the compressive area. Optionally, the contact area is sized to be from 2 to 3 times as large as the compressive area.

In still another aspect, embodiments of the present invention encompass systems and methods for compressing and expanding a body part that include, for example, providing a compression element that is configured to be pressed so as to apply a compressive force over a compressive area, operably coupling the compression element with a flexible surface element having a top surface including the compressive area and a bottom surface, removably attaching the bottom surface of the surface element to a body part to define a contact area that is at least twice as large as the compressive area, pressing the compression element against the surface element to compress the body part over the compressive area, and lifting the surface element to actively expand the body part over the contact area. In some cases, the surface element is a contact pad attached to a patient's chest with adhesive. In some cases, the compression element is a handle that is pressed and lifted by hand. Optionally, the contact area is sized to be in the range of two to three times as large as the compressive area.

In still another aspect, embodiments of the present invention encompass systems and methods and devices for the performance of volume exchange CPR, wherein during the compression of the chest the pressure inside the thorax rises and blood is propelled forward out of the heart and lungs to the brain and other organs outside the thorax. At the same time respiratory gases are pushed out of the lungs as the lungs are compressed. During the decompression phase the anterior chest wall is lifted upward and at the same time respiratory gases are prevented or inhibited from entering the lungs by transiently blocking or occluding the airway. By preventing or inhibiting respiratory gases from entering the lungs during the decompression phase of the thorax, more blood volume is drawn into the thorax, into the heart and lungs, in exchange for the volume of respiratory gas that was pushed out of the lungs on the prior compression and not allowed back into the lungs by occluding the airway. The means to occlude the airway could be a one-way valve or preferably a valve system that allows for the rescuer to ventilate the patient. One way to ventilate the patients would be to periodically provide a positive pressure ventilation through or around the one-way valve. Thus, volume exchange CPR allows for blood flow out of the heart or the brain during the compression phase, and allows for more blood, rather than respiratory gases, to enter the lungs during the decompression phase. In one aspect of volume exchange CPR, respiratory gases could be actively removed from the lungs with a low-level vacuum that could be continuous or intermittent, during CPR. In another aspect of volume exchange CPR respiratory gases could be actively withdrawn from the lungs and then a positive pressure breath could be delivered, with or without a period of positive end-expiratory pressure before or after the positive pressure ventilation.

In another aspect, embodiments of the present invention encompass systems and methods for applying guided active compression decompression cardiopulmonary resuscitation to an individual in need thereof. Exemplary systems may include a handle, a measuring assembly in operative association with the handle, and an adhesive pad. The handle and the adhesive pad can be configured for releasable coupling. In some cases, the measuring assembly includes a force measuring device. In some cases, the measuring assembly includes a distance measuring device. In some cases, the measuring assembly includes a force and distance measuring device. Optionally, a force and distance measuring device may include an accelerometer.

In another aspect, embodiments of the present invention encompass automated systems for applying guided active compression decompression cardiopulmonary resuscitation to an individual in need thereof. Exemplary systems may include an automated compression decompression generation assembly, a measuring assembly in operative association with the automated compression decompression generation assembly, and an adhesive pad. The automated compression decompression generation assembly and the adhesive pad can be configured for releasable coupling.

In another aspect, embodiments of the present invention encompass systems and methods for applying guided active compression decompression cardiopulmonary resuscitation to an individual in need thereof. Exemplary systems may include a handle, a measuring assembly in operative association with the handle, and an adhesive pad. The handle and the adhesive pad can be configured for releasable coupling via a mechanical interlock. In some instances, the mechanical interlock includes a ball and socket assembly. Optionally, a mechanical interlock can include a cantilevered arm assembly. In some cases, the mechanical interlock includes a detent mechanism assembly.

In some aspects, embodiments of the present invention encompass systems and methods for providing a volume exchange cardiopulmonary resuscitation treatment to a patient. Exemplary methods may include compressing the patient's chest during a compression phase, and lifting upward the patient's anterior chest wall and occluding the patient's airway during a decompression phase. Relatedly, systems may include means for compressing the patient's chest during a compression phase, and for lifting upward the patient's anterior chest wall and occluding the patient's airway during a decompression phase. In some cases, the step of occluding the patient's airway includes occluding the airway with a one way valve. In some cases, the step of occluding the patient's airway includes occluding the airway with a valve system that allows an operator to ventilate the patient. Optionally, methods may include ventilating the patient with the valve system. In some cases, methods may include ventilating the patient by provide a positive pressure ventilation through or around the one-way valve. Methods may also include actively removing respiratory gases from the patient's lungs with a low-level vacuum. Relatedly, systems may include means for providing a low-level vacuum. In some instances, the low-level vacuum is continuous. In some instances, the low-level vacuum is intermittent. Some methods may include actively withdrawing respiratory gases from the patient's lungs, and subsequently delivering a positive pressure breath to the patient. Related systems may include means for actively withdrawing respiratory gases from the patient's lungs, and for subsequently delivering a positive pressure breath to the patient. In some cases, the positive pressure breath is delivered with a period of positive end-expiratory pressure, either before or after the positive pressure ventilation.

In still another aspect, embodiments of the present invention include systems and methods for providing a volume exchange cardiopulmonary resuscitation treatment to a patient. Exemplary systems may include a compression element that is configured to be pressed and lifted, a flexible surface element operably coupled with the compression element and configured to be removably attached to a body part, and an occlusion mechanism for occluding the patient's airway during a decompression phase. In some instances, the occlusion mechanism includes a one way valve. In some instances, the occlusion mechanism includes a valve system that allows an operator to ventilate the patient. In some instances, systems may include a vacuum source for actively removing respiratory gases from the patient's lungs with a continuous or intermittent low level vacuum.

In another aspect, embodiments of the present invention encompass systems and methods for actively compressing and expanding an area of the body. Exemplary devices may include a compression element that is configured to be pressed and lifted, a flexible surface element operably coupled with the compression element and configured to be removably attached to a body part, an interface for displaying information to and receiving information from an operator, a processor coupled with the interface, and a memory coupled with the processor. The memory can be configured to store a plurality of code modules for execution by the processor. The plurality of code modules can include a module for recording a compression event history, a module for storing the compression event history, a module for assessing a cardiopulmonary resuscitation quality factor, and a module for providing feedback to the operator based on the cardiopulmonary resuscitation quality factor.

In still another aspect, embodiments of the present invention encompass systems and methods for actively compressing and expanding an area of the body. Exemplary devices may include a compression element that is configured to be pressed and lifted, a flexible surface element operably coupled with the compression element and configured to be removably attached to a body part, an interface for displaying instructions to an operator, a processor coupled with the interface, and a memory coupled with the processor. The memory can be configured to store a plurality of code modules for execution by the processor. The plurality of code modules can include a module for providing operator instructions to perform a number of compressions prior to initiating active compression and decompression.

In still a further aspect, embodiments of the present invention encompass systems and methods for treating a patient. Exemplary methods may include providing a compression element that is configured to be pressed so as to apply a compressive force to the patient's chest, operably coupling the compression element with a flexible surface element having a top surface and a bottom surface, removably attaching the bottom surface of the surface element to the patient's chest, attaching a lower compression device to at least a portion of a lower extremity of the patient, repetitively pressing the compression element against the surface element to compress the patient's chest and lifting the surface element to actively expand the patient's chest, so that the patient's chest experiences a compression phase and a recoil phase, and compressing the person's lower extremity using the lower compression device during at least some of the recoil phases.

For a fuller understanding of the nature and advantages of the present invention, reference should be had to the ensuing detailed description taken in conjunction with the accompanying drawings.

DESCRIPTION OF THE INVENTION

Figure 1:
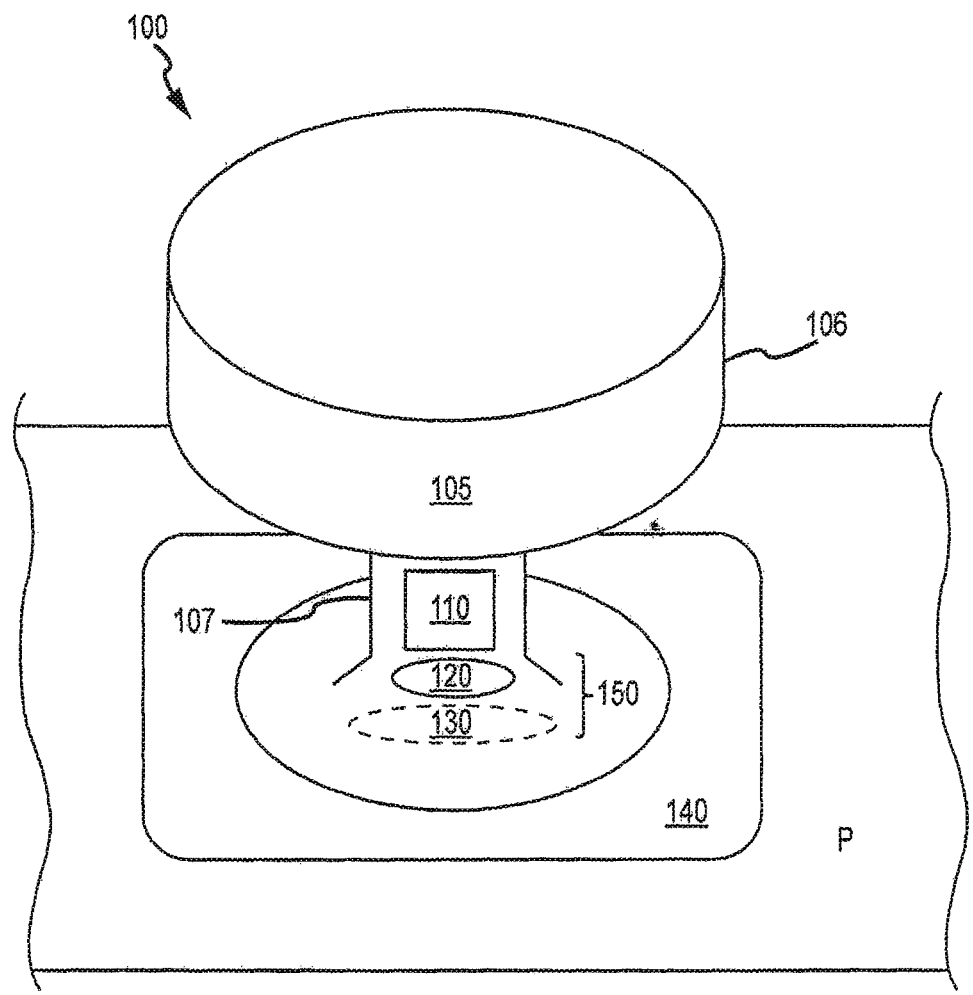
FIG. 1 illustrates aspects of an ACD CPR system according to embodiments of the present invention.

Systems and methods are provided for performing manual and automated cardiopulmonary resuscitation (CPR), optionally in combination with electrocardiographic monitoring (ECM) and/or electrical defibrillation as part of advanced cardiac life support (ACLS) procedures. However, it will be recognized by one skilled in the art that embodiments of the present invention may also find other uses wherein compression and expansion of a body part or body area is required or beneficial, optionally in combination with decompression maneuvers. Therefore, the invention is not intended be limited to the specific embodiments described herein.

System and method embodiments provided herein are well suited for administering enhanced ACD CPR and ACLS procedures. Exemplary systems include a disposable adhesive pad which sticks to the chest of the patient, a detachable handle that detaches from the adhesive pad when excessive decompression force (upward pull) is applied, and a display which indicates to the operator the appropriate amount of force to be applied. Moreover, systems can be configured or customized for use on a particular individual based on body weight or size, for example. In some cases, systems and methods can be used by rescuers to perform ACD CPR on patients in cardiac arrest, or in patients showing a lack of signs of circulation.

ACD CPR systems and techniques provided herein can enable a rescuer or operator to perform ACD CPR, which differs from standard CPR in that it actively re-expands (decompresses) the chest after each compression. This approach allows the operator to use the same body position and compression technique as in standard CPR. Active chest decompression is achieved when the rescuer maintains a firm grip on the ACD CPR system and swings his or her body weight upwards after compression. A single-use disposable adhesive pad can be applied to the chest and transfers the lifting force to the lower part of the ribcage. Compression force is transferred to the chest as in standard CPR via the device's piston and compression pad. A force gauge in the handle assists the rescuer in applying the force needed to achieve desired compression (e.g. 1½ to 2 inches), and the lift necessary for adequate decompression. A visual metronome can guide the rescuer to compress and decompress at the appropriate rate and force.

In use, the operator can attach the system with the patient's chest via the adhesive pad, and apply compressive and decompressive forces to the patient by maneuvering the system handle. For example, the operator can press downwardly on the handle with a sufficient force so as to compress the patient's chest and induce blood circulation from the chest. The operator can then pulls upwardly on the handle so that the adhesive pad actively expands the patient's chest to induce blood circulation into the chest and ventilate the patient's lungs. The downward and upward strokes can be repeated at a rate sufficient to maintain blood circulation and enhance ventilation, typically with a compression distance in the range from about 3.5 cm to about 5 cm and a rate in the range from about 60 repetitions to about 100 repetitions per minute. This technique may be particularly effective when the operator kneels beside the patient and grasps the handle with fully-extended arms, with the operator's palms engaging the upper surface of the handle and fingers grasped around the peripheral flange of the handle. The operator may then apply the necessary or desired downward and upward strokes with fully-extended, locked arms while holding the system in a very stable configuration.

Turning now to the drawings, FIG. 1 illustrates aspects of an ACD CPR system according to embodiments of the present invention. The stem 107 of the system handle 105 contains a load cell 110 that measures the compression and decompression forces applied to the patient P. In some embodiments, a load cell 110 which measures the compression and decompression forces is in compression during its resting state. Accordingly, the load cell 110 can provide measurements for both upward and downward forces. The handle 105 can be designed to provide a convenient grip 106 that transfers compression via the heels of the hand and lift via the fingers. Hence, no change of grip may be needed between compression and decompression. The system 100 may be configured so that the handle 105 is automatically positioned by magnets 120, 130 when the handle 105 comes into contact with the adhesive pad 140. According so some embodiments, system 100 may include a detachable magnetic connection mechanism 150 disposed between the handle 105 and the adhesive pad 140. The connection mechanism 150 can be configured so that the handle 105 decouples from the adhesive pad 140 on the chest when the decompression force exceeds a predetermined limit. For example, the handle 105 may become unattached at a pull force of 25 lbs, thereby not allowing the user to pull up with more than 25 lbs force. Furthermore, the handle 105 can be easily attached to the adhesive pad 140 when it is brought close to the pad 140 via the magnetic interlock or connection mechanism 150.

Figure 1A:
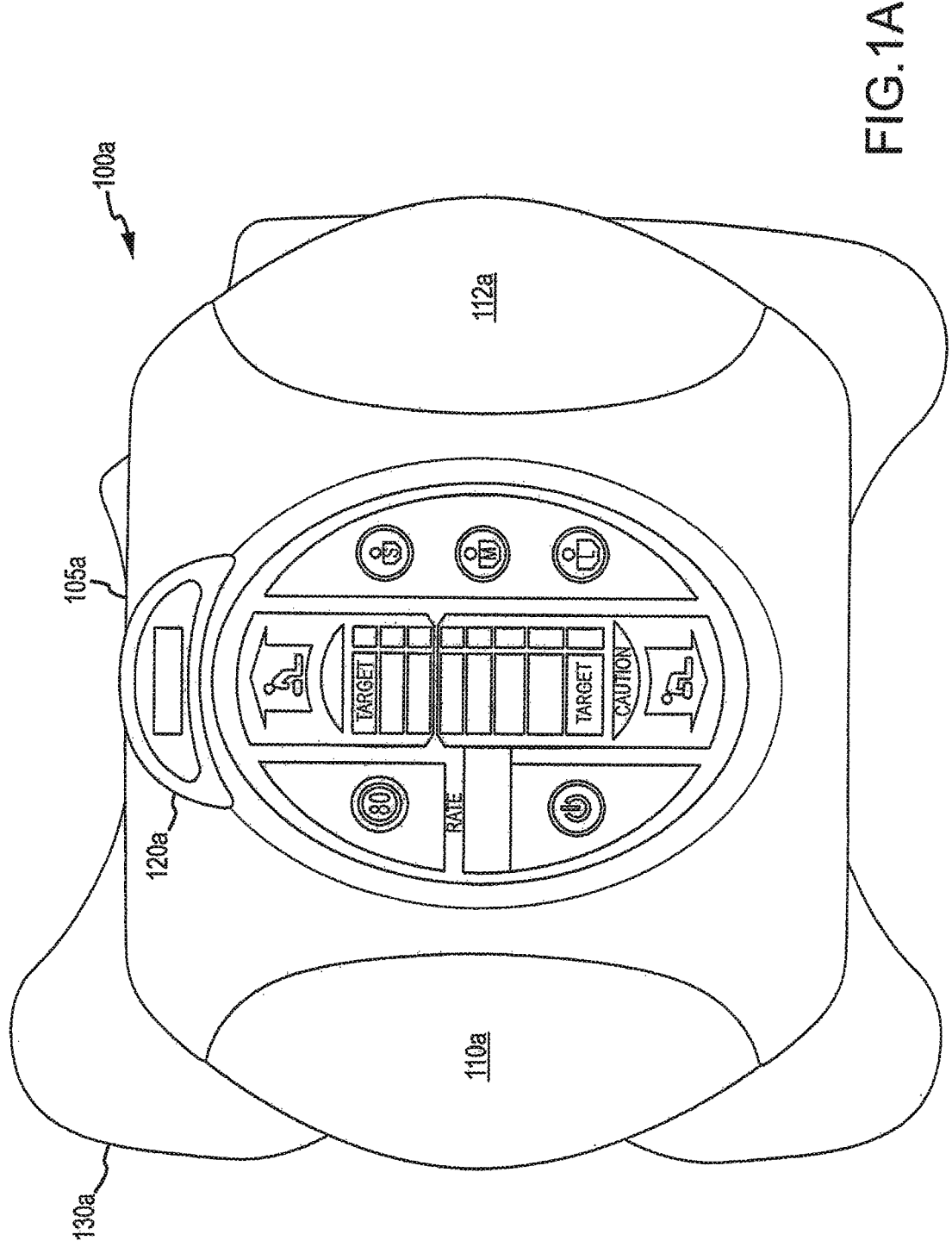
FIGS. 1A and 1B illustrate aspects of ACD CPR systems according to embodiments of the present invention.

FIG. 1A provides a top view of an ACD CPR system 100 a according to embodiments of the invention. System 100 a includes a handle 105 a having two handgrips 110 a, 112 a and a graphical user interface 120 a. Handle 105 a is intended for multiple uses and is easily attached and removed from an adhesive pad 130 a. In some cases, adhesive pad 130 a is disposable. For example, in use the adhesive pad may be applied to a patient during an ACD CPR procedure, and discarded following the treatment. Handle 105 a may be attached with adhesive pad 130 a via a magnet. In some instances, the magnetic coupling is configured such that handle 105 a becomes detached from adhesive pad 130 a when excessive decompression force (upward pull) is applied. Other means to couple the handle to the adhesive pad include various mechanical connections including ball and socket, cantilevered arm, or detent mechanism or the like.

Figure 1B:
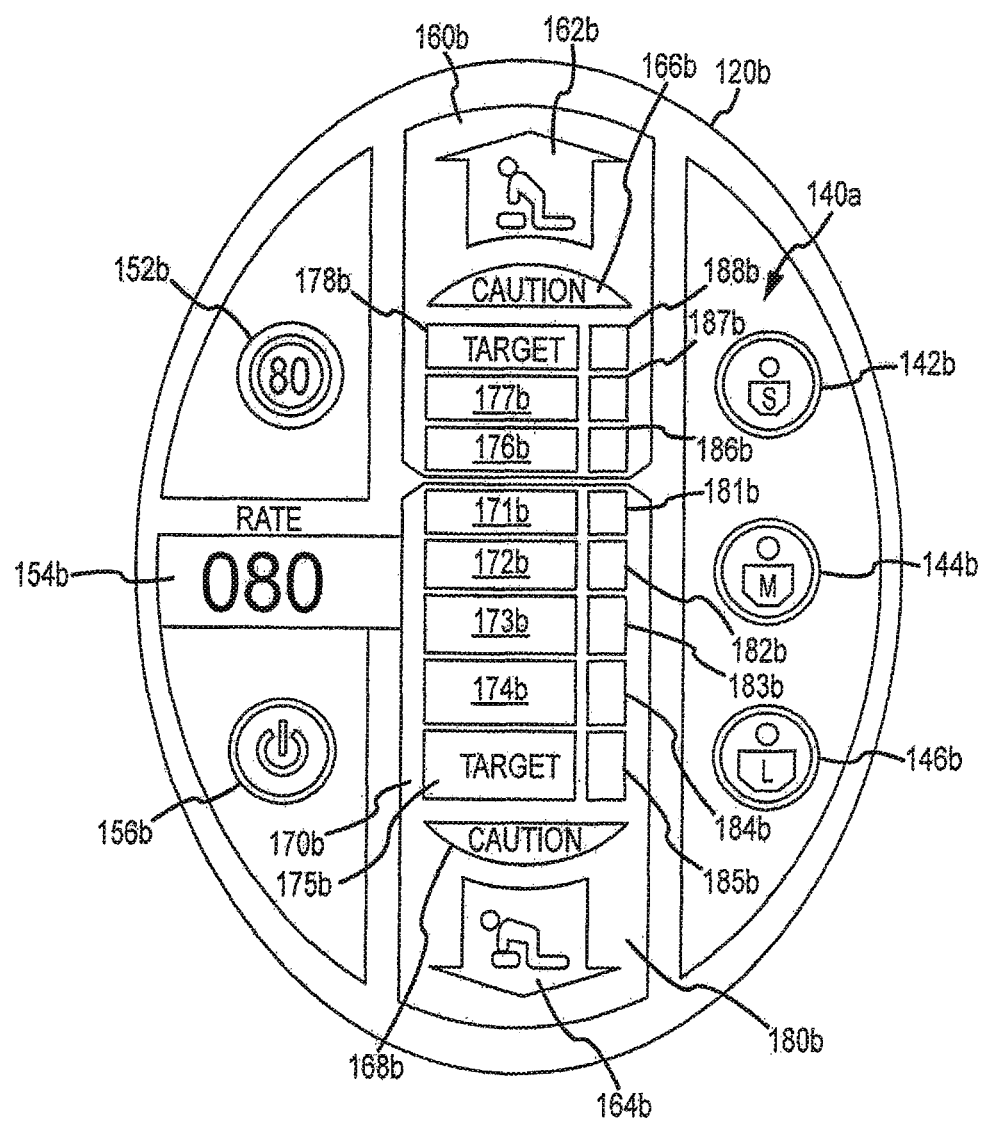

FIG. 1B depicts an exemplary graphical user interface (GUI) 120 b according to embodiments of the present invention. As shown here, GUI 120 b includes a body size input 140 b having a small body size selection 142 b, a medium body size selection 144 b, and a large body size selection 146 b. These three inputs or buttons allow a user to select the patient chest size or stiffness. GUI 120 b also includes a target compression/decompression numerical rate display 152 b, an actual or applied compression/decompression numerical rate display 154 b, and a power indicator or button 156 b. Target rate display 152 b can be configured to provide a numerical display or output of the desired or appropriate compression rate, decompression rate, or both. Actual rate display 154 b can be configured to provide a numerical display of the actual or applied compression rate, decompression rate, or both. Further, GUI 120 b includes a force application display 160 b that includes a force guide 170 b and a force display 180 b.

Force guide 170 b provides an indication or guide to the operator of how hard to push during a chest compression, how hard to pull during a chest decompression, and how fast to push and pull while administering the compressions and decompressions. For example, in some cases the system may determine that a compression force of 100 lbs and a decompression force of 20 lbs should be applied during the treatment, at a rate of 120 compressions per minute. Table 1 shows an exemplary set of prescribed compression and decompression forces associated with indicator bars of force guide 170 b, for such treatment parameters. During the compression and decompression phases of the cycle, indicator bars 171 b-178 b light up or activate in sequence at the prescribed rate, to provide the operator with a visual guide of how forcefully and how quickly to administer the compressions and decompressions.

TABLE 1

| Indicator Bar | Force | Time |
|---|---|---|
| ACD CPR cycle (compression) | | |
| 171b | 20 lbs | 0.025 seconds |
| 172b | 40 lbs | 0.050 seconds |
| 173b | 60 lbs | 0.075 seconds |
| 174b | 80 lbs | 0.100 seconds |
| 175b (compression target) | 100 lbs | 0.125 seconds |
| 174b | 80 lbs | 0.150 seconds |
| 173b | 60 lbs | 0.175 seconds |
| 172b | 40 lbs | 0.200 seconds |
| 171b | 20 lbs | 0.225 seconds |
| | 0 lbs | 0.250 seconds |
| ACD CPR cycle (decompression) | | |
| 176b | 6.7 lbs | 0.292 seconds |
| 177b | 13.4 lbs | 0.333 seconds |
| 178b (decompression target) | 20 lbs | 0.375 seconds |
| 177b | 13.4 lbs | 0.416 seconds |
| 176b | 6.7 lbs | 0.458 seconds |
| | 0 lbs | 0.500 seconds |

Ventilations can be provided to the patient, for example according to current American Heart Association recommendations. In some cases, ventilations can be administered to the patient at a compression-ventilation ratio of about 30:2 (i.e. 30 chest compressions given for every two rescue breaths).

Force display 180 b provides an indication of how hard the operator is actually pushing during the compression phase and pulling during the decompression phase, and how fast the operator is pushing and pulling when administering the compressions and decompressions. For example, during the compression and decompression phases of the cycle, indicator bars 181 b-188 b light up or activate depending on how forcefully and how quickly the operator administers the compressions and decompressions. Accordingly, force display 180 b enables the operator to track or visualize his or her actual applied force and rate, and compare the applied force and rate with the target force and rate as provided by force guide 170 b. By using force guide 170 b as a target reference and force display 180 b as an indication of the efforts applied during treatment, the operator can realize or approach the goal of matching the applied forces and rates with the target forces and rates.

Force application display 160 b also includes a decompression indicator 162 b, a compression indicator 164 b, a decompression limit warning indicator 166 b, and a compression limit warning indicator 168 b. According to the embodiment depicted here, decompression indicator 162 b provides the user with a reference or indication that force guide 170 b and force display 180 b signals displayed toward the top of GUI 120 b are associated with the decompression phase of ACD CPR. Likewise, compression indicator 164 b provides the user with a reference or indication that force guide 170 b and force display 180 b signals displayed toward the bottom of GUI 120 b are associated with the compression phase of ACD CPR. The system can be configured so that decompression limit warning indicator 166 b lights up or activates when the operator applies a decompression force that exceeds a prescribed decompression force or force range. Similarly, system can be configured so that compression limit warning indicator 168 b lights up or activates when the operator applies a compression force that exceeds a prescribed decompression force or force range. These features can help the operator avoid application of excessive forces during treatment, which in some cases could cause injury to the patient.

In some cases, red caution lights may illuminate when the applied force exceeds the prescribed force range. For example, if the operator approaches or exceeds the decompression target limit, a caution light may illuminate and the handle can disconnect from the adhesive pad either immediately or shortly thereafter. In the event the handle becomes detached, the rescuer may reattach the handle by bringing the handle close to the adhesive pad, whereby the handle and the adhesive pad are coupled via magnetic attraction. Once the handle and the pad are attached, the operator can resume the compression and decompression actions of the ACD CPR method. The rescuer can avoid or minimize frequent handle detachment by following the direction provided by a force guide.

When preparing the system for use on a patient, the operator can power on the system by pushing the power button 156 b. According to some embodiments, the lights on the right side of the display will illuminate in response to activation of the power switch. In some cases, the operator may take caution not to push on the chest when pressing the power button. For example, in order for the force gauge to appropriately calibrate, it may be beneficial to have no load placed on the handle when the system is initially powered on.

ACD CPR systems disclosed herein may be operated in any of a variety of ways. For example, in one exemplary method, the operator uses the system to initially compress the chest about 1½ to about 2 inches and hold the compression for about 2 seconds. During this time, the system can measure the applied force and determine the target force automatically. In this sense, the target force corresponds to an amount of force applied so as to compress the chest about 1½ to about 2 inches. It is understood that the target force may be set at a different amount by initially compressing the chest to a different distance. Hence, the initial compression distance can determine the target force. The system may also indicate the patient's chest size by illuminating the appropriate button. In this case, the user does not have to select the chest compliance, and the system automatically determines the amount of force required to compress the patient's chest by 1½ or 2 inches. However, at any time the user can push a desired body size input (e.g. 142 b, 144 b, or 146 b) so as to select an alternate size/compliance and the target force will update to the selected size.

In another exemplary method, the operator may manually select the S (142 b), M (144 b), or L (146 b) chest size on the handle by pressing the appropriate button of the body size input 140 b. The system can recognize that the user has selected a predefined force target and then guide the user accordingly. In some embodiments, the target force values are as depicted in Table 2 below.

TABLE 2

| Patient Chest Size | Force Range (Compression) |
|---|---|
| Small Adult Chest | 60-80 lbs |
| Medium or Average Adult Chest | 80-95 lbs |
| Large Adult Chest | 95-115 lbs |

As noted elsewhere herein, in some embodiments caution lights 166 *b*, 168 *b* may illuminate when the applied force exceeds the prescribed force range. At any time, the operator can change the force target by pushing an alternate chest size or body size input 140 *b*. In this way, the operator may determine the appropriate force target during a rescue treatment, and such adjustments may be made on the fly. For example, there may be instances where a small chest is extremely rigid and may require more than 80 lbs for effective CPR. In some cases, during CPR the chest may become more compliant, and hence it may be desirable to use less force if the rescuer feels that the chest is being compressed excessively, for example by more than about 2 inches.

In yet another exemplary method, the rescuer may simply start compressions by following the pacing guide as provided by the system itself. The system can be configured to default to a target compression force associated with the medium body size selection 144 *b* or the average adult chest size, and the compression force delivered will be targeted within a range from about 80 to about 95 lbs, for example. In some cases, the decompression force target can be set at a fixed value (e.g. 20 lbs), regardless of chest size. Optionally, the decompression force target can be set at a value that is a function of chest or patient size, or compliance.

In many instances, it is beneficial for the operator to compress the chest a certain number of times (e.g. about 30) without actively pulling up beyond neutral or applying a decompression force, to ensure appropriate adhesion of the adhesive pad before beginning active decompressions. Hence, the system can be configured or programmed to illuminate the guiding light or force guide 170 *b* so as to guide the user to perform a certain number of compressions (e.g. about 30) before beginning ACD CPR. For example, the force guide 170 *b* may initiate a series of signal displays for indicators 171 *b*-175 *b* (compression phase), but not for indicators 176 *b*-178 *b* (decompression phase). When the predetermined number of compressions are complete, the guiding light or force guide 170 *b* can then direct the operator to compress and decompress in accordance with ACD CPR procedures.

According to some embodiments of the present invention, the decompression force target may be set to a predetermined value (e.g. 20 lbs), regardless of chest size. If the operator exceeds the decompression target limit, a caution light 166 *b* may illuminate and the handle can disconnect from the adhesive pad either immediately or shortly thereafter. In the event the handle becomes detached, the rescuer may reattach the handle by bringing the handle close to the adhesive pad, attaching the handle and pad via magnetic attraction, and resuming ACD CPR. The rescuer can avoid or minimize frequent handle detachment by following the direction provided by force guide 170 *b*.

Exemplary system embodiments may include a timer. For example, a system may include a timer display on the graphical user interface. A timer can be configured to keep a running count of the amount of time (e.g. number of minutes) the system has been powered on, and can be used as a guide to time medication administration or rescuer rotation. To avoid fatigue, it may be beneficial for multiple rescuers to take turns performing the compression/decompressions, changing every 2 to 3 minutes.

When the system is in place on the patient, the rescuer can kneel close to the patient's side. For optimal position, shorter rescuers may find it beneficial to elevate themselves slightly by kneeling on padding. If the patient is in bed (with hard surface under torso), it may be helpful for the rescuer to kneel next to the patient or stand on a platform of sufficient height. When the rescuer is appropriately positioned, he or she can grab the system handle with both hands, placing the heels of their hands on the handle grips or palm pads with wrists bent. The rescuer can then compress and decompress with their shoulders directly over the sternum with arms outstretched and elbows locked. The rescuer may use the large muscles in their thighs to lift and compress, bending at the waist.

According to some embodiments, the system can be configured to provide a soft start in which the initial target compression forces are not as high as the target compression forces encountered later on during CPR.

Figure 2:
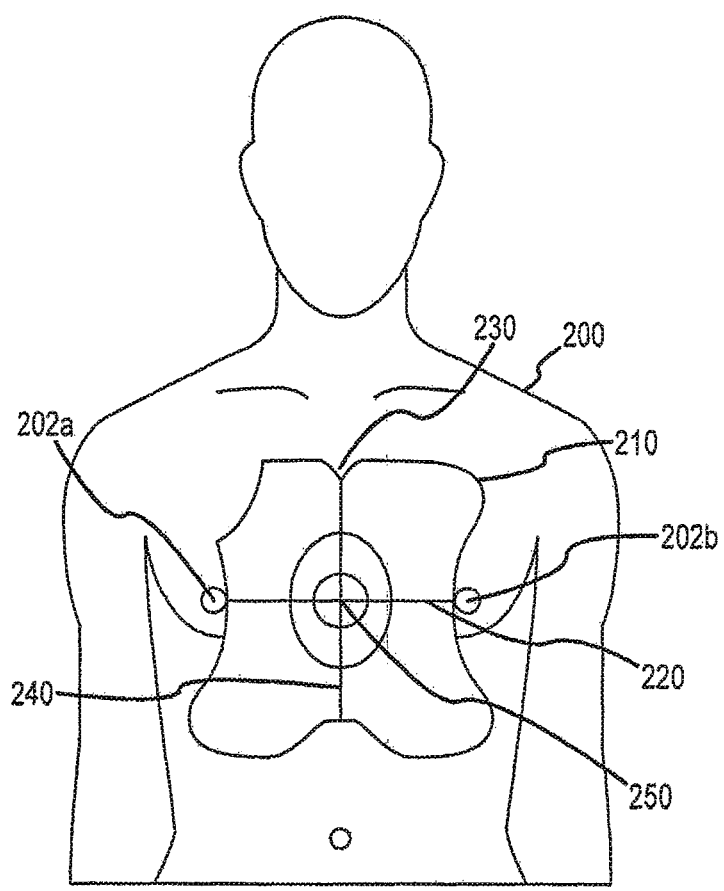
FIG. 2 shows aspects of adhesive pad placement on a patient according to embodiments of the present invention.

FIG. 2 shows an example of adhesive pad placement on a patient, according to embodiments of the present invention. As depicted here, an adhesive pad 210 is placed on patient 200, such that a nipple line 220 of pad 210 extends between the patient's nipples 202 *a*, 202 *b*. Further, adhesive pad 210 is placed such that sternum notch 230 of pad 210 is placed in the center of the patient's chest, directly over the sternum. Adhesive pad 210 may have a sternum line 240 which can be placed in alignment with the patient's sternum. When applying the system to the patient, the operator may orient the system such that the compression point of the system, which can be aligned with an adhesive pad compression point 250, is on the lower half of the sternum or center of the chest, which is at or near the compression point as prescribed in manual CPR techniques.

Figure 3:
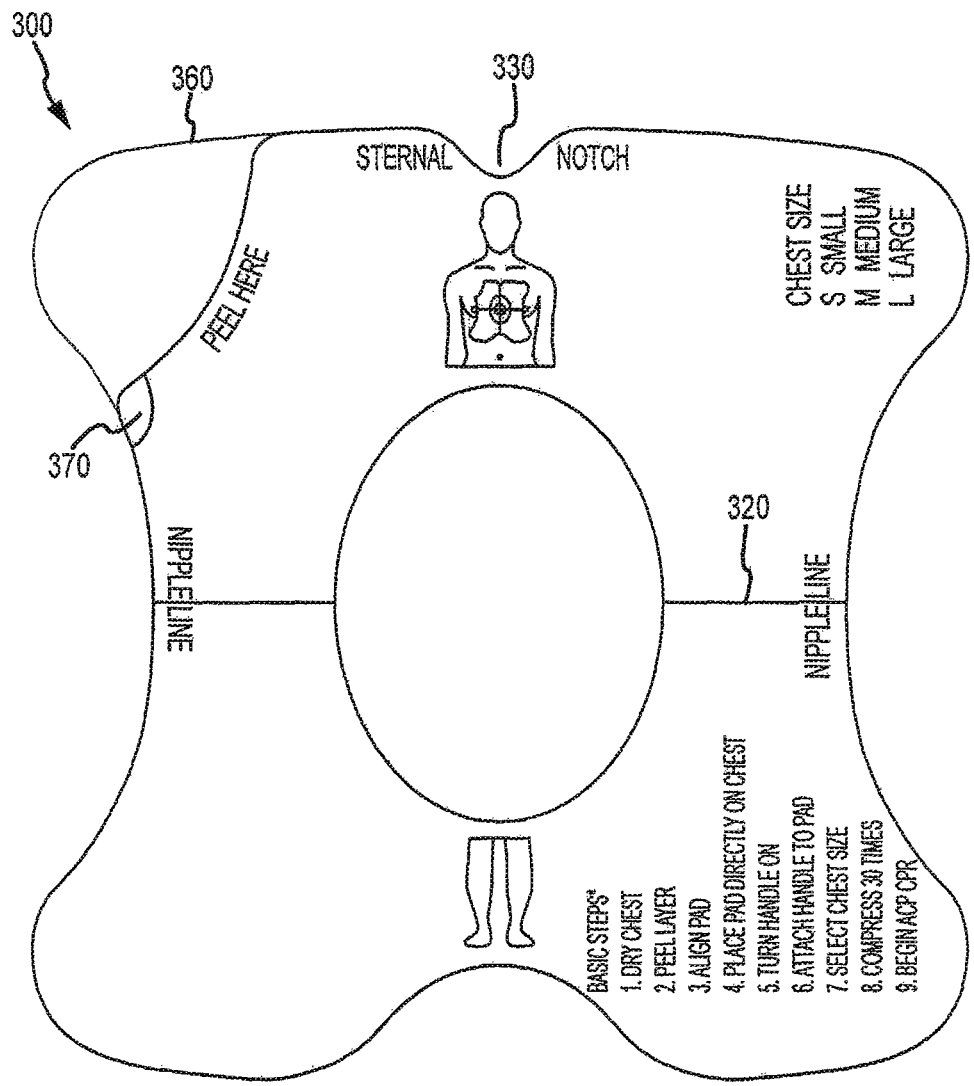
FIG. 3 depicts aspects of an adhesive pad according to embodiments of the present invention.

FIG. 3 illustrates an adhesive pad 300 according to embodiments of the present invention. Adhesive pad 300 includes a nipple line 320 which can be placed in alignment with the patient's nipples, and a sternum notch 330 that can be aligned with the patient's sternum. As shown here, adhesive pad 300 may include a liner 360 and an adhesive face 370. When applying the adhesive pad 300 to the patient, the operator may peel or remove liner 360 of the adhesive pad away from adhesive face 370, and place adhesive face 370 toward the patient's chest, for example on the sternum at the mid-nipple line as indicated on the adhesive pad shown in FIGS. 2 and 3.

When administering an ACD CPR treatment to an individual, it may be helpful to assess the condition of the patent prior to the treatment. In some cases, it may be desirable to determine that patient exhibits no signs of circulation, such as consciousness, breathing, coughing, movement, pulse, or the like. Such assessments may be performed according to local standards.

The system can be turned off after use by pressing and holding down the power button for a predetermined amount of time, for example 5 seconds. During this time, the timer may display the battery life remaining in hours. If the power button is not held for a sufficient amount of time (e.g. 5 seconds) the system may remain on, but may automatically power off after 5 minutes if no compressions are sensed. The handle can be configured to provide a predetermined number of hours of use. For example, the handle can be designed to provide about 30 hours of use. At any time, the user can determine the remaining battery life by pressing and holding the power button. The timer can display the amount of time remaining, for example by displaying the letter H followed by a number. The number can indicate the number of hours of battery life remaining. Optionally, the system can be configured so that when there is less than one hour of battery life remaining, the rate display will begin flashing whenever the device is turned on. In some embodiments, when battery life is depleted, the unit will not power up. Optionally, the handle can then be returned to the manufacturer and the unit will be refurbished and a new battery supplied.

Figure 4:
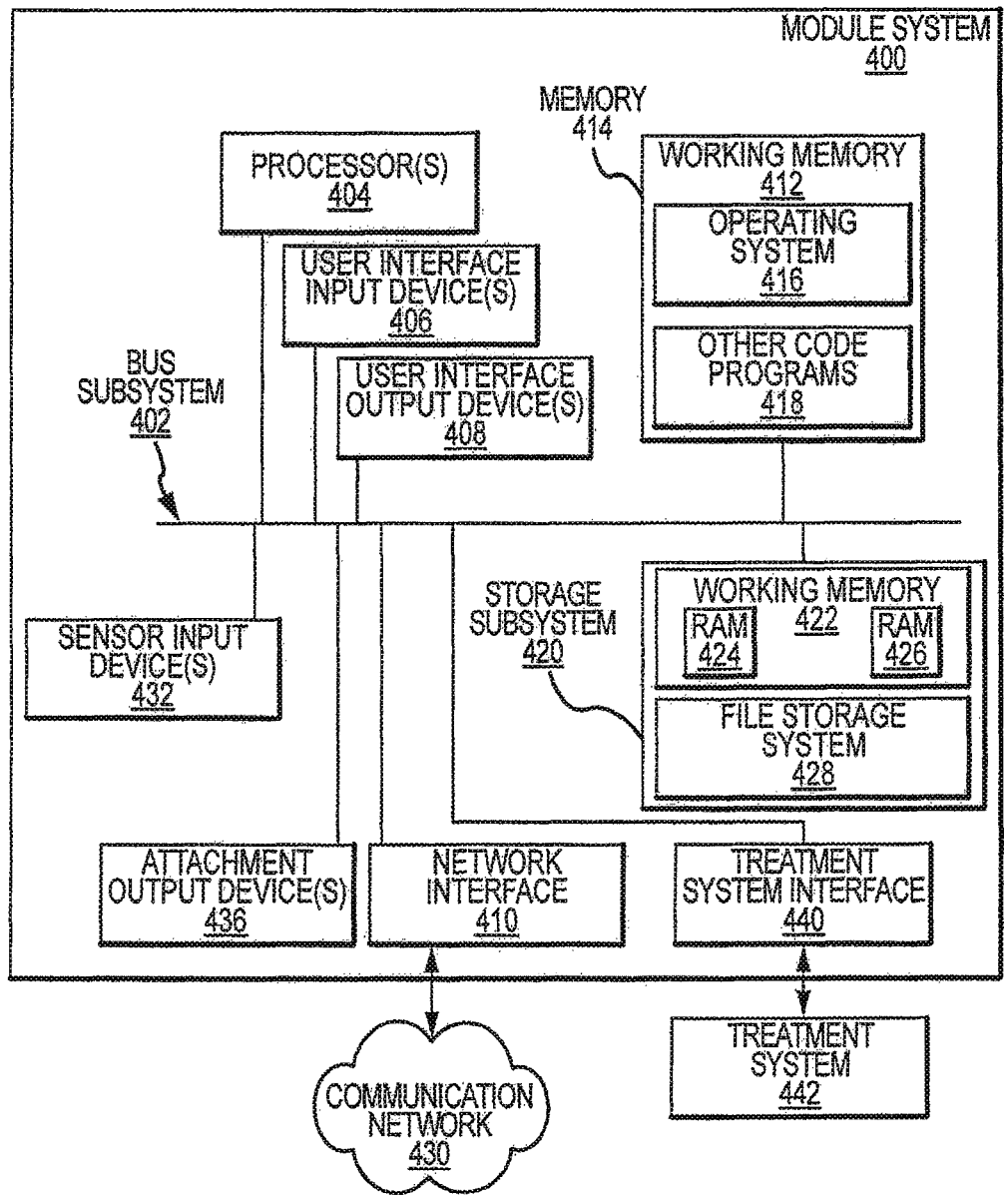
FIG. 4 provides a block diagram of an exemplary module system according to embodiments of the present invention.

FIG. 4 is a simplified block diagram of an exemplary module system that broadly illustrates how individual system elements for a module system 400 may be implemented in a separated or more integrated manner. Module system 400 may be part of or in connectivity with an ACD CPR system according to embodiments of the present invention. Module system 400 is well suited for receiving input or information from an operator, a patient, or both, and for displaying output or information as part of an ACD CPR treatment. Module system 400 as shown here includes hardware elements that are electrically coupled via a bus subsystem 402, including one or more processors 404, one or more input devices 406 such as user interface input devices, one or more output devices 408 such as user interface output devices, a network interface 410, and a load system interface 440 that can receive signals from and transmit signals to load system 442.

In some embodiments module system 400 also comprises software elements, shown as being currently located within working memory 412 of memory 414, including an operating system 416 and other code 418, such as a program designed to implement methods of the invention.

Likewise, in some embodiments module system 400 may also include a storage subsystem 420 that can store the basic programming and data constructs that provide the functionality of the various embodiments of the present invention. For example, software modules implementing the functionality of the methods of the present invention, as described herein, may be stored in storage subsystem 420. These software modules are generally executed by the one or more processors 404. In a distributed environment, the software modules may be stored on a plurality of computer systems and executed by processors of the plurality of computer systems. Storage subsystem 420 can include memory subsystem 422 and file storage subsystem 428. Memory subsystem 422 may include a number of memories including a main random access memory (RAM) 426 for storage of instructions and data during program execution and a read only memory (ROM) 424 in which fixed instructions are stored. File storage subsystem 428 can provide persistent (non-volatile) or non-transitory storage for program and data files, and may include tangible storage media which may optionally embody patient, treatment, assessment, or other data. File storage subsystem 428 may include a hard disk drive, a floppy disk drive along with associated removable media, a Compact Digital Read Only Memory (CD-ROM) drive, an optical drive, DVD, CD-R, CD RW, solid-state removable memory, other removable media cartridges or disks, and the like. One or more of the drives may be located at remote locations on other connected computers at other sites coupled to module system 400. The modules implementing the functionality of the present invention may be stored by file storage subsystem 428. In some embodiments, the software or code will provide protocol to allow the module system 400 to communicate with communication network 430. Optionally, such communications may include dial-up or internet connection communications.

It is appreciated that system 400 can be configured to carry out various aspects of methods of the present invention. For example, processor component or module 404 can be a microprocessor control module configured to receive physiological, device, or treatment parameter signals from sensor input device or module 432 or user interface input device or module 406, and to transmit treatment signals to output device or module 436, user interface output device or module 408, network interface device or module 410, or any combination thereof. Each of the devices or modules according to embodiments of the present invention can include one or more software modules on a computer readable medium that is processed by a processor, or hardware modules, or any combination thereof. Any of a variety of commonly used platforms, such as Windows, Macintosh, and Unix, along with any of a variety of commonly used programming languages, may be used to implement embodiments of the present invention.

User interface input devices 406 may include, for example, a touchpad, a keyboard, pointing devices such as a mouse, a trackball, a graphics tablet, a scanner, a joystick, a touchscreen incorporated into a display, audio input devices such as voice recognition systems, microphones, and other types of input devices. User input devices 406 may also download a computer executable code from a tangible storage media or from communication network 430, the code embodying any of the methods of the present invention. It will be appreciated that terminal software may be updated from time to time and downloaded to the terminal as appropriate. In general, use of the term "input device" is intended to include a variety of conventional and proprietary devices and ways to input information into module system 400.

User interface output devices 406 may include, for example, a display subsystem, a printer, a fax machine, or non-visual displays such as audio output devices. The display subsystem may be a cathode ray tube (CRT), a flat-panel device such as a liquid crystal display (LCD), a projection device, or the like. The display subsystem may also provide a non-visual display such as via audio output devices. In general, use of the term "output device" is intended to include a variety of conventional and proprietary devices and ways to output information from module system 400 to a user.

Bus subsystem 402 provides a mechanism for letting the various components and subsystems of module system 400 communicate with each other as intended. The various subsystems and components of module system 400 need not be at the same physical location but may be distributed at various locations within a distributed network. Although bus subsystem 402 is shown schematically as a single bus, alternate embodiments of the bus subsystem may utilize multiple busses.

Network interface 410 can provide an interface to an outside network 430 or other devices. Outside communication network 430 can be configured to effect communications as needed or desired with other parties. It can thus receive an electronic packet from module system 400 and transmit any information as needed or desired back to module system 400. In addition to providing such infrastructure communications links internal to the system, the communications network system 430 may also provide a connection to other networks such as the internet and may comprise a wired, wireless, modem, and/or other type of interfacing connection.

It will be apparent to the skilled artisan that substantial variations may be used in accordance with specific requirements. For example, customized hardware might also be used and/or particular elements might be implemented in hardware, software (including portable software, such as applets), or both. Further, connection to other computing devices such as network input/output devices may be employed. Module terminal system 400 itself can be of varying types including a computer terminal, a personal computer, a portable computer, a workstation, a network computer, or any other data processing system. Due to the ever-changing nature of computers and networks, the description of module system 400 depicted in FIG. 4 is intended only as a specific example for purposes of illustrating one or more embodiments of the present invention. Many other configurations of module system 400 are possible having more or less components than the module system depicted in FIG. 4. Any of the modules or components of module system 400, or any combinations of such modules or components, can be coupled with, or integrated into, or otherwise configured to be in connectivity with, any of the treatment system embodiments disclosed herein. Relatedly, any of the hardware and software components discussed above can be integrated with or configured to interface with other medical assessment or treatment systems used at other locations.

In some embodiments, the module system 400 can be configured to receive a physiological parameter of the patient at an input module. Physiological parameter data can be transmitted to an assessment module where a physiological profile is determined. The profile can be output to a system user via an output module. In some cases, the module system 1300 can determine a treatment protocol for the patient, based on a physiological parameter or profile, for example by using a treatment module. The treatment can be output to a system user via an output module. Optionally, certain aspects of the treatment can be determined by an output device, and transmitted to a treatment system or a subdevice of a treatment system. Any of a variety of data related to the patient can be input into the module system, including age, weight, sex, treatment history, medical history, and the like. Parameters of treatment regimens or diagnostic evaluations can be determined based on such data.

Figure 5A:
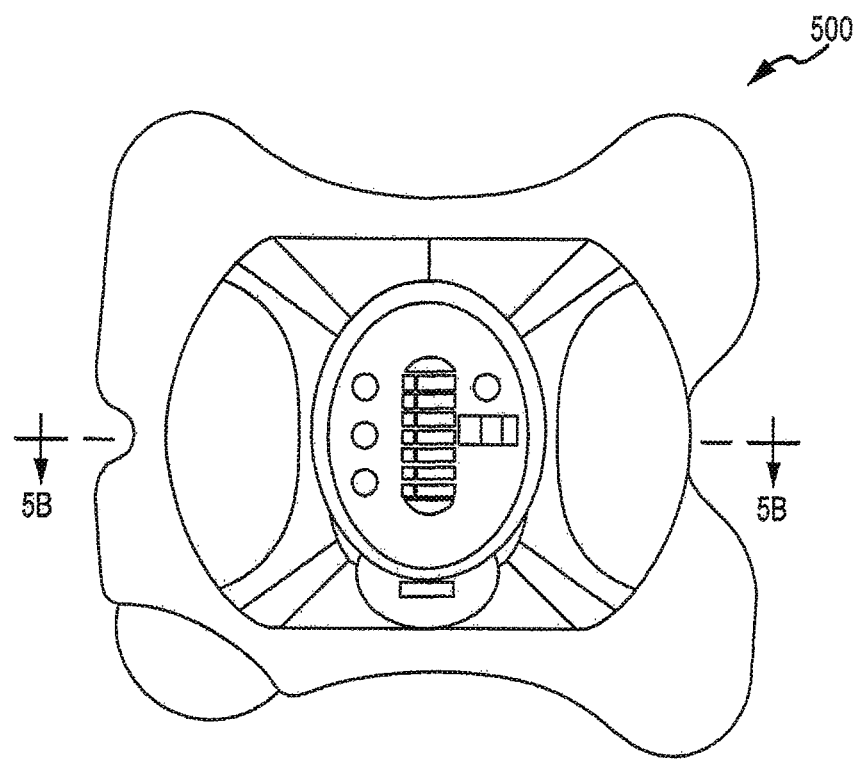
FIGS. 5A to 5D depict aspects of a magnetic coupling mechanism in an external chest compression and decompression system according to embodiments of the present invention.
Figure 5B:
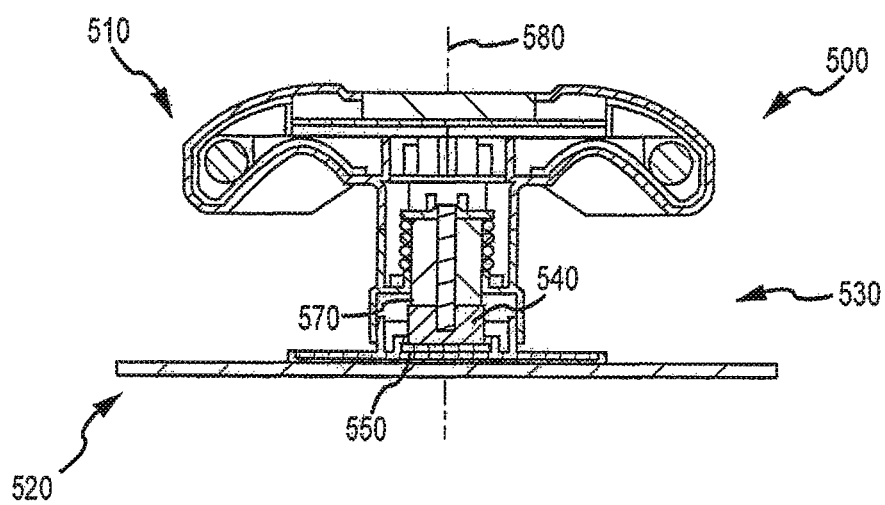
Figure 5C:
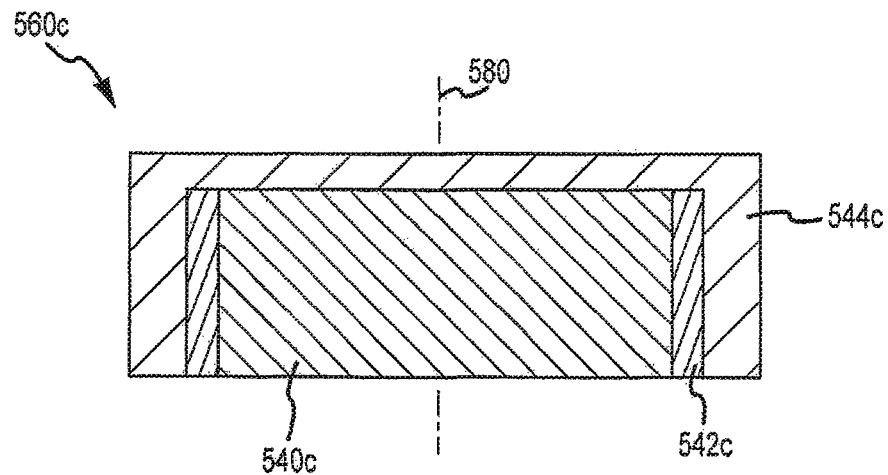
Figure 5D:
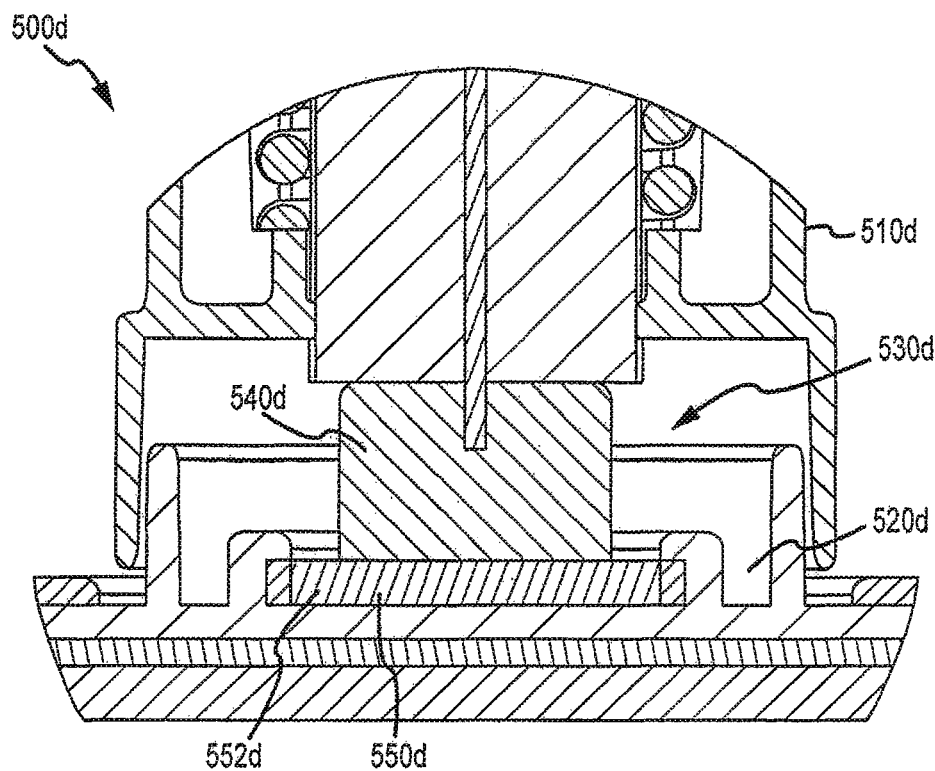

FIGS. 5A to 5D depict aspects of an exemplary magnetic coupling mechanism in an external chest compression and decompression system. FIG. 5A provides a top view of compression and decompression system 500. FIG. 5B provides a cross-section view of compression and decompression system 500, which includes a handle assembly 510 releasably coupled with an adhesive pad assembly 520. As shown here, system 500 may include a coupling mechanism 530 between a disposable adhesive pad 520 and a system handle 510. The coupling mechanism 530 can include a magnet 540 and a magnet keeper 550. In some cases, as depicted in FIG. 5C, a magnet 540 $c$ may include or be part of a magnet assembly 560 $c$ having a magnet 540 $c$, a non-ferrous spacer 542 $c$, and a ferrous container 544 $c$ for directing the magnetic flux from the pole of the magnet furthest away from the magnet keeper to the magnet keeper. The poles of the magnet can be arranged such that the poles are aligned along the axis 580 of the system piston 570. As shown in FIG. 5D, a magnetic keeper 550 $d$ on the disposable adhesive pad assembly 520 $d$ of system 500 $d$ can include a magnet 552 $d$ with poles arranged in the opposite direction of the system handle magnet 540 $d$ or of a ferrous material such as 12L14 carbon steel having a high capacity for carrying magnetic flux. A magnetic coupling between system handle assembly 510 $d$ and adhesive pad assembly 520 $d$ can be made quickly. Relatedly, the amount of effort involved with establishing a magnetic coupling is typically less than the effort involved with disengaging the magnetic coupling. Further, the force of the disconnection of the magnetic coupling can be stable over a wide range of operating environments.

According to some embodiments, a magnetic coupler mechanism can include a magnet assembly disposed on or coupled with a handle, and a keeper assembly disposed on or coupled with a pad. For example, a magnetic coupler mechanism 530 $d$ as shown in FIG. 5D may include magnet 540 $d$, or magnet assembly (such as magnet assembly 560 $c$ shown in FIG. 5C), and keeper assembly 550 $d$. The magnet 540 $d$ or magnet assembly can be coupled with or part of system handle assembly 510 $d$. Keeper assembly 550 $d$ can be coupled with or part of adhesive pad assembly 520 $d$. The magnet assembly and keeper assembly in combination may be referred to as a coupler assembly. In some cases, the coupler assembly can operate to provide a consistent release force allowing the handle to separate from the pad prior to the pad releasing from the patients skin. In addition, it may be desirable that the magnet assembly does not have a magnetic field that is widely dispersed, but rather focused in the direction of the keeper. To focus the magnetic field, the magnet assembly can include a magnetic core, a non-magnetic sleeve, and a ferromagnetic pot which conducts the magnetic flux from the pole on the enclosed side of the magnet to the open side of the magnet. The arrangement of a jacket with the magnet can focus the majority of the magnetic flux to the open end of the assembly. For example, as shown in FIG. 5C, magnet assembly 560 $c$ may include a magnetic core 540 $c$, a non-magnetic sleeve 542 $c$, and a ferromagnetic pot 544 $c$ which conducts the magnetic flux from the pole on the enclosed side 540 $c'$ of the magnet to the open side 540 $c''$ of the magnet. The arrangement of a jacket 544 $c$ with the magnet can focus the majority of the magnetic flux to the open end of the assembly 560 $c$. Control or selection of the material properties of the keeper 550 $d$ can be helpful to achieve a consistent release force. In some cases, the material can have a high magnetic saturation such as a 12L14 or AISI 1010 or 1020 material and the magnetic properties of the material can be controlled through the control of material temper. For example, materials can be processed to a fully annealed condition.

In addition to the magnetic coupling mechanism described herein, other types of breakaway mechanisms can be used in an external chest compression and decompression for coupling a disposable adhesive pad with a system handle. Exemplary breakaway mechanisms can be configured to allow the handle to disengage from the pad in a controlled manner.

Figure 6A:
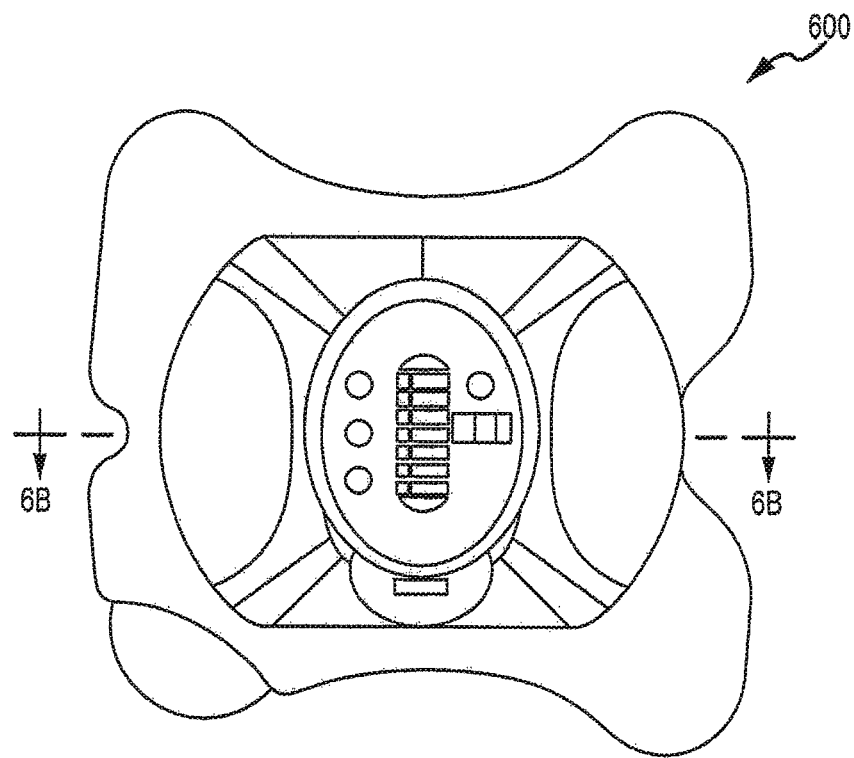
FIGS. 6A to 6D illustrate features or properties of a load cell or preload spring mechanism according to embodiments of the present invention.
Figure 6B:
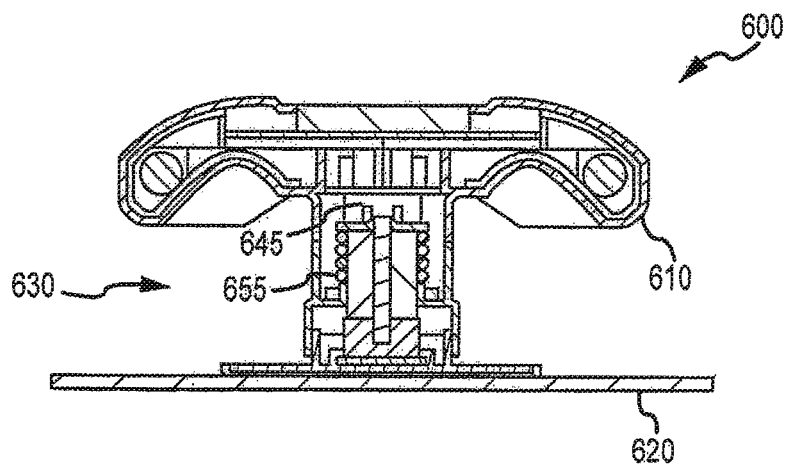
Figure 6C:
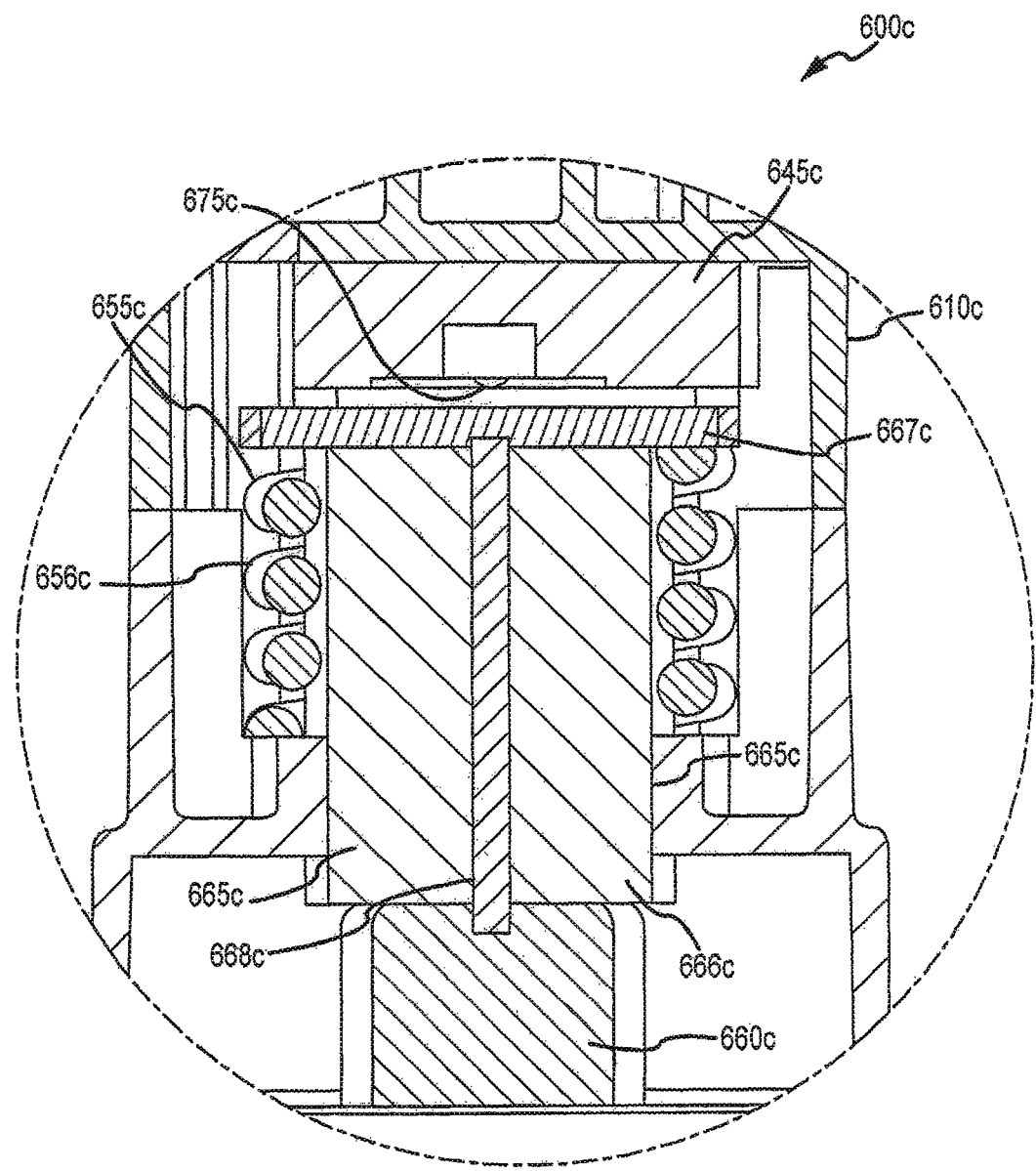

FIGS. 6A to 6C illustrate features of an exemplary load cell or preload spring mechanism, according to embodiments of the present invention. FIG. 6A provides a top view of compression and decompression system 600. FIG. 6B provides a cross-section view of compression and decompression system 600, which includes a handle assembly 610 releasably coupled with an adhesive pad assembly 620. As shown here, system 600 may include a coupling mechanism 630 between a disposable adhesive pad 620 and a system handle 610. The coupling mechanism 630 can include a load cell assembly 645 and a preload spring assembly 655. Such load cell or spring mechanisms can be incorporated in a system for performing external chest compressions and decompressions. In some cases, a baseline level of compression can be applied to the load cell via a preload spring. The preload spring can apply enough force to a device piston in a direction simulating compression such that the device piston is in kept in contact with the load cell throughout the compression/decompression cycle. For example, as shown in FIG. 6C, system 600 $c$ includes a handle assembly 610 $c$, a load cell assembly 645 $c$, a preload spring assembly 655 $c$ having a spring 656 $c$, a magnet assembly 660 $c$ for releasable coupling with a keeper assembly of a pad assembly. System 600 $c$ also includes a spacer mechanism 665 $c$ in operative association with spring assembly 655 *c* or spring 656 *c* and magnet assembly 660 *c*. In some cases, spacer mechanism 665 *c* includes a post 666 *c* coupled with a shoulder mechanism 667 *c* such as a disc. System 600 *c* may also include a fastener 668 *c* or fastener means for fixedly attaching disc 667 *c*, post 666 *c*, and magnet 660 *c*. Hence, the disc, post, and magnet may operate in unison, such that compression or decompression force applied to the magnet can be transmitted to the disc, and vice versa. As depicted in FIG. 6C, load cell 645 *c* can contact spacer mechanism 665 *c* or piston at a contact point 675 *c*. Preload spring 656 *c* can operate to maintain or facilitate contact between magnet 660 *c* and load cell 645 *c*, for example via spacer mechanism 665 *c*. Optionally, the use of the preload spring may eliminate a need for independent sensors for both compression and decompression.

According to some embodiments, both compression and decompression forces can be measured with a load cell. To accomplish measuring decompression forces the handle can include an internal spring mechanism that creates a compressive load on the load cell when the handle is experiencing no external loading. The internal spring mechanism can apply a compressive force to the load cell at certain times or periods. For example, the internal spring mechanism can apply a compressive force to the load cell at all times or at substantially all times. The handle can include a means of compensation for this initial compressive force. Compensation for the internal spring mechanism can be accomplished by zeroing the load cell output, in software, upon each startup which can eliminate or reduce effects of sensor and spring force drift due to age, temperature, or other sources.

Figure 6D:
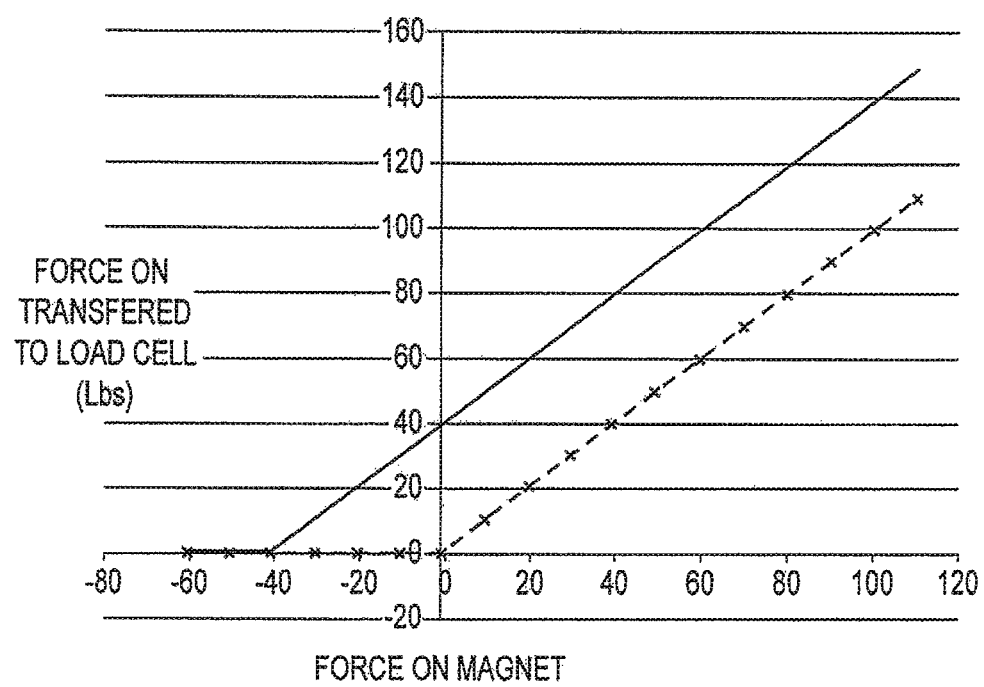

The graph in FIG. 6D shows exemplary relationships between (a) the force that is applied to the system handle and transferred at least in part to the patient, for example via the magnet [x-axis], and (b) the force transferred to the load cell [y-axis]. Positive forces are compressive and negative forces are decompressive. This graph illustrates the effect of preload application on the load cell, and shows how a preload spring can condition the forces applied to the magnet prior to transmission to the load cell. As depicted in this embodiment, the force on the magnet can be in a range between about −60 lbs to about 110 lbs, and the force transferred to the load cell can be in a range between about 0 lbs and about 150 lbs. Systems can be configured to provide any of a variety of force profiles, as desired. According to this graph, a preload mechanism, such as a preload spring assembly, allows the load cell to measure decompressive forces. The force at the magnet can be the same or substantially the same as the force at the handle, which can also be equivalent to the force applied to the patient, for example where the handle is considered a rigid mechanism. According to some embodiments, the load cell or force sensor, which may be present in the handle or at another location in the system, may be configured to measure or sense compressive forces. In some instances, the system may be configured so that the preload spring or mechanism applies a compressive force to the load cell at all times.

Two load cell configurations are depicted in FIG. 6D. The dashed line represents a load cell or force profile without a preload spring or mechanism, and the solid line represents a load cell or force profile with a preload spring or mechanism. In the particular embodiment depicted here, the amount of preload is 40 lbs. In various embodiments, any amount of preload can be selected as desired. In the dashed line profile, where a preload spring or mechanism is not present, the force on the load cell is zero when the handle is pulled up, for example during the decompression phase. In some cases, a device may not have the capability to measure decompressive forces unless preload is provided. In the solid line profile, where a preload spring or mechanism is present, there is 40 lbs of preload force applied to the load cell in the absence of force applied to the handle. Hence, the preloaded configuration allows measurement of decompressive forces, for example up to the amount of the preload force. In some embodiments, the preload mechanism may include a coil spring. Optionally, a preload mechanism may include a Belleville washer. In some cases, preload can be provided by a resilient housing material, or otherwise built into the housing element in which the preload is applied by the resilience of the housing material. According to some embodiments, preload can be provided by preload mechanisms that include rubber, an elastomeric substance, fluid, or other compressible materials or assemblies.

In some instances, guided ACD CPR systems and methods can involve the use of a load cell in conjunction with an accelerometer. The load cell can provide a means of measuring active decompression and an auto zeroing of the accelerometer. The accelerometer can provide a direct measurement of chest wall displacement in techniques involving, for example, a 1.5 to 2.0 inch displacement.

Exemplary system and method embodiments may provide treatment with particularly effective compressive area and contact area configurations. For example, a device contact area or adhesive pad can be 2 to 4 times larger than the compressive area. Beneficially, a large contact area can make it easier for a user or operator to generate a full or greater decompression resulting in more blood flow back to the heart. This may be a result of the ability of a large contact area to physically raise or lift a corresponding large area of the patient's chest during a decompression maneuver. Moreover, a sufficiently large compression surface area can allow the operator or user to provide enhanced coronary perfusion pressure or more blood flow from the heart to other tissue or organs during compression, thus improving the likelihood of a successful medical outcome for the patient such as the return of spontaneous circulation. According to some embodiments, the systems and methods discussed herein can be used without preventing lateral displacement of the chest. For example, these techniques can be used without binding or constricting the chest with a CPR band device, or otherwise without applying a circumferential device to the patient.

Accordingly, embodiments of the present invention provide systems and methods for actively compressing and expanding an area of the body that involve a compression element operably coupled to a flexible surface element that is adapted to be removably attached to a body part over a contact area. The compression element is configured to be alternately pressed and lifted, thereby pressing upon and lifting the surface element. When the compression element is pressed, it applies a compressive force over a compressive area of the surface element and the body part to which it is attached. When the compression element is lifted, the contact area of the body part attached to the surface element is lifted by the surface element.

In one embodiment, the device may be used to compress and expand the thoracic cavity or chest, and to transform the chest into an active bellows. The increased active expansion of the chest which occurs when the surface element is lifted causes unexpectedly enhanced negative pressure within the intrathoracic region ("negative ITP"), thereby drawing a larger amount of air into the lungs to more effectively ventilate the patient than previous devices. Accordingly, the device may be used to enhance the expansion of the chest and resultant lowering of negative ITP for a variety of purposes, e.g. to perform active compression/decompression CPR, to treat low blood pressure, to increase blood circulation, and the like. It has been found that the larger the body contact area provided by the surface element, the lower the negative ITP that can be achieved using the device if the chest is compliant or if a rib has been broken. In exemplary embodiments, the body contact area provided by the lower surface of the surface element can be between about two and about four times greater than the compressive area to which compressive force is applied on the upper surface of the surface element. Body contact areas less than the specified range may result in unsatisfactory expansion of the chest, excessive forces that are concentrated on a small area (which could damage the skin), and provide less than optimal negative ITP, whereas body contact areas more than the specified range can result in unsatisfactory compression of the chest.

The device may be used in both manual and powered systems. In a powered system, the compression element may be attached to a mechanical drive element, such as a mechanical link which is part of a powered automatic drive system which accomplishes the up and down motions of the compression and expansion strokes. In a manual system, the compression element may comprise a handle that can be grasped by the operator's hands and moved up and down to accomplish the required or prescribed strokes.

In one embodiment, the device includes a mushroom-shaped compressive element having a dome-shaped handle disposed on the top end of a centrally-located rigid connecting stem. The bottom end of the stem is connected to the top surface of a generally planar flexible contact pad and defines a compressive area. The lower surface of the contact pad may be covered with an adhesive adapted to adhere to the anterior surface of a patient's chest and defines a contact area. The handle's dome-shaped upper surface is separated from an annular planar lower surface by a peripheral flange, thereby allowing an operator to grasp the handle with the palms of both hands positioned on the upper surface, the fingers curled around the peripheral flange and the finger tips positioned against the lower surface.

According to certain method embodiments, the increased negative intrathoracic pressures of a patient may be effected using the device generally described herein. After positioning both hands on the handle, the operator may apply downward force against the handle with the palms of the hands. The downward force is transferred through the connecting stem to a compressive area of the contact pad which is generally defined by the cross-sectional area of the lower end of the connecting stem. The device may be positioned on the anterior surface of a patient's chest so that the compressive area is generally positioned over the patient's sternum.

The downward force compresses the patient's chest over the compressive area and increases ITP sufficiently to induce blood circulation from the chest. Then, the operator may lift up the handle with the fingers under the lower surface of the handle to provide an upward force on the connecting stem, which in turn moves the top surface of the contact pad in an upward direction. Since the contact pad is adhered to the patient's chest across the entire contact area covered by the contact pad, the upward movement of the contact pad actively expands the patient's chest. This expansion reduces ITP to induce blood circulation into the chest and ventilates the patient's lungs. The downward and upward strokes are repeated at a rate sufficient to maintain blood circulation and enhance ventilation, typically with a compression distance in the range from about 3.5 cm to 5 cm and a rate in the range of 60 repetitions to 100 repetitions per minute.

The devices and methods described herein have been found to be particularly useful in manual CPR when the performer kneels beside the patient and grasps the handle with fully-extended arms, with the performer's palms engaging the upper surface of the handle and fingers grasped around the peripheral flange of the handle. The performer may then apply the necessary downward and upward strokes with fully-extended, locked arms while holding the device in a very stable configuration.

In some cases, the compression element connected to the upper surface of the surface element may be attached to a mechanical drive element, such as a mechanical link which is part of a powered automatic drive system. In this way, active automatic compression and expansion of the patient's chest can be performed.

Figure 7:
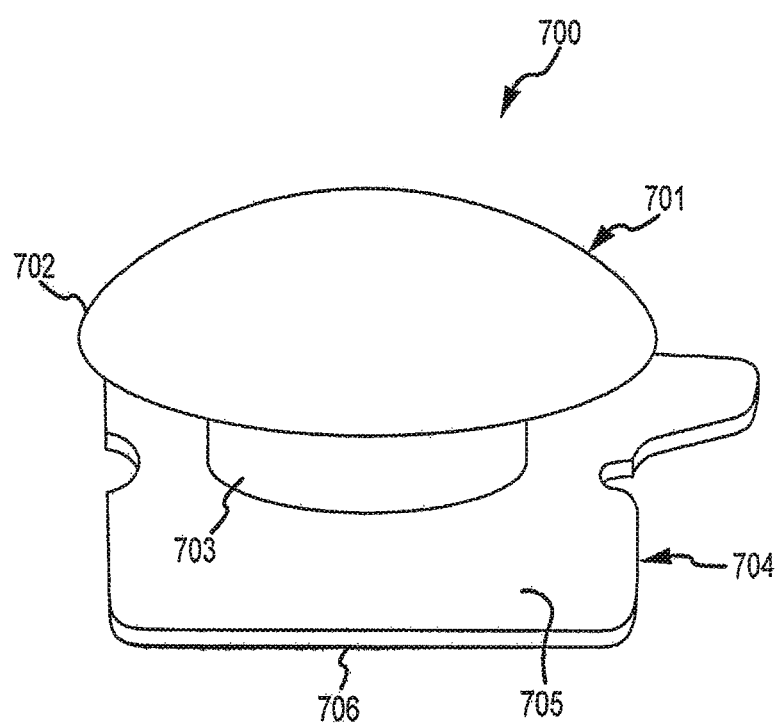
FIG. 7 is a perspective top view of a device in accordance with embodiments of the present invention.
Figure 8:
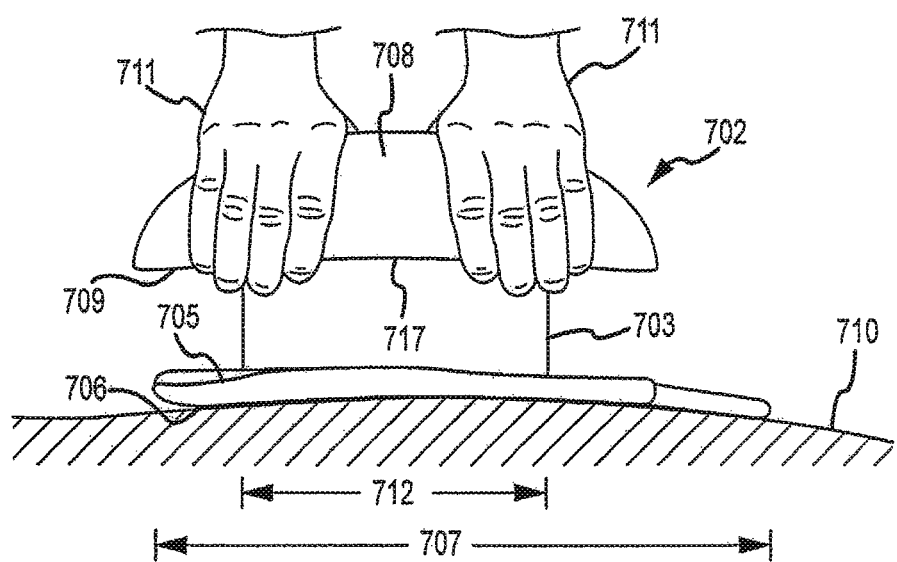
FIG. 8 is a perspective side view of the device shown in FIG. 7.
Figure 9:
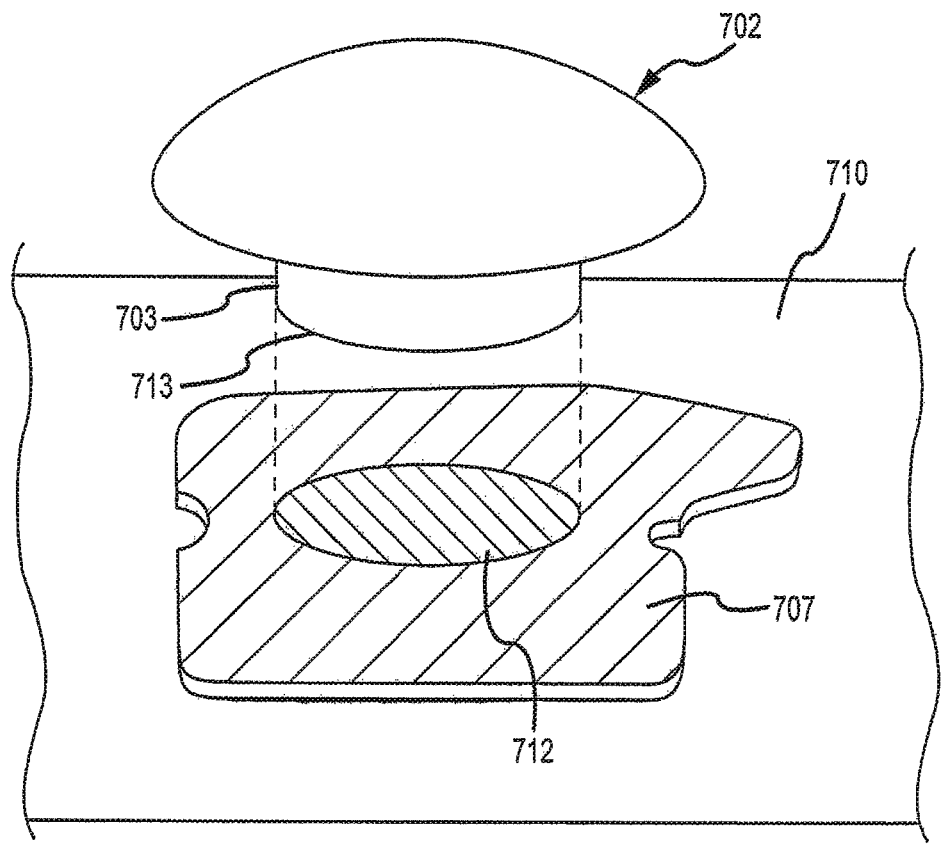
FIG. 9 is an exploded perspective view of the device shown in FIG. 7.

FIGS. 7-9 illustrate aspects of a device embodiment which can be used for manual operation. The same numbers appearing in these different figures refer to the same elements. Device 700 comprises a mushroom-shaped interface element 701 having a handle 702 operably connected through a connecting stem 703 to upper surface 705 of a flexible contact pad 704.

Contact pad 704 may be constructed from a layer of suitable resilient material such as a natural or synthetic foam. All or a substantial part of a lower surface 706 may be covered with adhesive material suitable for adhering contact pad 704 to the anterior surface of a patient's chest 710. The dimensions of contact area 707 are defined by the "footprint" of contact pad 704 that is adhered to the patient's chest 710 (or other body locations). Suitable adhesive materials may include pressure-sensitive adhesives such as those which are commonly used on medical bandages, transdermal patches, and other medical applications. Other useful adhesives may include natural and synthetic rubber-based formulations, such as polyisobutylenes, and acrylic and silicon-based materials. Swollen hydrogels, such as poly (vinyl pyrrolidone), may be suitable when used in conjunction with electrodes, as described hereinafter. When use of device 700 is completed, contact pad 704 may be removed by conventional means, e.g. by applying a solvent to the adhesive, simply pulling the pad away from the chest, and the like.

The dimensions of contact pad 704 can be chosen to provide a desired contact area 707. In accordance with embodiments of the invention, the larger that contact area 707 is relative to compressive area 712, the more expansion of chest 710 can be achieved using device 700 if the chest is compliant or if a rib has been broken, for example. For example, if the dimensions of pad 704 are 8"×10" and the operator applies a compressive force on handle 702 across compressive area 712 having dimensions of 3"×3", chest 710 is subject to greater upward force (and therefore lower negative ITP) than if the dimensions of pad 704 are 4"×6".

Typically, for adult patients, contact pad 704 will have a generally square or rectangular shape. For children, the dimensions may be in considerably smaller. Other shapes may also be useful, it being necessary only that contact pad 704 be shaped to provide for a desired force distribution over compressive area 712 as well as provide for contact area 707 to be at least twice to four times as large as compressive area 712 so that improved negative ITP in accordance with the invention can be achieved. For example, it may be desirable to shape the lower surface 706 of contact pad 704 to conform to the general contours of the patient's chest 710. In addition, it may be desirable to provide a plurality of sizes and shapes of contact pad 704 in a single kit so that a contact pad may be selected for the individual patient.

The thickness of contact pad 704 may depend on the resiliency of the material employed. For manual operation, an exemplary thickness for contact pad 704 is about 3/16".

Handle 702 comprises dome-shaped upper surface 708 and an annular planar lower surface 709 separated by peripheral flange 710. The top of stem 703 is centrally located within annular lower surface 709 of handle 702 and the bottom of stem 703 is centrally located on the planar upper surface 705 of contact pad 704. The cross-section of bottom end 713 of stem 703 defines the dimensions of compressive area 712. The shape of handle 702 allows the operator's hands 711 to grasp handle 702 with the palms resting on upper surface 708, the fingers wrapped around ridge 717 and the finger tips positioned against lower surface 709 (FIG. 8). This arrangement allows the operator to press down on upper surface 708 of handle 702 with the palms of the hands 711 to apply a compressive force against pad 704 and patient's chest 710 over a compressive area 712. The arrangement also allows the operator to lift up on lower surface 709 of handle 702 with the fingers of hands 711. Since lower surface 706 of pad 704 is adhered to contact area 707 of patient's chest 710, this lifting motion on handle 702 lifts and expands patient's chest 710 across contact area 107. Handle 702 and connective stem 703 may be constructed from a suitable rigid material, e.g. a molded plastic. Handle 702 may also be filled with a gel, foam, padding or the like to enhance its shock-absorbing and distributing capability.

Figure 10A:
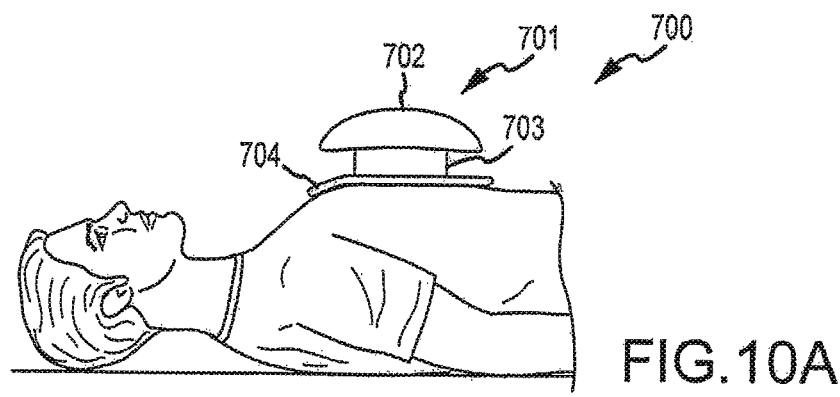
FIGS. 10A to 10C are schematic illustrations of the device shown in FIG. 7 in use during the positioning (FIG. 10A), compression (FIG. 10B) and expansion (FIG. 10C) steps of a method according to embodiments of the present invention.
Figure 10B:
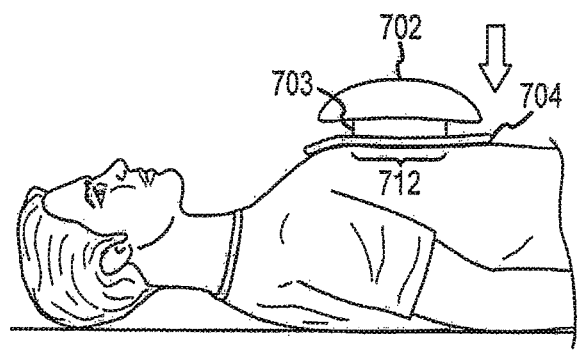
Figure 10C:
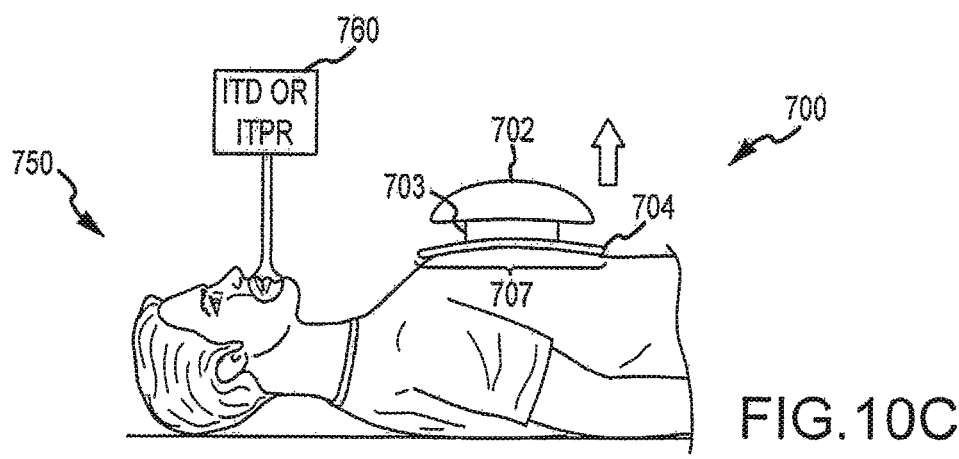

Referring now to FIGS. 10A-10C, use of the device in resuscitating a patient will be described. The device is initially placed on the anterior surface of the patient's chest about mid-sternum, as illustrated in FIG. 10A. The operator then grasps handle 702 with both hands, as shown in FIG. 8, pressing the palms of the hands 711 against upper surface 708 while grasping the peripheral flange 710 with the fingers. The operator applies sufficient downward force on handle 702 through stem 703 so that the chest is compressed within compressive area 712, as shown in FIG. 10B. Typically a compressive force is used to depress the chest. Contact pad 704, coupled to stem 703, may be formed of a suitably resilient material, for example, silicone rubber, which softens the application of downward force through the stem 703 across compressive area 712. The initial position of the patient's chest is illustrated in broken line in FIG. 10B. During the compression stroke, the chest is compressed across compressive area 712 to the position illustrated in solid line in FIG. 10B.

After the compression stroke is completed, the operator raises up on the handle 702 to expand the chest, as illustrated in FIG. 10C. Again, the rest position of the chest is illustrated in broken line and the expanded position is shown in solid line. During the chest expansion stroke, the upward movement of handle 702 through stem 703 raises contact pad 704, which is adhered to the chest across contact area 707. The chest is pulled upward with contact pad 704 to cause the desired chest expansion. Handle 702 may be raised in an amount sufficient to apply an expansion force. The compression and expansion steps may be alternated at a rate in the range from about 80 to 100 per minute. As previously explained, the larger contact area 707 is relative to compressive area 712, the more chest expansion (and negative ITP) that can be achieved with each stroke. As further described elsewhere herein, and as shown in FIG. 10C, an active compression decompression cardiopulmonary resuscitation device 700 may be used in conjunction with, or may be part of a system 750 which includes, a device 760 for providing, facilitating, or modulating patient airway pressure, such as an impedance threshold device (ITD) mechanism or an intrathoracic pressure regulator (ITPR) mechanism. In some cases, device 760 may include a mechanism, such as a one-way valve, for occluding the patient's airway during a decompression phase. Device 760 may be used during any portion of, or throughout the entirety of, a treatment protocol, for example during one or more of the steps illustrated in FIGS. 10A-C, or in conjunction with any other method or system described herein.

It may be desirable to provide at least one element associated with the device that can measure a physiological parameter and/or display patient status information and/or feedback to the person performing the CPR. Preferably, the measuring element is associated with the surface element. Examples of physiological parameters include ventilation rates, temperature, blood pressure, heart rate, respiratory rate, and other vital signs. Some parameters may require separate monitoring devices (not illustrated) attached to the patient, and the display on the device makes the information immediately available to the person performing the CPR. Feedback information includes pressure or force applied to the patient, depth of compression, compression rate (i.e., cycles per minute), duty cycle (i.e., portion of each cycle in which the patient is compressed), and the like. Such feedback information can be provided as discrete values, e.g., with gauges or digital readouts, or may be provided with a light or sound system which indicates when certain threshold values have been met or exceeded. It may be further desirable to provide a pacing signal, e.g., either a sound or flashing light, to facilitate maintaining a desired compression rate.

Figure 11:
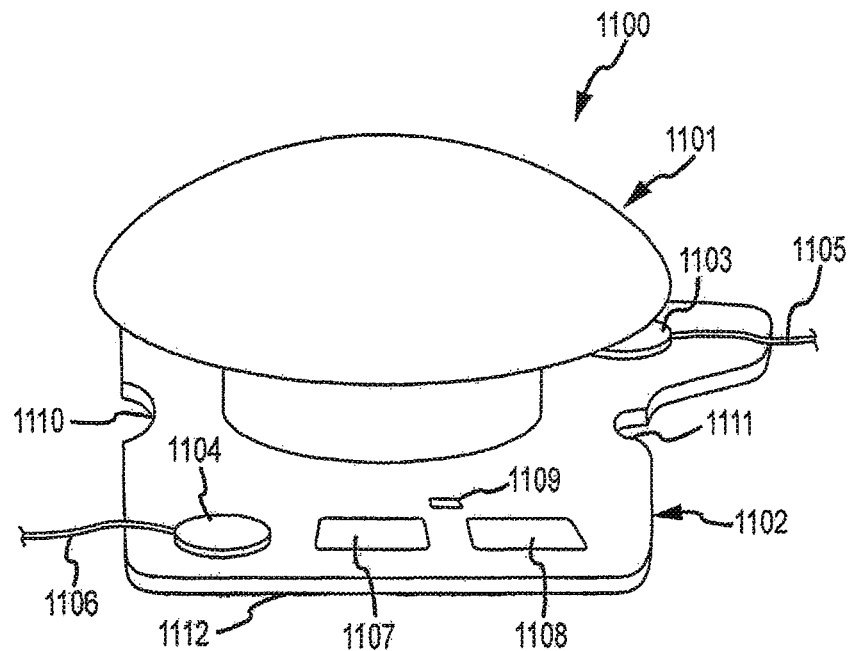
FIG. 11 is a perspective view of a device in accordance with embodiments of the present invention.

FIG. 11 illustrates an embodiment of the invention wherein the device has associated therewith one or more measuring and/or display elements. Device 1100 comprises handle or element 1101 and flexible contact pad 1102, and is similar in structure to device 700 shown in FIGS. 7-9, except that contact pad 1102 of device 1100 may optionally include one or more measuring and/or display elements. For example, in addition to adhering to a patient's chest as previously described, contact pad 1102 may serve as a platform for measuring a variety of physiological parameters, e.g. electrocardiogram parameters; provide a means to apply electricity to the body, e.g. accomplish defibrillation; provide a means to apply drugs to the body; provide a surface for installing a liquid crystal display (LCD) screen to display various feedback information; provide a means to house various body sensors, e.g. bioimpedance sensors; and provide reference features to aid in the proper placement of the device on the patient's chest.

Referring now to FIG. 11, contact pad 1102 may include imbedded automated external defibrillator (AED) electrodes 1103 and 1104 connected to AED leads 1105 and 1106, respectively. Electrodes 1103 and 1104 extend to the lower surface of contact pad 1102 and may be coated with the same adhesive material that covers the lower surface 1112 to facilitate electrocardiographic monitoring (ECM) and/or electrical defibrillation. Leads 1105 and 1106 include wires or other electrical conductors for connecting electrodes 1103 and 1104 to external ECM and/or electrical defibrillation equipment in a conventional manner. Contact pad 1102 may also optionally include electronic LCD display 1107, which shows average compression forces applied over a certain number of cycles, and electronic LCD display 1108, which shows average decompression forces over the same number of cycles. In addition, contact pad 1102 may optionally include a blinking light-emitting diode (LED) metronome to aid in the timing of the compression and expansion strokes. In some embodiments, such displays or signaling mechanisms may be positioned on or coupled with handle 1101. Furthermore, contact pad 1102 may include reference notch 1110 on its forward edge (closest to the patient's head) to aid in properly locating the patient's sternum and a reference notch 1111 on its rearward edge (closest to the patient's feet) to aid in properly locating the xyphoid process. References notches 1110 and 1111 may be used to properly place device 1100 on the patient's chest so as to prevent injury to the patient during compression and expansion strokes.

Figure 12:
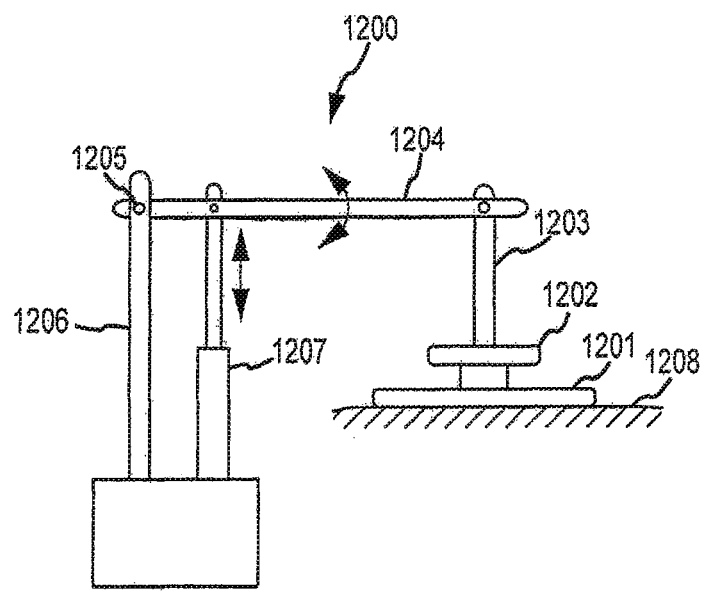
FIG. 12 is a schematic illustration of a powered automatic system using a device according to embodiments of the present invention.

The device of the present invention may also be employed in a powered or automated system, for example, such as the automated reciprocating system 1200 as illustrated in FIG. 12. Surface element 1201 may be adhered to body surface 1208 in the manner previously described. Compression element or handle 1202 may be secured to a vertical drive element 1203, which is attached to a reciprocating lever arm 1204. Lever arm 1204 may be driven in a wide variety of ways. As illustrated, a fixed fulcrum point 1205 is provided by post 1206 and lever arm 1204 is reciprocated up and down by a piston and cylinder 1207 to provide the desired compression and expansion of chest 1208.

According to embodiments disclosed herein, devices and methods for actively compressing and expanding an area of the human body may include a compression element configured to pressed and lifted, and a flexible surface element operably coupled with the compression element and configured to be removably attached to a body part over a contact area. The compressive element can be adapted to apply a compressive force to the body part through the surface element over a compressive area when the compression element is pressed. The contact area can be sized to be at least twice as large as the compressive area. Certain embodiments of the present invention are useful in the performance of cardiopulmonary resuscitation and advanced cardiac life support procedures. By alternately pressing and lifting the surface element with the compression element, the patient's chest can be compressed and expanded to improve induced ventilation and circulation. In an exemplary device, a dome-shaped handle is attached to the upper surface of a flexible contact pad by a short connecting stem structure. The bottom end of the connecting stem defines the compressive area and the lower surface of the contact pad secured to a patient's chest defines the contact area. In other embodiments, various elements may be associated with the contact pad to, for example, measure a physiological parameter, display patient feedback information, apply electricity, apply a drug, provide a sensor, provide a reference to aid in the proper placement of the surface element on the body part, etc. For automatic applications, a mechanical drive member may be secured to the compression element.

In some instances, a treatment device may include means to record the compression events, to store the data, to simultaneously or contemporaneously transmit or analyze data related to the treatment to the operator, or to transmit or analyze data related to the treatment to the operator following a patient arrest, to assess the quality of cardiopulmonary resuscitation administered by the operator, and to provide feedback to the operator regarding the quality of the administered cardiopulmonary resuscitation either during or after the arrest. Relatedly, an exemplary treatment device for actively compressing and expanding an area of the body can include a compression element that is configured to be pressed and lifted, a flexible surface element operably coupled with the compression element and configured to be removably attached to a body part, an interface for displaying information to and receiving information from an operator, a processor coupled with the interface, and a memory coupled with the processor. The memory can be configured to store a plurality of code modules for execution by the processor. The plurality of code modules can include a module for recording a compression event history, a module for storing the compression event history, a module for assessing a cardiopulmonary resuscitation quality factor, and a module for providing feedback to the operator based on the cardiopulmonary resuscitation quality factor.

Embodiments of the present invention encompass systems and methods for instructing the operator or user to perform a certain number of compressions prior to initiating active compression and decompression (pulling up on the chest). For example, systems and methods may involve instructing the operator to perform 30 compressions before they begin active compression and decompression. Such techniques can help to ensure that the pad appropriately adheres to the chest. In some cases, the device software can guide the user to perform a number of (e.g. 30) compressions before the display starts guiding the user to perform compressions and decompressions. Relatedly, a device for actively compressing and expanding an area of the body may include a compression element that is configured to be pressed and lifted, a flexible surface element operably coupled with the compression element and configured to be removably attached to a body part, an interface for displaying instructions to an operator, a processor coupled with the interface, and a memory coupled with the processor. The memory can be configured to store a plurality of code modules for execution by the processor. The plurality of code modules can include a module for providing operator instructions to perform a number of compressions prior to initiating active compression and decompression.

Further, methods and systems described herein can incorporate or be used in conjunction with techniques that involve providing a volume exchange cardiopulmonary resuscitation treatment to a patient that encompasses compressing the patient's chest during a compression phase and lifting upward the patient's anterior chest wall and occluding the patient's airway during a decompression phase. Optionally, the step of occluding the patient's airway can include occluding the airway with a one-way valve. In some cases, the step of occluding the patient's airway includes occluding the airway with a valve system that allows an operator to ventilate the patient. Techniques may also include ventilating the patient with the valve system. In some cases, it is possible to ventilate the patient by provide a positive pressure ventilation through or around the one-way valve. Optionally, techniques can include actively removing respiratory gases from the patient's lungs with a low-level vacuum. In some cases, the low-level vacuum can be continuous. In some cases, the low-level vacuum can be intermittent. These treatment approaches can also include actively withdrawing respiratory gases from the patient's lungs, and subsequently delivering a positive pressure breath to the patient. In some cases, the positive pressure breath can be delivered with a period of positive end-expiratory pressure, either before or after the positive pressure ventilation. These treatment method and device approaches can also include aspects of positive end expiratory pressure, positive pressure ventilation, or both, such as those described in U.S. patent application No. 61/218,763 filed Jun. 19, 2009 and U.S. patent application Ser. No. 12/819,959 filed Jun. 21, 2010, the contents of which are incorporated herein by reference for all purposes.

Relatedly, active compression decompression cardiopulmonary resuscitation treatments described herein can be performed in conjunction with the use of systems and methods for occluding the patient's airway, modulating airway pressure, or providing impedance-threshold therapy to a patient. Exemplary impedance-threshold techniques include those described in U.S. Pat. Nos. 5,551,420, 5,692,498, 6,062,219, 6,526,973, 6,604,523, 7,210,480, 6,986,349, 7,204,251, 7,195,012, 7,185,649, 7,082,945, 7,195,013, 7,836,881, and 7,766,011, the contents of which are incorporated herein by reference for all purposes. For example, an impedance threshold device can be connected to a patient, optionally via a facemask, and active compression decompression CPR can be performed on the patient. The impedance threshold device can lower intrathoracic pressure during the decompression phase by impeding passive inspiratory gas exchange during the recoil phase, while also allowing periodic positive pressure ventilation. The impedance threshold device can be configured to provide an inspiratory resistance of 16 cm $H_2O$ and less than 5 cm $H_2O$ expiratory impedance, for example.

In some cases, active compression decompression cardiopulmonary resuscitation treatments described herein can be performed in conjunction with the use of systems and methods for providing, facilitating, or modulating negative airway pressure, such as impedance threshold device (ITD) techniques or intrathoracic pressure regulator (ITPR) techniques. Exemplary ITPR approaches are describe in previously incorporated U.S. patent application Ser. No. 12/819,959 filed Jun. 21, 2010. ITD and ITPR techniques can be used to enhance circulation, and may involve a valve system interfaced to a person's airway. Both can be used to lower intrathoracic pressure during the chest wall recoil phase of CPR, thereby enhancing the transfer of blood from outside the thorax into the right heart. Exemplary ITD systems can be configured to prevent or inhibit respiratory gas flow to the person's lungs during the decompression phase until a negative airway pressure achieved equals the opening pressure of the valve system. Exemplary ITPR systems can include a valve system that is used to withdraw air from the lungs via an active vacuum source until a negative airway pressure is achieved. According to some embodiments, ITD approaches can provide perfusion on demand by regulating pressures in the thorax during states of hypotension. ITD techniques may utilize the interdependence of the body's respiratory and circulatory systems to create a vacuum (negative pressure) within the chest during the recoil phase of CPR, which follows each chest compression. ITD techniques can regulate the influx of respiratory gases into the chest during the chest wall recoil (relaxation or decompression) phase, which lowers the intrathoracic pressure and draws more venous blood back to the heart. Improved blood return to the heart (preload) results in improved blood flow out of the heart (cardiac output) during the subsequent compression. Thus, despite its placement into the ventilation circuit, an ITD device can operate as a circulatory enhancer device that works during chest compressions, for example during the chest wall recoil phase of CPR. Whereas ITD techniques can be based on vacuum associated with recoil, ITPR techniques can involve the active application of a vacuum. Exemplary ITPR techniques can be used to generate controlled negative endotracheal pressure (ETP). In some cases, an ITPR system may include a pressure regulator that combines a continuous vacuum source, a regulator valve system, a means to provide intermittent PPV, and an inspiratory ITD, such as that described by Yannopoulos et al. in "Intrathoracic Pressure Regulation Improves 24-Hour Survival in a Porcine Model of Hypovolemic Shock" Anesth. Analg., Vol. 104 No. 1:157-162 (January 2007). Exemplary ITPR techniques are also described by Yannopoulos et al. in "Intrathoracic pressure regulation improves vital organ perfusion pressures in normovolemic and hypovolemic pigs" Resuscitation 70(3):445-53 (September 2006). The entire content of both of these journal articles is incorporated herein by reference for all purposes. In some cases, an ITPR system may include an ITD mechanism that, rather than operating to decrease intrathoracic pressure, instead functions as a safety valve to prevent the vacuum from going extremely negative, and can optionally be replaced by another type of safety valve. Thus, in some instances, in an ITPR technique the negative pressure can be generated by a vacuum line, and not by a ITD mechanism.

Systems and methods for applying guided active compression decompression cardiopulmonary resuscitation as described herein are well suited for use in conjunction with abdominal counter-pulsation and/or compression of the lower extremities, and other treatment techniques such as those described in U.S. patent application Ser. No. 12/165,366 filed Jun. 30, 2008 (Lower Extremity Compression Devices, Systems And Methods To Enhance Circulation) for enhancing venous return. The entire content of this application is incorporated herein by reference for all purposes. For example, guided active compression decompression cardiopulmonary resuscitation can be used in combination with techniques or devices that compress the lower extremities using counter pulsation, gas inflated cuffs, fitted around a portion of the thighs or the entire lower body, which can be triggered by the decompression phase of CPR. The lower extremity device accomplishes two main objectives. Such combination treatments are well suited for use in increasing circulation during cardiac arrest and CPR and other states of low blood pressure.

Exemplary Chest Compression Treatments and Systems

Performing CPR may include performing standard CPR or performing active compression decompression (ACD) CPR. The method may also include binding, manually or with an abdominal compression device, at least a portion of the person's abdomen. It may also include techniques to prevent blood flow to the legs, for example by binding the lower extremities, either continuous or in a synchronized manner with chest compressions. The method may also include at least temporarily preventing or impeding airflow to the person's lungs during at least a portion of the relaxation or decompression phase using an impedance threshold device (ITD) that is coupled with the person's airway. Such ITDs may entirely or substantially prevent or hinder respiratory gases from entering the lungs during some or all of the relaxation or decompression phase of CPR. As one specific example, an ITD may prevent respiratory gases from entering the lungs during the decompression phase until the person's negative intrathoracic pressure reaches a certain threshold, at which point a valve opens to permit respiratory gases to enter the lungs. The method may also include regulating the airflow to or from the person's lungs using an intrathoracic pressure regulator (ITPR). Such ITPRs may actively extract gases from the lungs during some or all of the relaxation or decompression phase of CPR. For example, a vacuum source may provide a continuous low-level vacuum except when a positive pressure breath is given by a ventilation source, e.g. manual or mechanical resuscitator. The applied vacuum decreases the intrathoracic pressure. Improving the artificial circulation created by the CPR may include increasing the carotid blood flow or increasing systolic and diastolic blood pressures. The method may also include stopping CPR and then restarting it multiple times, such as by, for example, in 30 second epochs for four cycles, to help preserve heart and brain function from reperfusion injury. Such a process may be referred to as stutter CPR. If stutter CPR (either ACD CPR or standard CPR) is to be performed manually, instructions and/or an aid may be provided so that the rescue personnel will have information about the sequence of delivering CPR and SNP, including in some embodiments, how to deliver the drug or drugs and perform stop/start or stutter CPR. In some cases, devices used to perform CPR may be programmed to perform stop/start or stutter CPR or have such a mode available.

In a further embodiment, blood flow within a patient who is in cardiac arrest is modulated or controlled to control blood flow to the heart and brain, with or without the administration of a vasodilator drug. This is done so that the vital organs receive blood in a controlled fashion. This may be particularly useful as changes in blood flow may facilitate release of endogenous vasodilators. In one aspect, blood flow is controlled or modulated so that the vital organs slowly receive additional blood over time. This may be done in a ramping fashion where the amount of blood supplied to the vital organs is slowly increased over time, or in a "stutter" fashion where blood is circulated to the vital organs for a certain time, then stopped, then again circulated. In some cases, combinations of the two methods could be used. In one specific aspect, blood circulation is controlled by stopping and starting CPR to protect against reperfusion injury by post-conditioning.

Another feature encompassed by embodiments of the present invention is the ability to control or modulate blood flow within a patient who is in cardiac arrest, and in particular, to control blood flow to the heart and brain, with or without the administration of a vasodilator drug, such that the vital organs receive blood in a controlled fashion. This may be particularly useful as changes in blood flow may facilitate release of endogenous vasodilators. More specifically, blood flow is controlled or modulated so that the vital organs slowly receive additional blood over time. This may be done in a ramping fashion where the amount of blood supplied to the vital organs is slowly increased over time, or in a "stutter" fashion where blood is circulated to the vital organs for a certain time, then stopped, then again circulated. In some cases, combinations of the two methods could be used.

Merely by way of example, blood circulation may be ramped up over time so that initially the blood flow to the vital organs may be about 5% to 100% of what a healthy person may expect to receive with normal heart function. Over a time period of about <1 minute to over an hour, the circulation may be increased so that the blood flow to the vital organs is about 5% to about 100% and even higher of what a healthy person may expect to receive. The ramping function could be linear, non-linear, or may jump in discrete steps.

For the "stutter" process, blood may be circulated to the vital organs for set start and stop times, such as by causing circulation for about 40 seconds, and then stopping circulation for about 20 seconds, and then resuming circulation for 40 about seconds, and then stopping circulation for about 20 seconds, etc. The time intervals where circulation occurs and is stopped could remain the same, or could vary over time. For example, the time during which circulation occurs could increase over time. The time during which circulation is stopped could also vary over time, such as by decreasing the length of the stopping periods over time.

Blood circulation may be facilitated in a variety of ways, including manual or automated CPR or ACD CPR, external or internal blood pumps, pressure cuffs, lateral gravity (g) acceleration, and the like. Software programs may be employed to control circulation devices so that blood circulation to the vital organs may be controlled as just described. Similarly, manual instructions may be provided to rescuers performing manual blood circulation techniques, such as standard CPR. Further, instructions may be provided for when to administer a vasodilator drug during the process, if appropriate.

As one specific example, the effectiveness of CPR with SNP or a SNP-like drug can be further enhanced by providing CPR for a period of time, for example 40 seconds, and then stopping for 20 seconds, and then resuming CPR for 40 seconds, and then stopping CPR for 20 seconds, and then resuming CPR. Use of between 0.05 and 1 mg of epinephrine during this post-conditioning process can be used to further improve circulation of blood flow to the heart and brain and long-term neurologically-intact survival rates. If such a "stutter" CPR process (either ACD CPR or standard CPR) is to be performed manually, a kit may be provided with instructions and/or a mechanical aid so that the rescue personnel will have information about the sequence of delivering CPR and SNP, including in some embodiments, how to deliver the drug or drugs and perform stop/start or stutter CPR. In some cases, CPR will be performed using a mechanized device, and such devices used to perform CPR may be programmed to perform stop/start or stutter CPR or have such a mode available.

One specific example of such a method is based on the observation that mechanical post conditioning (PC) with intermittent initiation of flow ("stutter" reperfusion) has been shown to decrease infarction size in ST elevation infarction and decrease ischemic stroke size in animals. An experiment was performed to determine whether when using sodium nitroprusside-enhanced (SNPeCPR) cardiopulmonary resuscitation (CPR), mechanical post conditioning with stutter CPR (20-second CPR pauses), begun immediately on SNPeCPR initiation, improves 24-hour cerebral function compared to 12 hours of therapeutic hypothermia (TH) post resuscitation.

This was shown in an experiment using 14 anesthetized and intubated pigs that underwent 15 minutes of untreated VF followed by 5 minutes of SNPeCPR comprised of active compression decompression CPR plus an inspiratory impedance threshold device combined with abdominal binding. The ITD prevented respiratory gases from entering the lungs during the decompression phase of CPR. In this example, the ITD had a safety check valve that would allow for inspiration when the intrathoracic pressure was less than minus 16 cm $H_2O$, which does not occur during CPR. The abdomen in this example was compressed with 40-50 lbs of pressure, applied continuously with a bend human arm, using the forearm and a force gauge. Further, 2 mg of sodium nitroprusside (SNP) were given IV at minute 1 and 1 mg at minute 3 of CPR. All animals received in addition 0.5 mg of epinephrine at minute 5, 30 seconds before the first defibrillation attempt. Six animals (PC group), were treated with 40 seconds of SNPeCPR and the first dose of SNP were followed by 20-second pauses (cessation of perfusion) and 20 second of SNPeCPR for at total of 4 cycles for up to 3 minutes. After that animals had uninterrupted SNPeCPR until defibrillation at minute 5. The other 8 animals (TH group) had SNPeCPR for a total of 5 minutes without interruptions. The TH group received 12 hours of TH (core temp=33° C.). The PC group received no TH.

Cerebral performance was scored at 24 hours by a veterinarian blinded to the treatment group.

During SNPeCPR, there were no hemodynamic differences except for a significantly higher aortic pressure response to epinephrine at min 5 (SBP/DBP; 148±12/78±7 in the PC group versus 110±9/62±5 mmHg in the TH group, p<0.05). Return of spontaneous circulation rates and 24-hour survival was 100% for both groups. CPC was significantly lower in the PC group (1±0) versus the TH group (2.4±0.8), p<0.01. Hence, in this porcine model of cardiac arrest and SNPeCPR, mechanical PC with pauses in compressions at the initiation of the resuscitation efforts prevented 24-hour neurological dysfunction after 15 minutes of untreated VF and was superior to TH.

Figure 13:
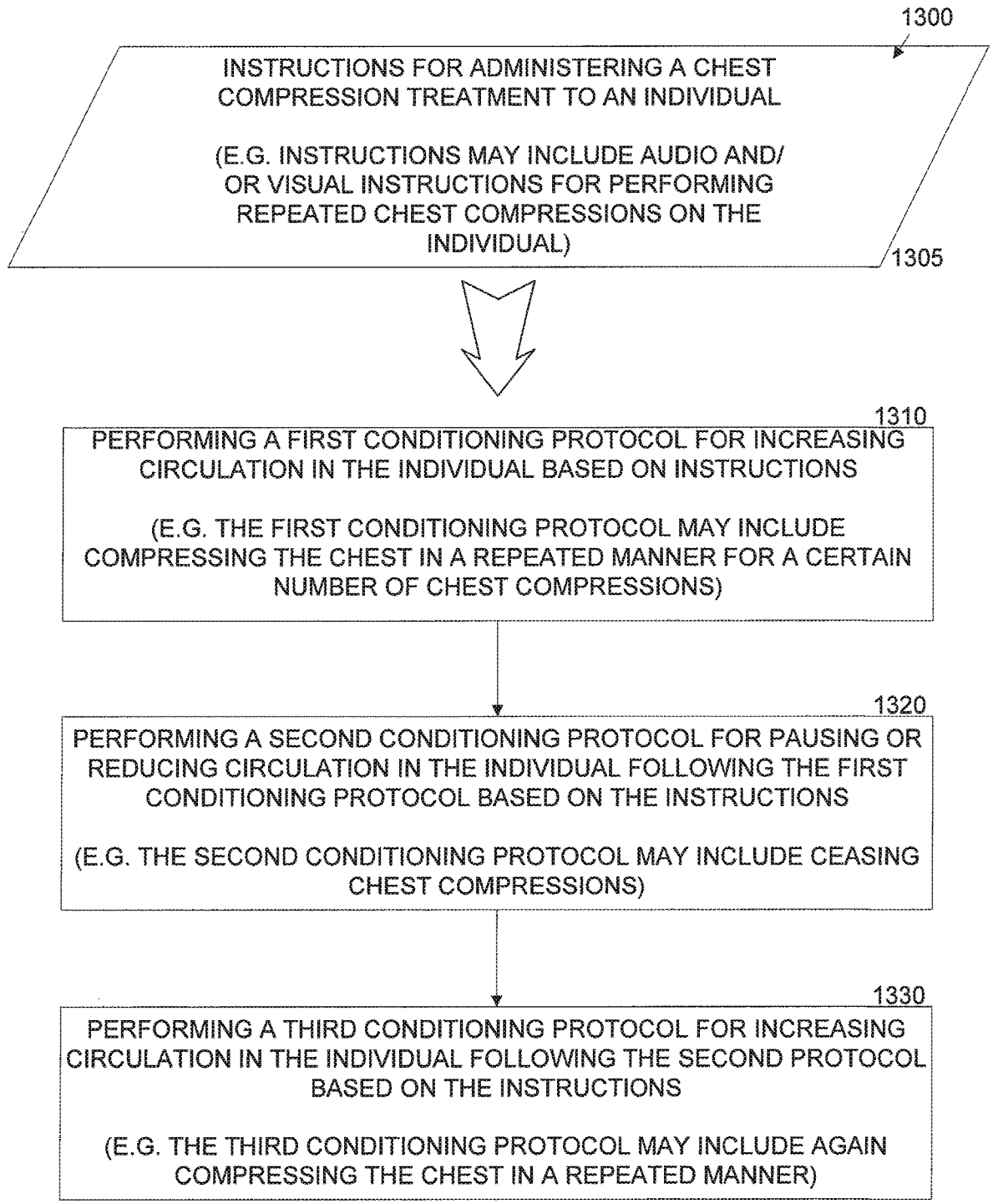
FIG. 13 illustrates aspects of exemplary treatment methods according to embodiments of the present invention.

FIG. 13 illustrates aspects of a treatment method according to embodiments of the present invention. As shown here, method 1300 includes performing a first conditioning protocol for increasing circulation in the individual, as indicated by step 1310, performing a second conditioning protocol for pausing or reducing circulation in the individual following the first conditioning protocol, as indicated by step 1320, and performing a third conditioning protocol for increasing circulation in the individual following the second protocol, as indicated by step 1330. In some instances, the conditioning protocols can be performed by an operator based on instructions 1305 for administering a chest compression treatment. As shown here, treatment instructions 1305 may include audio instructions, visual instructions, or any combination thereof, for performing repeated chest compressions on the individual. According to some embodiments, methods may include providing such instructions to the operator. Instructions may be provided to the operator, for example, by any of the treatment systems described herein, for example systems such as those depicted in FIG. 1A or FIG. 4. In some cases, instructions may be provided, at least in part, by an auxiliary device that is separate from a cardiopulmonary resuscitation system. For example, instructions may be provided to an operator by a mobile phone or any other electronic device. In some cases, some or all of the instructions may be stored by the system. In some cases, some or all of the instructions may be received by the system and transmitted to the operator by the system. Hence, any or all of the treatment protocols can be performed by the operator based on the instructions. In some instances, the first conditioning protocol includes compressing the chest in a repeated manner for a certain number of chest compressions. In some instances, the second conditioning protocol includes ceasing chest compressions. In some instances, the third protocol includes again compressing the chest in a repeated manner.

According to some embodiments, the first conditioning protocol may include a series of periodic active chest compressions and decompressions. In some cases, the third conditioning protocol may include a series of periodic active chest compressions and decompressions. In some cases, each of the first and third conditioning protocols comprise a series of periodic active chest compressions and decompressions. Optionally, treatment methods may include administering an electrical defibrillation treatment to the individual. Relatedly, treatment instructions provided by the system may include operator instructions for delivering an electrical defibrillation treatment to the individual. In some cases, treatment methods may include modulating a pressure within an airway of the individual. Relatedly, treatment instructions provided by the system may include operator instructions for modulating a pressure within an airway of the individual. It is understood that treatment instructions described herein may encompass instructions for a single operator, as well as instructions for multiple operators, for example in situations where more than one operator may be involved with administering a treatment to an individual.

Figure 14:
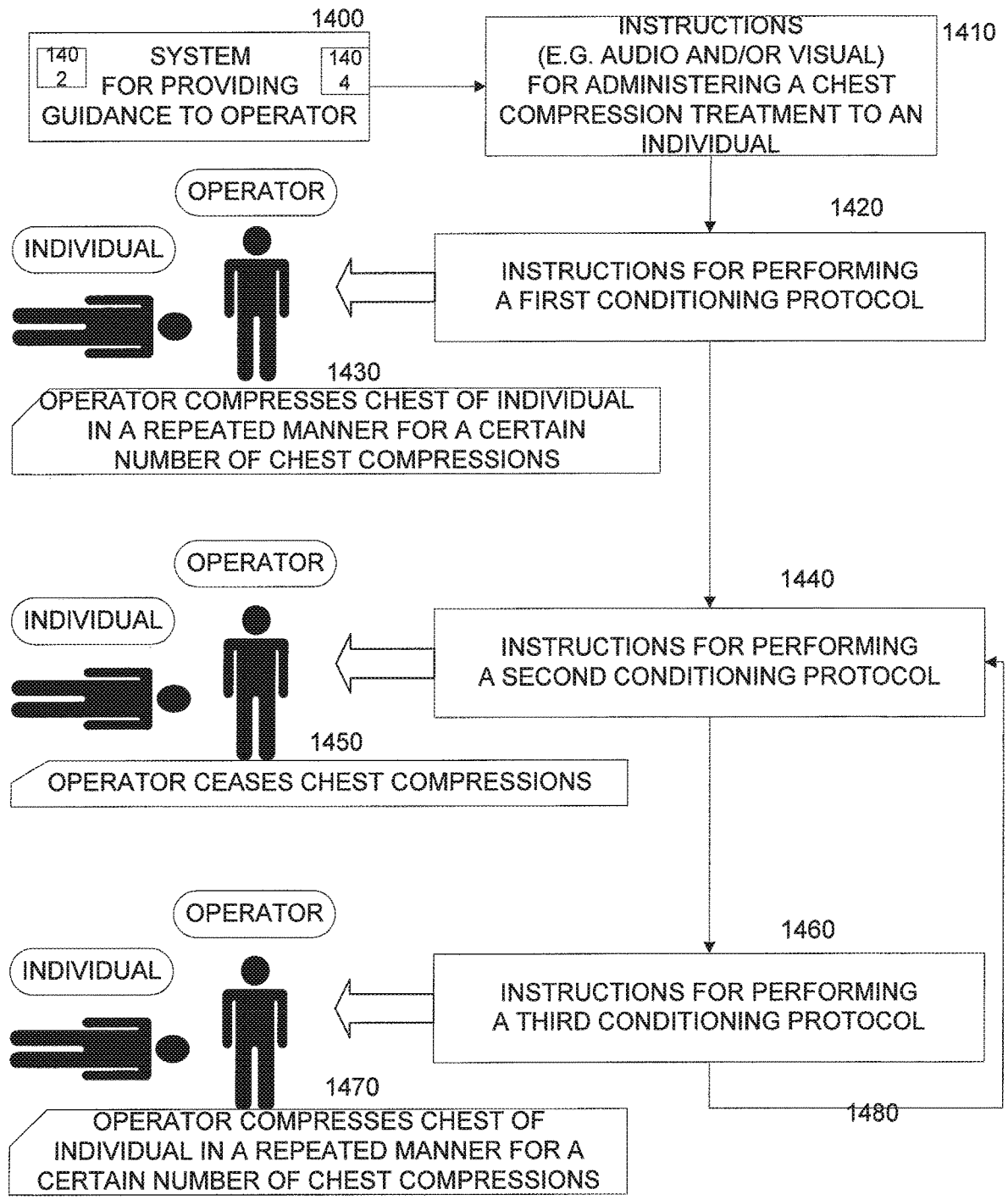
FIG. 14 illustrates aspects of exemplary treatment systems according to embodiments of the present invention.

FIG. 14 illustrates aspects of a treatment system according to embodiments of the present invention. As shown here, system can be configured to provide guidance to an operator, for example for administering a circulatory treatment to an individual. Hence, system may be configured to provide such instructions in any way that can be understood or perceived by an operator. For example, system may provide at least a portion of the instructions in an audio format. For example, the system may include a loudspeaker that transmits instructions by sound for performing treatment steps, which can be heard by an operator. Such auditory instructions may include voice commands such as "Begin Chest Compressions", "Cease Chest Compressions", "Resume Chest Compressions", and the like. Similarly, system 400 may provide at least a portion of the instructions in a visual format. For example, the system may include a graphical user interface that transmits instructions which can be visualized by an operator. Such visual instructions may include text or display messages such as "Begin Chest Compressions", "Cease Chest Compressions", "Resume Chest Compressions", and the like. In some case, visual instructions can be provided by lighted icons. For example, a green light can provide a signal that the operator should begin chest or compressions, and a red light can provide a signal that the operator should cease chest compressions. According to some embodiments, instructions for administering treatment protocols may be provided as a combination of visual and audio signals. For example, the system may emit a sound command of "Begin Chest Compressions" and at the same time display a text or visual display instructing the operator to begin chest compressions. Similarly, the system may emit a sound command of "Cease Chest Compressions" and at the same time display a text or visual display instructing the operator to cease chest compressions. In some cases, system can include one or more features or components of the various systems described herein, such as those depicted in FIG. 1A or FIG. 4.

The system or device may also include a button or input mechanism as a means by which a rescuer may select one of at least two CPR options. In option A, bystander CPR has been performed previously by lay rescue personnel, and no stutter CPR as described herein are to be delivered, and thus the device is configured or programmed to provide no instructions for the stutter method of CPR. The device would be programmed, once the button A is pushed to instruct on how to perform CPR without intentional interruptions. If there was no lay rescuer CPR or bystander CPR previously performed, then a selection of Option B would configure the device to provide the rescuer instructions on how to perform stutter CPR with the intentional interruptions and optionally provide feedback when it was not being performed adequately or as proscribed so the rescuer could improve what they are doing and perform the appropriate CPR.

As shown in FIG. 14, in some cases system may include a module 1402 that stores, generates, or receives treatment information. In some cases, system may include a module or operator interface 1404 that transmits, provides, or displays instructions, optionally based on the treatment information. A set of instructions 1410 may include instructions for performing a first conditioning protocol 1420 for increasing circulation in the individual, instructions for performing a second conditioning protocol 1440 for pausing or reducing circulation in the individual following the first conditioning protocol, and instructions for performing a third conditioning protocol 1460 for increasing circulation in the individual following the second protocol. The first conditioning protocol may include compressing the chest in a repeated manner for a certain number of chest compressions. Hence, as illustrated here, in response to or based on the instructions, the operator can compress the chest in a repeated manner for a certain number of chest compressions as indicated by step 1430. The second protocol may include ceasing chest compressions. Hence, as illustrated here, in response to or based on the instructions, the operator can cease chest compressions, as indicated by step 1450. The third protocol may include again compressing the chest in a repeated manner. Hence, as illustrated here, in response to or based on the instructions, the operator can again compress the chest of the individual in a repeated manner, as indicated by step 1470. According to some embodiments, each of the first and third conditioning protocols include a series of periodic active chest compressions and decompressions. In some cases, each of the first and third conditioning protocol include a duration, and the first conditioning protocol duration is different from the second conditioning protocol duration. In some cases, each of the first and third conditioning protocol include a duration, and the first conditioning protocol duration is equal to the second conditioning protocol duration. In some instances, the instructions may include guidance to the operator to repeat certain aspects of the treatment. For example, as shown by the arrow 1480 between the third and second protocol instructions, the treatment instructions may guide the operator to cease chest compressions following the compression protocol of step 1470.

Figure 15:
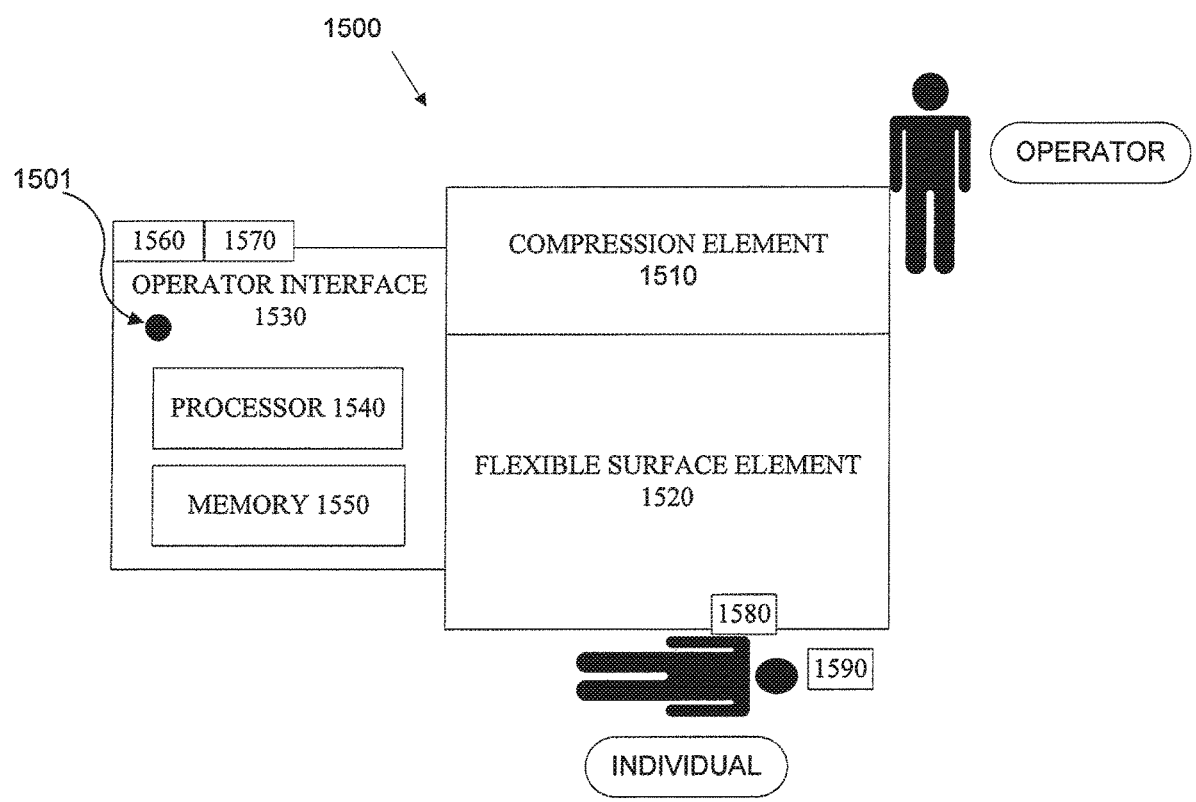
FIG. 15 illustrates aspects of exemplary treatment systems according to embodiments of the present invention.

Related embodiments of the present invention encompass systems for applying guided active compression decompression cardiopulmonary resuscitation to an individual by an operator. For example, as illustrated in FIG. 15, an exemplary system 1500 may include a compression element 1510 that is pressed and lifted by an operator, a flexible surface element 1520 coupled with the compression element 1510 and removably attachable to a chest area of the individual, and an operator interface 1530 that provides guidance to the operator as to how to perform chest compressions. System 1500 may also include a processor 1540 operably coupled with the operator interface 1530, and a memory 1550 that is configured to store instructions executable by the processor 1540 to provide a set of operator instructions to perform various conditioning protocols. For example, the memory 1550 may store instructions executable by the processor 1540 to provide a set of instructions to the operator to perform a first conditioning protocol for increasing circulation in the individual by compressing the chest in a repeated manner for a certain number of chest compressions. Further, the memory 1550 may store instructions executable by the processor 1540 to provide a set of instructions to the operator to perform a second conditioning protocol for pausing or reducing circulation in the individual following the first conditioning protocol by stopping chest compressions for a certain time duration. Moreover, the memory 1550 may store instructions executable by the processor 1540 to provide a set of instructions to the operator to perform a third conditioning protocol for increasing circulation in the individual following the second protocol by again compressing the chest in a repeated manner for a certain number of chest compressions. In some cases, each of the first and third conditioning protocols include a series of periodic active chest compressions and decompressions. In some cases, each of the first and third conditioning protocol comprise a duration, and the first conditioning protocol duration is different from the second conditioning protocol duration. In some cases, each of the first and third conditioning protocol include a duration, and the first conditioning protocol duration is equal to the second conditioning protocol duration. In one example, the first conditioning protocol includes a duration of about 40 seconds, the duration of the second conditioning protocol is about 20 seconds, and the third conditioning protocol includes a duration of about 40 seconds. As shown in FIG. 15, system 1500 can include a display subsystem 1560 that provides at least a portion of the guided treatment instructions. System 1500 may also include an audio output device 1570, such as a loudspeaker, that provides at least a portion of the guided treatment instructions. According to some embodiments, an operator interface 1530 may include a display subsystem 1560, an audio output device 1570, or both, that provide at least a portion of the guided treatment instructions. In some instances, the system may also include a means 1580 for delivering an electrical defibrillation treatment to the individual. In some embodiments, the set of operator instructions can be based at least in part on a physiological parameter of the patient. For example, a patient parameter may include a ventilation rate, a body temperature, a heart rate, a respiratory rate, a vital sign, an end tidal carbon dioxide measure, or the like. In some embodiments, a system 1500 may include a pressure regulator mechanism 1590 that modulates pressure within an airway of the individual. According to some embodiments, memory 1550 may be configured to store instructions executable by the processor 1540 to receive information indicating whether the operator is following the set of operator instructions, and to provide a signal indicating whether the operator is following the set of operator instructions. As shown here, system or device 1500 may include an input mechanism or button 1501 that can be actuated by an operator or user, to provide an input information to the processor regarding whether a patient or subject has previously received CPR, which can configure the system to provide (or not provide) instructions for stutter CPR, as described elsewhere herein.

In some embodiments, systems or devices can be configured to provide a set of operator instructions to perform a first conditioning protocol for increasing circulation in the individual by compressing the chest in a repeated manner for a certain time duration, a second conditioning protocol for pausing or reducing circulation in the individual following the first conditioning protocol by stopping chest compressions for a certain time duration, and a third conditioning protocol for increasing circulation in the individual following the second protocol by again compressing the chest in a repeated manner for a certain time duration. For example, the first time duration may be about 40 seconds (e.g. administration of CPR), the second time duration may be about 20 seconds (e.g. cessation of CPR), and the third time duration may be about 20 seconds (e.g. administration of CPR). In an exemplary embodiment, the set of instructions may subsequently guide the user or operator to cease CPR for about 20 seconds, administer CPR for about 20 seconds, cease CPR for about 20 seconds, and administer CPR for about 60 seconds. Following the CPR application instructions, the device or system may optionally instruct an operator or individual to administer to treated subject a vasopressor drug such as adrenalin and/or a vasodilator such as sodium nitroprusside. Where such therapeutic agents are administered to the patient or subject being treated, the device or system may instruct an operator or individual to subsequently provide further CPR for an additional period of time, ranging from between 0 seconds and 60 seconds, for example, and may also instruct an operator or individual to administer an electrical shock to the subject being treated. The system or device may also assess one or more physiological parameters of the subject being treated, or cue the user or operator to assess one or more physiological parameters of the subject being treated, including end tidal CO2 levels, ECG waveforms, and the like, as a way to determine when to deliver the electrical shock. Hence, the timing of the delivered electrical shock can be based on one or more assessed physiological parameters of the subject.

In some instances, methods may involve delivering CPR with a device that delivers standard CPR and/or ACD CPR. In some instances, CPR can be delivered in conjunction with an ITD and/or ITPR therapy. In some instances, the CPR optionally in combination with ITD and/or ITPR can be provided to the subject in an automated manner. In some instances, the CPR optionally in combination with ITD and/or ITPR can be provided to the subject manually. Hence, embodiments of the present invention may incorporate combined ACD CPR and negative intrathoracic pressure treatment modalities, including aspects of combined treatments such as those described in Aufderheide et al., "Standard cardiopulmonary resuscitation versus active compression-decompression cardiopulmonary resuscitation with augmentation of negative intrathoracic pressure for out-of-hospital cardiac arrest: A randomised trial." Lancet 377:301-311 (2011), the content of which is incorporated herein by reference.

In some instances, techniques disclosed herein may involve, following a period of untreated ventricular fibrillation, performing CPR with a number of defined and controlled pauses during the first three minutes of basic life support (BLS) in conjunction with a means to optimize blood flow to the heart and brain subsequently, so as to normalize brain and heart function soon after arrest. In some instances, the guided administration of three to four twenty-second pauses within the first three minutes of CPR provides a therapeutic effect to the subject. Such combinations of simple and specific mechanical interventions can protect the heart and brain from injury and subsequently enhance CPR-generated blood flow to the heart and brain leading to improve resuscitation outcomes, optionally in the absence of epinephrine or other vasopressors.

Intermittent pauses during initiation of CPR is thus helpful for treating subjects in cardiac arrest. Controlled stutter CPR after prolonged global ischemia in cardiac arrest exhibits benefits for the myocardium and mitigates post resuscitation cardiac dysfunction that contributes heavily to post resuscitation morbidity and mortality. ACD CPR with stutter CPR, optionally in combination with ITD and/or ITPR can be widely applied at the first responder level, without ALS support. The concurrent use of controlled pauses during the initiation of ACD CPR (optionally with ITD and/or ITPR) can limit reperfusion and subsequent ischemic injury. Systems and devices as disclosed herein can be configured to guide a rescuer such as a basic EMS user or lay person on how to perform high quality CPR with controlled pauses and simultaneously monitor and record that performance. These techniques can improve clinical outcomes and provide a means to help assure, assess, and maintain performance of quality CPR. Without being bound by any particular theory, it is thought that the type of intentional pauses described herein may operate to harness endogenous protective processes associated with specific mitochondrial protective mechanics. Surprisingly, the techniques described herein indicate that the brain may demonstrate the potential for full recovery after 15 minutes of global ischemia with no flow following the administration of a non-invasive treatment.

ACD CPR utilized a suction cup or other attachment mechanism to actively lift the chest wall during the decompression phase enhances the refilling of the heart in between compressions, and can be combined with either an ITD or another means to lower intrathoracic pressures and prevent the influx of respiratory gases into the lungs during the chest decompression phase of CPR. An ITD may operate by allowing air to exit the chest during each compression but impedes air entry during the chest recoil or decompression phase until airway pressure falls below −10 or −16 cm $H_2O$, depending upon the ITD used. Due to the rapid transmission of intrathoracic vascular pressures and intrathoracic pressure throughout the chest and brain, use of ACD CPR+ITD decreases right atrial pressure and ICP while increasing aortic pressure and forward flow, thereby providing enhanced blood flow to the heart and brain. As disclosed herein, ACD CPR devices can utilize software to instruct the user how to perform ACD CPR, and can also utilize an adhesive pad which adheres to the patient's chest to provide ACD CPR. The device can be configured to provide audible and visual cues which instruct a user to perform ACD CPR, optionally in conjunction with controlled intermittent CPR, and also optionally in conjunction with ITD and/or ITPR therapy.

Exemplary systems or methods may also include an input mechanism that receives information from a user or rescuer related to whether the patient has previously received CPR treatment. For example, a device such as ACD CPR device 100 *a* of FIG. 1 may include a button or toggle on the front of the device, which may be activated or pressed by a rescuer. Relatedly, input mechanism 1501 of FIG. 15 may provide such an input. The input may allow the rescuer to select one of at least two CPR options. The selection may be based on whether the subject has received CPR treatment (e.g. manual CPR administered by a bystander), before the rescuer begins using the ACD CPR device. For example, Option A may be selected if the subject has previously received CPR treatment from a bystander. In this case, upon selection of Option A, the device is configured to provide instructions to the operator which do not include the administration of a stutter CPR. Alternatively, Option B may be selected if the subject has not previously received CPR treatment. In this case, upon selection of Option B, the device is configured to provide instructions to the operator which do include the administration of stutter CPR.

Exemplary systems or devices can be configured to provide a user or operator with audible and/or visual prompts for administering one or more aspects of the treatment methods disclosed herein. For example, systems or devices may include an interface that guides the user to perform CPR with controlled pauses, and that provides the user with continuous feedback on the quality of the CPR administered. Systems or devices may also incorporate software that allows the user to download or transmit information on the quality of the CPR. In some instances, systems or devices are configured to instruct a user to provide 20 second pauses during CPR. In some instances, systems or devices are configured to provide guidance and real-time feedback to the user to improve the effectiveness of CPR. The systems and devices disclosed herein encompass manual ACD CPR apparatuses capable of providing instructions for performing combined ACD CPR and controlled pause CPR therapy, optionally in conjunction with ITD and/or ITPR, as well as real-time feedback on the quality of CPR being performed. Exemplary systems or devices may include a visual interface that cues the user to stop (PAUSE) or start (RESUME) compressions during the initial four minutes (or other initial duration time period) of CPR.

Figure 16:
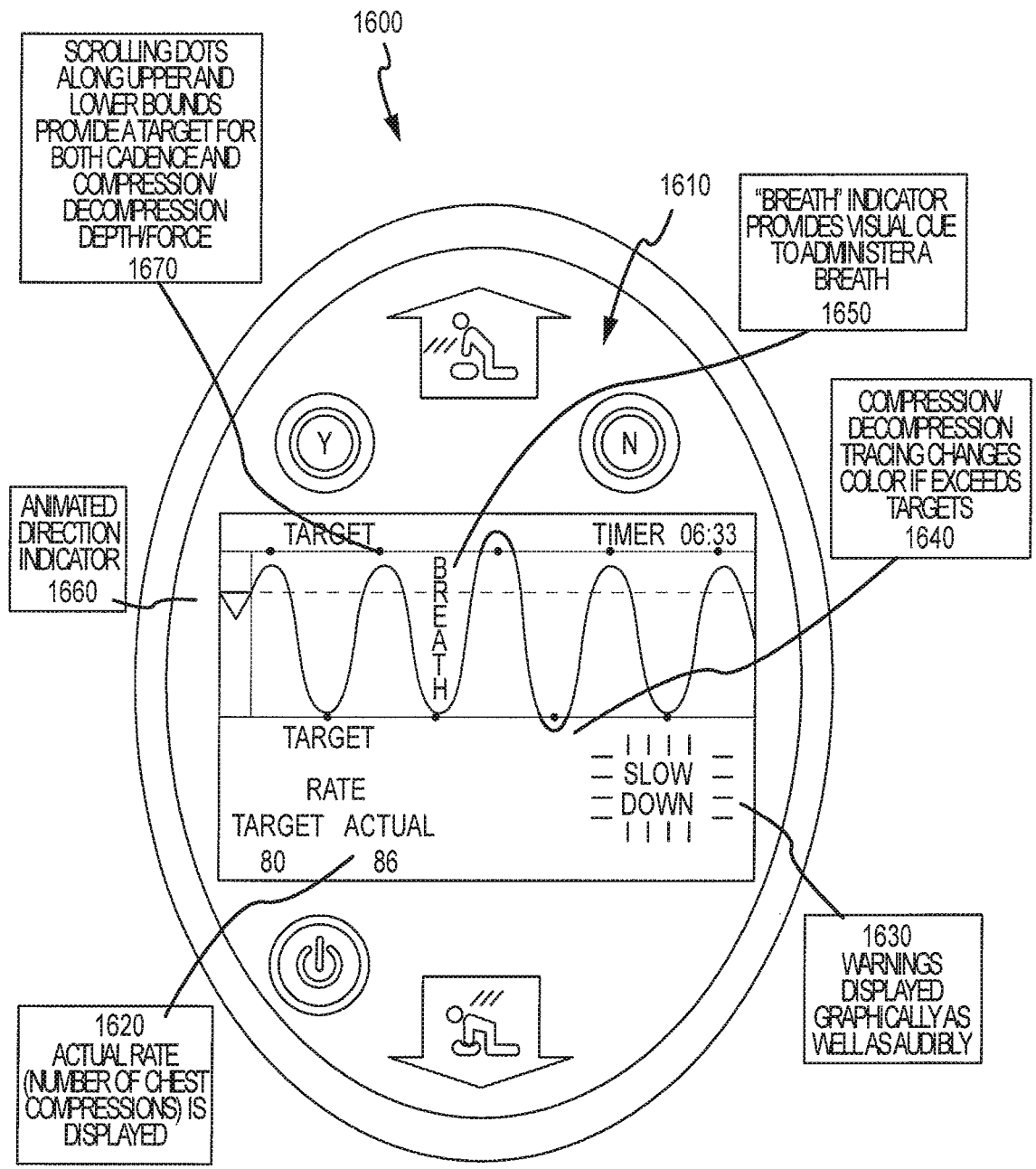
FIG. 16 illustrates aspects of exemplary treatment systems according to embodiments of the present invention.

FIG. 16 depicts an exemplary interface configuration according to embodiments of the present invention. As shown here, system 1600 may have an interface 1610 that includes a display 1620 for numerically showing the target compression rate, as well as the actual rate (e.g. number of chest compressions per minute). Interface 1610 may also include a display for showing warnings 1630 (e.g. "slow down"). The warnings may be provided to the operator visually and/or audibly. Further, the interface may provide a signal or indication to the operator regarding the compression/decompression depth/force, and can also provide a signal 1640 indicating that target depths and/or forces have been exceeded. In some instances, the interface 1610 may provide a breath indicator 1650, which provides a visual cue to an operator or rescuer to administer a breath to the patient or subject being treated. Interface 1610 may also include an animated direction indicator 1660, which guides the user to push on the device toward the patient (e.g. downward facing arrow), or to pull on the device away from the patient (e.g. upward facing arrow). The interface 1610 may further include scrolling dots or indicia 1670 along the upper and/or lower bounds of the depth and/or force targets, thus providing a target for cadence as well as compression and/or decompression.

Exemplary devices may include a force sensor that provides feedback, which can be used to instruct the user to achieve an appropriate compression target. In some instances, a device may include an accelerometer that provides feedback, which can be used to provide the user with specific depth information. For example, a printed circuit board mounted micro-machined single axis capacitive accelerometer, utilizing a double integration of the output of the accelerometer may be sufficient to calculate the relative position. Alternatively, 2 or 3 axis sensors may be employed to generate comprehensive position assessments. Combined accelerometer and force sensor devices can provide accurate compression/decompression readings, particularly in situations (e.g. CPR is performed on a soft surface such as a mattress) where accelerometers alone may not provide an accurate assessment. Systems or devices may employ algorithms or computing means that compare values from the accelerometer and force sensor to determine whether adequate force is being applied in order to achieve a desired amount of displacement (e.g 2 inches). If a target or desired displacement is not achieved, the device can provide a visual and/or audible warning that additional force is required to achieve meaningful chest compressions. Although many of the indicators or cues discussed herein are described in terms of audio or visual terms, it is also understood that systems and devices can be configured to provide feedback, cues, guidance, indicators, and the like in tactile terms. For example, the device may be configured to vibrate so as to provide a particular cue (e.g. deliver compressions with more force) to the user. Hence, any of a variety of visual, audio, and/or tactile means, optionally in any combination thereof, may be employed by the system or device to provide instructions or feedback to the user or operator.

Stutter CPR techniques are described in Segal et al. "Ischemic postconditioning at the initiation of cardiopulmonary resuscitation facilitates functional cardiac and cerebral recovery after prolonged untreated ventricular fibrillation" Resuscitation, Apr. 18, 2012 [Epub ahead of print] and Yannopoulos "Controlled pauses at the initiation of sodium nitroprusside-enhanced cardiopulmonary resuscitation facilitate neurological and cardiac recovery after 15 mins of untreated ventricular fibrillation" Crit Care Med. May 40(5): 1562-9 (2012), the contents of which are incorporated herein by reference. Stutter CPR techniques are also described in U.S. patent application Ser. No. 13/554,458 filed Jul. 20, 2012. Accordingly, the systems and devices disclosed in the instant application can be configured to perform any aspect of the stutter CPR techniques disclosed in those references, and can also be configured to instruct a rescuer or operator to perform any aspect of such stutter CPR techniques.

Embodiments of the invention have now been described in detail for the purposes of clarity and understanding. However, it will be appreciated that certain changes and modifications may be practiced within the scope of the appended claims.

The invention claimed is:

1. A system for treating cardiac arrest in a patient, comprising:
   an active compression decompression device configured to allow an operator to deliver active compression decompression treatment to the patient;
   a flexible surface element provided as a contact pad of the active compression decompression device and configured to adhere to a chest of the patient;
   one or more electrodes arranged with the flexible surface element and configured to contact a chest of the patient to provide electrical defibrillation to the patient;
   at least one electronic sensor associated with at least one of the active compression decompression device and the flexible surface element, the at least one electronic sensor comprising an electronic force sensor configured to measure compression force and decompression force during administration of active compression-decompression cardiopulmonary resuscitation to the patient;
   an operator interface; and
   at least one processor operably coupled to the operator interface and the at least one electronic sensor, the at least one processor configured to provide an indication of the measured compression force or decompression force and an indication of whether the measured force is associated with a compression phase or a decompression phase via the operator interface.

2. The system of claim 1, wherein the flexible surface element comprises an adhesive material on a lower surface of the flexible surface element and is configured to adhere to the chest of the patient.

3. The system of claim 1, wherein the flexible surface element includes guidance for anatomical alignment of the flexible surface element with the chest of the patient.

4. The system of claim 3, wherein the guidance for anatomical alignment of the flexible surface element with the chest of the patient comprises at least one reference notch located at one or more edges of the flexible surface element.

5. The system of claim 1, wherein the active compression decompression device and the flexible surface element are magnetically coupled.

6. The system of claim 1, further comprising one or more electrode leads connecting the one or more electrodes to an electric defibrillator.

7. The system of claim 1, wherein the one or more electrodes comprise an adhesive on a surface thereof configured to contact the chest of the patient.

8. The system of claim 1, wherein the one or more electrodes are configured to facilitate electrocardiographic monitoring of the patient.

9. The system of claim 1, wherein the active compression decompression device comprises a handle adapted to be pressed and lifted by the operator to administer active compression-decompression cardiopulmonary resuscitation.

10. The system of claim 9, wherein the operator interface includes a graphical display that provides guidance for the operator to administer active compression-decompression cardiopulmonary resuscitation.

11. The system of claim 1, wherein the at least one processor is configured to provide an indication of a timing of delivery of chest compressions and chest decompressions.

12. The system of claim 1, wherein the at least one processor is configured to:
receive signals representing the one or more measured parameters from the at least one electronic sensor during the administration of active compression-decompression cardiopulmonary resuscitation to the patient in need of emergency assistance,
calculate, based on the one or more measured parameters, a measurement of compression force and decompression force or depth applied to the patient, compare the measurement of compression and decompression force or depth to a target range, and
control the operator interface to provide real-time feedback on the graphical display for the operator to improve effectiveness of active compression-decompression cardiopulmonary resuscitation, the real-time feedback including a graphical representation of the measured compression force and decompression force or depth applied to the patient and a visual indication in the graphical display of whether the measured compression force and decompression force or depth is within the target range or outside of the target range.

13. The system of claim 1, wherein the at least one electronic sensor comprises a distance sensor.

14. The system of claim 10, wherein the operator interface comprises one or more inputs for receiving input or information from the operator.

15. The system of claim 14, wherein the one or more inputs include a selection of at least one of body size and chest stiffness of the patient.

16. The system of claim 1, further comprising an intrathoracic pressure regulator (ITPR) system that modulates pressure within an airway of the patient.

17. The system of claim 16, further comprising an occlusion mechanism for occluding the airway of the patient during a chest decompression or recoil phase.

18. The system of claim 16, further comprising a negative pressure source for actively removing respiratory gases from lungs of the patient with a continuous or intermittent low-level vacuum.

19. The system of claim 1, wherein the at least one electronic sensor comprises an accelerometer combined with the force sensor.

20. The system of claim 1, wherein the at least one processor is configured to:
compare the measurement of compression force and decompression force to a target range; and
control the operator interface to provide a visual indication in the graphical display of whether the measured compression force and decompression force is within the target range or outside of the target range.

* * * * *